(12) United States Patent
Marchant et al.

(10) Patent No.: US 10,905,646 B2
(45) Date of Patent: Feb. 2, 2021

(54) THERMOPLASTIC POLYURETHANE FILM FOR DELIVERY OF ACTIVE AGENTS TO SKIN SURFACES

(71) Applicant: Lubrizol Advanced Materials, Inc., Cleveland, OH (US)

(72) Inventors: Nancy S. Marchant, Medina, OH (US); Pallavi Kulkarni, Woburn, MA (US); Anthony J. Walder, Essex, MA (US); Paul M. Basone, Akron, OH (US); Shawn Lankowski, Danvers, MA (US); Juan Cebrián Puche, Gava (ES); Sandra Mendez, Gava (ES); Mireia Martin, Gava (ES)

( * ) Notice: Subject to any disclaimer, the term of this patent is extended or adjusted under 35 U.S.C. 154(b) by 330 days.

(21) Appl. No.: 15/520,661

(22) PCT Filed: Oct. 23, 2015

(86) PCT No.: PCT/US2015/057084
§ 371 (c)(1),
(2) Date: Apr. 20, 2017

(87) PCT Pub. No.: WO2016/069396
PCT Pub. Date: May 6, 2016

(65) Prior Publication Data
US 2017/0319462 A1    Nov. 9, 2017

Related U.S. Application Data

(60) Provisional application No. 62/220,552, filed on Sep. 18, 2015, provisional application No. 62/073,314, filed on Oct. 31, 2014.

(51) Int. Cl.
*C08G 18/48* (2006.01)
*A61K 8/00* (2006.01)
(Continued)

(52) U.S. Cl.
CPC .............. *A61K 8/87* (2013.01); *A61K 8/34* (2013.01); *A61K 8/368* (2013.01); *A61K 8/42* (2013.01);
(Continued)

(58) Field of Classification Search
CPC ............ C08G 18/3206; C08G 18/4808; C08G 18/4833; C08G 18/485; C08G 18/6674;
(Continued)

(56) References Cited

U.S. PATENT DOCUMENTS 4,607,025 A    8/1986  Petitou et al.
4,761,401 A    8/1988  Couchman et al.
(Continued)

FOREIGN PATENT DOCUMENTS

EP    0064012    11/1982
EP    0211610    2/1987
(Continued)

OTHER PUBLICATIONS

EP-2105120, Sep. 2009_English Translation.*

*Primary Examiner* — Michael L Leonard
(74) *Attorney, Agent, or Firm* — Fay Sharpe LLP

(57) ABSTRACT

A polymer film suited to use as a face mask or transdermal patch includes at least 30 wt. % of a thermoplastic polyurethane polymer which is the reaction product of a first polyether polyol having a molecular weight of at least 3000 daltons, optionally, a second polyether polyol having a molecular weight of no more than 2500 daltons, at least one of a third polyol having a molecular weight of up to 800 daltons, and a chain extender, a diisocyanate, optionally, a catalyst. The film includes up to 5 wt. % water.

28 Claims, 10 Drawing Sheets
Specification includes a Sequence Listing.

(51) Int. Cl.

| | |
|---|---|
| *A61K 8/87* | (2006.01) |
| *A61K 47/34* | (2017.01) |
| *A61K 9/70* | (2006.01) |
| *A61K 8/34* | (2006.01) |
| *A61K 8/368* | (2006.01) |
| *A61K 8/42* | (2006.01) |
| *A61K 8/64* | (2006.01) |
| *A61K 8/73* | (2006.01) |
| *A61Q 19/02* | (2006.01) |
| *A61Q 19/08* | (2006.01) |
| *A61K 9/00* | (2006.01) |
| *C08G 18/66* | (2006.01) |
| *C09D 175/04* | (2006.01) |
| *C08G 18/75* | (2006.01) |
| *A61K 8/49* | (2006.01) |
| *C08G 18/73* | (2006.01) |
| *C08G 18/32* | (2006.01) |

(52) U.S. Cl.
CPC ............ *A61K 8/498* (2013.01); *A61K 8/4953* (2013.01); *A61K 8/64* (2013.01); *A61K 8/735* (2013.01); *A61K 9/0014* (2013.01); *A61K 9/7007* (2013.01); *A61K 47/34* (2013.01); *A61Q 19/02* (2013.01); *A61Q 19/08* (2013.01); *C08G 18/3206* (2013.01); *C08G 18/485* (2013.01); *C08G 18/4808* (2013.01); *C08G 18/4833* (2013.01); *C08G 18/6674* (2013.01); *C08G 18/73* (2013.01); *C08G 18/758* (2013.01); *C09D 175/04* (2013.01)

(58) Field of Classification Search
CPC ........ C08G 18/73; C08G 18/758; A61K 8/87; A61K 8/64
See application file for complete search history.

(56) References Cited

U.S. PATENT DOCUMENTS

| | | | |
|---|---|---|---|
| 4,789,720 A * | 12/1988 | Teffenhart | A61K 8/0208 528/76 |
| 4,975,441 A | 12/1990 | Gibson | |
| 5,000,955 A | 3/1991 | Gould et al. | |
| 5,015,470 A | 5/1991 | Gibson | |
| 5,081,151 A | 1/1992 | Davis et al. | |
| 5,124,354 A | 6/1992 | Green | |
| 5,334,691 A * | 8/1994 | Gould | A61L 15/26 424/409 |
| 5,962,620 A * | 10/1999 | Reich | A61K 8/87 528/28 |
| 5,993,972 A * | 11/1999 | Reich | A61K 8/87 2/161.7 |
| 6,130,309 A * | 10/2000 | Reich | A61K 8/87 424/401 |
| 6,169,074 B1 | 1/2001 | Montal et al. | |
| 7,015,192 B1 | 3/2006 | Mira et al. | |
| 7,473,679 B2 | 1/2009 | Mira et al. | |
| 7,943,156 B2 | 5/2011 | Almiana Domenech et al. | |
| 8,353,399 B2 | 1/2013 | Ueda et al. | |
| 8,361,272 B2 | 1/2013 | Tuominen et al. | |
| 8,491,926 B2 | 7/2013 | Mohammadi et al. | |
| 8,557,281 B2 | 10/2013 | Halliday et al. | |
| 2004/0022830 A1 | 2/2004 | Nakamura et al. | |
| 2004/0265395 A1 | 12/2004 | Sun et al. | |
| 2005/0063932 A1 * | 3/2005 | Dilallo | A61K 8/64 424/70.14 |
| 2006/0104931 A1 | 5/2006 | Fukutome et al. | |
| 2007/0202070 A1 | 8/2007 | Kamachi et al. | |
| 2009/0155317 A1 | 6/2009 | Ferrer Montiel et al. | |
| 2010/0021510 A1 | 1/2010 | Carreno Serraima et al. | |
| 2010/0098769 A1 | 4/2010 | Ferrer Montiel et al. | |
| 2010/0136071 A1 | 6/2010 | Deckner et al. | |
| 2010/0228204 A1 | 9/2010 | Beatty et al. | |
| 2010/0239061 A1 | 9/2010 | Aoki et al. | |
| 2010/0239621 A1 | 9/2010 | Tsujihata | |
| 2010/0247587 A1 | 9/2010 | Cebrian Puche et al. | |
| 2011/0002969 A1 | 1/2011 | Serraima et al. | |
| 2011/0152795 A1 | 6/2011 | Aledo et al. | |
| 2011/0195102 A1 | 8/2011 | Van Den Nest et al. | |
| 2011/0300199 A1 | 12/2011 | Garcia Sanz et al. | |
| 2012/0021029 A1 | 1/2012 | Garcia Sanz et al. | |
| 2012/0073030 A1 | 3/2012 | Beatty et al. | |
| 2012/0107387 A1 | 5/2012 | Ochiai et al. | |
| 2012/0121675 A1 | 5/2012 | Garcia Sanz et al. | |
| 2013/0012664 A1 * | 1/2013 | Xie | C08G 18/12 525/419 |
| 2013/0101662 A1 | 4/2013 | Carreno Serraima et al. | |
| 2013/0116616 A1 | 5/2013 | Buchholz et al. | |
| 2013/0142743 A1 | 6/2013 | Cavazzuti et al. | |
| 2013/0309281 A1 | 11/2013 | Alminana Domenech et al. | |
| 2014/0120141 A1 | 5/2014 | Garcia Anton et al. | |
| 2014/0318565 A1 | 10/2014 | Ito et al. | |
| 2015/0080352 A1 | 3/2015 | Viala et al. | |
| 2015/0183823 A1 | 7/2015 | Garcia Sanz et al. | |
| 2015/0342852 A1 | 12/2015 | Van Den Nest et al. | |
| 2016/0045423 A1 | 2/2016 | Delgado Gonzalez et al. | |
| 2016/0075738 A1 | 3/2016 | Ferrer Montiel et al. | |

FOREIGN PATENT DOCUMENTS

| | | | |
|---|---|---|---|
| EP | 0277428 | 8/1988 | |
| EP | 0334586 | 9/1989 | |
| EP | 0375388 | 6/1990 | |
| EP | 0403238 | 12/1990 | |
| EP | 1289487 | 12/2006 | |
| EP | 2105120 * | 9/2009 | ............ A61K 8/87 |
| EP | 2 159 223 | 3/2010 | |
| EP | 2159223 | 3/2010 | |
| EP | 2 371 237 | 10/2011 | |
| EP | 2520280 | 11/2012 | |
| WO | WO 98/08884 | 3/1998 | |
| WO | WO 2008/100647 | 8/2008 | |
| WO | WO 2010/064710 | 6/2010 | |
| WO | WO 2013/077088 | 5/2013 | |
| WO | WO 2013/131969 | 9/2013 | |
| WO | WO 2014/086785 | 6/2014 | |
| WO | WO 2014/147255 | 9/2014 | |
| WO | WO 2014/170347 | 10/2014 | |
| WO | WO 2015/063240 | 5/2015 | |

* cited by examiner

```
                              SEQUENCE LISTING

<160> NUMBER OF SEQ ID NOS: 62

<210> SEQ ID NO 1
<211> LENGTH: 37
<212> TYPE: PRT
<213> ORGANISM: Homo sapiens

<400> SEQUENCE: 1

Glu Ile Asp Thr Gln Asn Arg Gln Ile Asp Arg Ile Met Glu Lys Ala
1               5                   10                  15

Asp Ser Asn Lys Thr Arg Ile Asp Glu Ala Asn Gln Arg Ala Thr Lys
            20                  25                  30

Met Leu Gly Ser Ser
        35

<210> SEQ ID NO 2
<211> LENGTH: 20
<212> TYPE: PRT
<213> ORGANISM: Homo sapiens

<400> SEQUENCE: 2

Glu Ile Asp Thr Gln Asn Arg Gln Ile Asp Arg Ile Met Glu Lys Ala
1               5                   10                  15

Asp Ser Asn Lys
            20

<210> SEQ ID NO 3
<211> LENGTH: 26
<212> TYPE: PRT
<213> ORGANISM: Homo sapiens

<400> SEQUENCE: 3

Ile Met Glu Lys Ala Asp Ser Asn Lys Thr Arg Ile Asp Glu Ala Asn
1               5                   10                  15

Gln Arg Ala Thr Lys Met Leu Gly Ser Gly
            20                  25

<210> SEQ ID NO 4
<211> LENGTH: 20
<212> TYPE: PRT
<213> ORGANISM: Homo sapiens

<400> SEQUENCE: 4

Ser Asn Lys Thr Arg Ile Asp Glu Ala Asn Gln Arg Ala Thr Lys Met
1               5                   10                  15

Leu Gly Ser Gly
            20

<210> SEQ ID NO 5
<211> LENGTH: 16
<212> TYPE: PRT
<213> ORGANISM: Homo sapiens

<400> SEQUENCE: 5

Gln Asn Arg Gln Ile Asp Arg Ile Met Glu Lys Ala Asp Ser Asn Lys
```

<210> SEQ ID NO 6
<211> LENGTH: 6
<212> TYPE: PRT
<213> ORGANISM: Artificial Sequence
<220> FEATURE:
<223> OTHER INFORMATION: Synthesized peptide

<400> SEQUENCE: 6

```
Glu Glu Met Gln Arg Arg
1               5
```

<210> SEQ ID NO 7
<211> LENGTH: 13
<212> TYPE: PRT
<213> ORGANISM: Artificial Sequence
<220> FEATURE:
<223> OTHER INFORMATION: Synthetic peptide

<400> SEQUENCE: 7

```
Glu Leu Glu Glu Met Gln Arg Arg Ala Asp Gln Leu Ala
1               5                   10
```

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: X is any amino acid or absent

<400> SEQUENCE: 8

```
Xaa Ile Lys Val Ala Val
1               5
```

<210> SEQ ID NO 9
<211> LENGTH: 205
<212> TYPE: PRT
<213> ORGANISM: Homo sapiens

<400> SEQUENCE: 9

```
Met Ala Glu Asp Ala Asp Met Arg Asn Glu Leu Glu Glu Met Gln Arg
1               5                   10                  15

Ala Asp Gln Leu Ala Asp Glu Ser Leu Glu Ser Thr Arg Arg Met Leu
            20                  25                  30

Gln Leu Val Glu Glu Ser Lys Asp Ala Gly Ile Arg Thr Leu Val Met
        35                  40                  45

Leu Asp Glu Gln Gly Glu Gln Leu Glu Arg Ile Glu Glu Gly Met Asp
    50                  55                  60

Gln Ile Asn Lys Asp Met Lys Glu Ala Glu Lys Asn Leu Thr Asp Leu
65                  70                  75                  80

Gly Lys Phe Cys Gly Leu Cys Val Cys Pro Cys Asn Leu Leu Lys Ser
                85                  90                  95

Ser Asp Ala Tyr Lys Lys Ala Trp Gly Asn Asn Gln Asp Gly Val Val
            100                 105                 110

Ala Ser Gln Pro Ala Arg Val Val Asp Glu Arg Glu Gln Met Ala Ile
        115                 120                 125

Ser Gly Gly Phe Ile Arg Arg Val Thr Asn Asp Ala Arg Glu Asn Glu
    130                 135                 140
```

-continued

Met Asp Glu Asn Leu Glu Gln Val Ser Gly Ile Ile Gly Asn Leu Arg
145                 150                 155                 160

His Met Ala Leu Asp Met Gly Asn Glu Ile Asp Thr Gln Asn Arg Gln
            165                 170                 175

Ile Asp Arg Ile Met Glu Lys Ala Asp Ser Asn Lys Thr Arg Ile Asp
        180                 185                 190

Glu Ala Asn Gln Arg Ala Thr Lys Met Leu Gly Ser Gly
        195                 200                 205

<210> SEQ ID NO 10
<211> LENGTH: 21
<212> TYPE: PRT
<213> ORGANISM: Homo sapiens

<400> SEQUENCE: 10

Met Ala Glu Asp Ala Asp Met Arg Asn Glu Leu Glu Glu Met Gln Arg
1               5                   10                  15

Arg Ala Asp Gln Leu
            20

<210> SEQ ID NO 11
<211> LENGTH: 23
<212> TYPE: PRT
<213> ORGANISM: Homo sapiens

<400> SEQUENCE: 11

Ala Asp Glu Ser Leu Glu Ser Thr Arg Arg Met Leu Gln Leu Val Glu
1               5                   10                  15

Glu Ser Lys Asp Ala Gly Ile
            20

<210> SEQ ID NO 12
<211> LENGTH: 13
<212> TYPE: PRT
<213> ORGANISM: Homo sapiens

<400> SEQUENCE: 12

Glu Leu Glu Glu Met Gln Arg Arg Ala Asp Gln Leu Ala
1               5                   10

<210> SEQ ID NO 13
<211> LENGTH: 12
<212> TYPE: PRT
<213> ORGANISM: Homo sapiens

<400> SEQUENCE: 13

Glu Leu Glu Glu Met Gln Arg Arg Ala Asp Gln Leu
1               5                   10

<210> SEQ ID NO 14
<211> LENGTH: 11
<212> TYPE: PRT
<213> ORGANISM: Homo sapiens

<400> SEQUENCE: 14

Glu Leu Glu Glu Met Gln Arg Arg Ala Asp Gln
1               5                   10

<210> SEQ ID NO 15
<211> LENGTH: 10
<212> TYPE: PRT
<213> ORGANISM: Homo sapiens

```
<400> SEQUENCE: 15

Glu Leu Glu Glu Met Gln Arg Arg Ala Asp
1               5                   10

<210> SEQ ID NO 16
<211> LENGTH: 9
<212> TYPE: PRT
<213> ORGANISM: Homo sapiens

<400> SEQUENCE: 16

Glu Leu Glu Glu Met Gln Arg Arg Ala
1               5

<210> SEQ ID NO 17
<211> LENGTH: 8
<212> TYPE: PRT
<213> ORGANISM: Homo sapiens

<400> SEQUENCE: 17

Glu Leu Glu Glu Met Gln Arg Arg
1               5

<210> SEQ ID NO 18
<211> LENGTH: 11
<212> TYPE: PRT
<213> ORGANISM: Homo sapiens

<400> SEQUENCE: 18

Leu Glu Glu Met Gln Arg Arg Ala Asp Gln Leu
1               5                   10

<210> SEQ ID NO 19
<211> LENGTH: 10
<212> TYPE: PRT
<213> ORGANISM: Homo sapiens

<400> SEQUENCE: 19

Leu Glu Glu Met Gln Arg Arg Ala Asp Gln
1               5                   10

<210> SEQ ID NO 20
<211> LENGTH: 9
<212> TYPE: PRT
<213> ORGANISM: Homo sapiens

<400> SEQUENCE: 20

Leu Glu Glu Met Gln Arg Arg Ala Asp
1               5

<210> SEQ ID NO 21
<211> LENGTH: 8
<212> TYPE: PRT
<213> ORGANISM: Homo sapiens

<400> SEQUENCE: 21

Leu Glu Glu Met Gln Arg Arg Ala
1               5

<210> SEQ ID NO 22
<211> LENGTH: 7
<212> TYPE: PRT
<213> ORGANISM: Homo sapiens

<400> SEQUENCE: 22
```

```
Leu Glu Glu Met Gln Arg Arg
1               5

<210> SEQ ID NO 23
<211> LENGTH: 10
<212> TYPE: PRT
<213> ORGANISM: Homo sapiens

<400> SEQUENCE: 23

Glu Glu Met Gln Arg Arg Ala Asp Gln Leu
1               5                   10

<210> SEQ ID NO 24
<211> LENGTH: 9
<212> TYPE: PRT
<213> ORGANISM: Homo sapiens

<400> SEQUENCE: 24

Glu Glu Met Gln Arg Arg Ala Asp Gln
1               5

<210> SEQ ID NO 25
<211> LENGTH: 8
<212> TYPE: PRT
<213> ORGANISM: Homo sapiens

<400> SEQUENCE: 25

Glu Glu Met Gln Arg Arg Ala Asp
1               5

<210> SEQ ID NO 26
<211> LENGTH: 7
<212> TYPE: PRT
<213> ORGANISM: Homo sapiens

<400> SEQUENCE: 26

Glu Glu Met Gln Arg Arg Ala
1               5

<210> SEQ ID NO 27
<211> LENGTH: 6
<212> TYPE: PRT
<213> ORGANISM: Homo sapiens

<400> SEQUENCE: 27

Glu Glu Met Gln Arg Arg
1               5

<210> SEQ ID NO 28
<211> LENGTH: 13
<212> TYPE: PRT
<213> ORGANISM: Homo sapiens

<400> SEQUENCE: 28

Leu Glu Ser Thr Arg Arg Met Leu Gln Leu Val Glu Glu
1               5                   10

<210> SEQ ID NO 29
<211> LENGTH: 12
<212> TYPE: PRT
<213> ORGANISM: Homo sapiens

<400> SEQUENCE: 29

Asn Lys Asp Met Lys Glu Ala Glu Lys Asn Leu Thr
```

```
1               5                   10
```

<210> SEQ ID NO 30
<211> LENGTH: 6
<212> TYPE: PRT
<213> ORGANISM: Homo sapiens

<400> SEQUENCE: 30

```
Lys Asn Leu Thr Asp Leu
1               5
```

<210> SEQ ID NO 31
<211> LENGTH: 26
<212> TYPE: PRT
<213> ORGANISM: Homo sapiens

<400> SEQUENCE: 31

```
Ile Met Glu Lys Ala Asp Ser Asn Lys Thr Arg Ile Asp Glu Ala Asp
1               5                   10                  15

Gln Arg Ala Thr Lys Met Leu Gly Ser Gly
            20                  25
```

<210> SEQ ID NO 32
<211> LENGTH: 20
<212> TYPE: PRT
<213> ORGANISM: Homo sapiens

<400> SEQUENCE: 32

```
Ser Asn Lys Thr Arg Ile Asp Glu Ala Asn Gln Arg Ala Thr Lys Met
1               5                   10                  15

Leu Gly Ser Gly
            20
```

<210> SEQ ID NO 33
<211> LENGTH: 17
<212> TYPE: PRT
<213> ORGANISM: Homo sapiens

<400> SEQUENCE: 33

```
Thr Arg Ile Asp Glu Ala Asn Gln Arg Ala Thr Lys Met Leu Gly Ser
1               5                   10                  15

Gly
```

<210> SEQ ID NO 34
<211> LENGTH: 14
<212> TYPE: PRT
<213> ORGANISM: Homo sapiens

<400> SEQUENCE: 34

```
Asp Glu Ala Asn Gln Arg Ala Thr Lys Met Leu Gly Ser Gly
1               5                   10
```

<210> SEQ ID NO 35
<211> LENGTH: 11
<212> TYPE: PRT
<213> ORGANISM: Homo sapiens

<400> SEQUENCE: 35

```
Asn Gln Arg Ala Thr Lys Met Leu Gly Ser Gly
1               5                   10
```

<210> SEQ ID NO 36
<211> LENGTH: 10

```
<212> TYPE: PRT
<213> ORGANISM: Homo sapiens

<400> SEQUENCE: 36

Gln Arg Ala Thr Lys Met Leu Gly Ser Gly
1               5                   10

<210> SEQ ID NO 37
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: X at  2 is His or Asn
<220> FEATURE:
<221> NAME/KEY: misc_feature
<222> LOCATION: (3)..(3)
<223> OTHER INFORMATION: X at  3 is His or Arg
<220> FEATURE:
<221> NAME/KEY: misc_feature
<222> LOCATION: (4)..(4)
<223> OTHER INFORMATION: X at  4 is Cit

<400> SEQUENCE: 37

Arg Xaa Xaa Xaa
1

<210> SEQ ID NO 38
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: X at 4 is Cit

<400> SEQUENCE: 38

Arg His His Xaa
1

<210> SEQ ID NO 39
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: X is Cit

<400> SEQUENCE: 39

Arg Asn Arg Xaa
1

<210> SEQ ID NO 40
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X at 1 is Lys, Orn, Dab, Dpr, Agl,
      3,4-dehydrolysine, or 4,5-dehydrolysine
```

```
<220> FEATURE:
<221> NAME/KEY: misc_feature
<222> LOCATION: (2)..(2)
<223> OTHER INFORMATION: X at 2 is Ala
<220> FEATURE:
<221> NAME/KEY: misc_feature
<222> LOCATION: (3)..(3)
<223> OTHER INFORMATION: X at 3 is Asp, Ala, Asn, Glu, or Pro
<220> FEATURE:
<221> NAME/KEY: misc_feature
<222> LOCATION: (4)..(4)
<223> OTHER INFORMATION: X at 4 is His

<400> SEQUENCE: 40

Xaa Xaa Xaa Xaa
1

<210> SEQ ID NO 41
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X at 1 is L-Dpr
<220> FEATURE:
<221> NAME/KEY: misc_feature
<222> LOCATION: (2)..(2)
<223> OTHER INFORMATION: X at 2 is D-Ala
<220> FEATURE:
<221> NAME/KEY: misc_feature
<222> LOCATION: (3)..(3)
<223> OTHER INFORMATION: X at 3 is L-Ala
<220> FEATURE:
<221> NAME/KEY: misc_feature
<222> LOCATION: (4)..(4)
<223> OTHER INFORMATION: X at 4 is L-His

<400> SEQUENCE: 41

Xaa Xaa Xaa Xaa
1

<210> SEQ ID NO 42
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X at 1 is L-Dpr
<220> FEATURE:
<221> NAME/KEY: misc_feature
<222> LOCATION: (2)..(2)
<223> OTHER INFORMATION: X at 2 is D-Ala
<220> FEATURE:
<221> NAME/KEY: misc_feature
<222> LOCATION: (3)..(3)
<223> OTHER INFORMATION: X at 3 is L-Pro
<220> FEATURE:
<221> NAME/KEY: misc_feature
<222> LOCATION: (4)..(4)
<223> OTHER INFORMATION: X at 4 is L-His

<400> SEQUENCE: 42

Xaa Xaa Xaa Xaa
1

<210> SEQ ID NO 43
<211> LENGTH: 4
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X at 1 is L-Dpr
<220> FEATURE:
<221> NAME/KEY: misc_feature
<222> LOCATION: (2)..(2)
<223> OTHER INFORMATION: X at 2 is L-Ala
<220> FEATURE:
<221> NAME/KEY: misc_feature
<222> LOCATION: (3)..(3)
<223> OTHER INFORMATION: X at 3 is L-Pro
<220> FEATURE:
<221> NAME/KEY: misc_feature
<222> LOCATION: (4)..(4)
<223> OTHER INFORMATION: X at 4 is L-His

<400> SEQUENCE: 43

Xaa Xaa Xaa Xaa
1

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X at 1 is any amino acid or is absent
<220> FEATURE:
<221> NAME/KEY: misc_feature
<222> LOCATION: (2)..(2)
<223> OTHER INFORMATION: X at 2 is any amino acid or is absent
<220> FEATURE:
<221> NAME/KEY: misc_feature
<222> LOCATION: (3)..(3)
<223> OTHER INFORMATION: X at 3 is Arg, Phg, Nle, or absent
<220> FEATURE:
<221> NAME/KEY: misc_feature
<222> LOCATION: (4)..(4)
<223> OTHER INFORMATION: X at 4 is Ala, Phg, Cit, or Nle
<220> FEATURE:
<221> NAME/KEY: misc_feature
<222> LOCATION: (5)..(5)
<223> OTHER INFORMATION: X at 5 is Trp, Val, or Tyr
<220> FEATURE:
<221> NAME/KEY: misc_feature
<222> LOCATION: (6)..(6)
<223> OTHER INFORMATION: X at 6 is Phg or Gly
<220> FEATURE:
<221> NAME/KEY: misc_feature
<222> LOCATION: (7)..(7)
<223> OTHER INFORMATION: X at 7 is any amino acid or absent

<400> SEQUENCE: 44

Xaa Xaa Xaa Xaa Xaa Xaa Xaa
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: X at 1 is L-Arg
<220> FEATURE:
```

```
<221> NAME/KEY: misc_feature
<222> LOCATION: (2)..(2)
<223> OTHER INFORMATION: X at 2 is L-Nle
<220> FEATURE:
<221> NAME/KEY: misc_feature
<222> LOCATION: (3)..(3)
<223> OTHER INFORMATION: X at 3 is L-Phg or D-Phg
<220> FEATURE:
<221> NAME/KEY: misc_feature
<222> LOCATION: (4)..(4)
<223> OTHER INFORMATION: X at 4 is L-Tyr
<220> FEATURE:
<221> NAME/KEY: misc_feature
<222> LOCATION: (5)..(5)
<223> OTHER INFORMATION: X at 5 is L-Phg or D-Phg

<400> SEQUENCE: 45

Xaa Xaa Xaa Xaa Xaa
1               5

<210> SEQ ID NO 46
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X at 1 is L-Arg, L-Nle, or absent
<220> FEATURE:
<221> NAME/KEY: misc_feature
<222> LOCATION: (2)..(2)
<223> OTHER INFORMATION: X at 2 is L-Phg or D-Phg
<220> FEATURE:
<221> NAME/KEY: misc_feature
<222> LOCATION: (3)..(3)
<223> OTHER INFORMATION: X at 3 is L-Tyr
<220> FEATURE:
<221> NAME/KEY: misc_feature
<222> LOCATION: (4)..(4)
<223> OTHER INFORMATION: X at 4 is L-Phg or D-Phg

<400> SEQUENCE: 46

Xaa Xaa Xaa Xaa
1

<210> SEQ ID NO 47
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X at 1 is L-Arg
<220> FEATURE:
<221> NAME/KEY: misc_feature
<222> LOCATION: (2)..(2)
<223> OTHER INFORMATION: X at 2 is L-Phg or D-Phg
<220> FEATURE:
<221> NAME/KEY: misc_feature
<222> LOCATION: (3)..(3)
<223> OTHER INFORMATION: X at 3 is L-Val
<220> FEATURE:
<221> NAME/KEY: misc_feature
<222> LOCATION: (4)..(4)
<223> OTHER INFORMATION: X at 4 is L-Phg, D-Phg, or L-Gly

<400> SEQUENCE: 47

Xaa Xaa Xaa Xaa
1
```

```
<210> SEQ ID NO 48
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X at 1 is L-Phg or D-Phg
<220> FEATURE:
<221> NAME/KEY: misc_feature
<222> LOCATION: (2)..(2)
<223> OTHER INFORMATION: X at 2 is L-Phg or D-Phg
<220> FEATURE:
<221> NAME/KEY: misc_feature
<222> LOCATION: (3)..(3)
<223> OTHER INFORMATION: X at 3 is L-Trp
<220> FEATURE:
<221> NAME/KEY: misc_feature
<222> LOCATION: (4)..(4)
<223> OTHER INFORMATION: X at 4 is L-Phg or D-Phg

<400> SEQUENCE: 48

Xaa Xaa Xaa Xaa
1

<210> SEQ ID NO 49
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: X at 1 is any amino acid or absent
<220> FEATURE:
<221> NAME/KEY: misc_feature
<222> LOCATION: (2)..(2)
<223> OTHER INFORMATION: X at 2 is any amino acid or absent
<220> FEATURE:
<221> NAME/KEY: misc_feature
<222> LOCATION: (3)..(3)
<223> OTHER INFORMATION: X at 3 is Asp, Glu, or Pro
<220> FEATURE:
<221> NAME/KEY: misc_feature
<222> LOCATION: (4)..(4)
<223> OTHER INFORMATION: X at 4 is Asp
<220> FEATURE:
<221> NAME/KEY: misc_feature
<222> LOCATION: (5)..(5)
<223> OTHER INFORMATION: X at 5 is Tyr or Arg
<220> FEATURE:
<221> NAME/KEY: misc_feature
<222> LOCATION: (6)..(6)
<223> OTHER INFORMATION: X at 6 is Phe or Tyr
<220> FEATURE:
<221> NAME/KEY: misc_feature
<222> LOCATION: (7)..(7)
<223> OTHER INFORMATION: X at 7 is Arg or Lys
<220> FEATURE:
<221> NAME/KEY: misc_feature
<222> LOCATION: (8)..(8)
<223> OTHER INFORMATION: X at 8 is Leu or Met
<220> FEATURE:
<221> NAME/KEY: misc_feature
<222> LOCATION: (9)..(9)
<223> OTHER INFORMATION: X at 9 is any amino acid or absent
<220> FEATURE:
<221> NAME/KEY: misc_feature
<222> LOCATION: (10)..(10)
<223> OTHER INFORMATION: X at 10 is any amino acid or absent

<400> SEQUENCE: 49
```

Xaa Xaa Xaa Xaa Xaa Xaa Xaa Xaa Xaa Xaa
1               5                   10

<210> SEQ ID NO 50
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: X is L-Glu
<220> FEATURE:
<221> NAME/KEY: misc_feature
<222> LOCATION: (2)..(2)
<223> OTHER INFORMATION: X is L-Asp
<220> FEATURE:
<221> NAME/KEY: misc_feature
<222> LOCATION: (3)..(3)
<223> OTHER INFORMATION: X is L-Tyr
<220> FEATURE:
<221> NAME/KEY: misc_feature
<222> LOCATION: (4)..(4)
<223> OTHER INFORMATION: X is L-Tyr
<220> FEATURE:
<221> NAME/KEY: misc_feature
<222> LOCATION: (5)..(5)
<223> OTHER INFORMATION: X is L-Arg
<220> FEATURE:
<221> NAME/KEY: misc_feature
<222> LOCATION: (6)..(6)
<223> OTHER INFORMATION: X is L-Leu

<400> SEQUENCE: 50

Xaa Xaa Xaa Xaa Xaa Xaa
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X is L-Pro
<220> FEATURE:
<221> NAME/KEY: misc_feature
<222> LOCATION: (2)..(2)
<223> OTHER INFORMATION: X is L-Asp
<220> FEATURE:
<221> NAME/KEY: misc_feature
<222> LOCATION: (3)..(3)
<223> OTHER INFORMATION: X is L-Tyr
<220> FEATURE:
<221> NAME/KEY: misc_feature
<222> LOCATION: (4)..(4)
<223> OTHER INFORMATION: X is L-Tyr
<220> FEATURE:
<221> NAME/KEY: misc_feature
<222> LOCATION: (5)..(5)
<223> OTHER INFORMATION: X is L-Lys
<220> FEATURE:
<221> NAME/KEY: misc_feature
<222> LOCATION: (6)..(6)
<223> OTHER INFORMATION: X is L-Leu

<400> SEQUENCE: 51

Xaa Xaa Xaa Xaa Xaa Xaa
1               5

<210> SEQ ID NO 52

```
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X is L-Glu
<220> FEATURE:
<221> NAME/KEY: misc_feature
<222> LOCATION: (2)..(2)
<223> OTHER INFORMATION: X is L-Asp
<220> FEATURE:
<221> NAME/KEY: misc_feature
<222> LOCATION: (3)..(3)
<223> OTHER INFORMATION: X is L-Arg
<220> FEATURE:
<221> NAME/KEY: misc_feature
<222> LOCATION: (4)..(4)
<223> OTHER INFORMATION: X is L-Phe
<220> FEATURE:
<221> NAME/KEY: misc_feature
<222> LOCATION: (5)..(5)
<223> OTHER INFORMATION: X is L-Arg
<220> FEATURE:
<221> NAME/KEY: misc_feature
<222> LOCATION: (6)..(6)
<223> OTHER INFORMATION: X is L-Met

<400> SEQUENCE: 52

Xaa Xaa Xaa Xaa Xaa Xaa
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X is L-Glu
<220> FEATURE:
<221> NAME/KEY: misc_feature
<222> LOCATION: (2)..(2)
<223> OTHER INFORMATION: X is L-Asp
<220> FEATURE:
<221> NAME/KEY: misc_feature
<222> LOCATION: (3)..(3)
<223> OTHER INFORMATION: X is L-Tyr
<220> FEATURE:
<221> NAME/KEY: misc_feature
<222> LOCATION: (4)..(4)
<223> OTHER INFORMATION: X is L-Tyr
<220> FEATURE:
<221> NAME/KEY: misc_feature
<222> LOCATION: (5)..(5)
<223> OTHER INFORMATION: X is L-Arg
<220> FEATURE:
<221> NAME/KEY: misc_feature
<222> LOCATION: (6)..(6)
<223> OTHER INFORMATION: X is L-Met

<400> SEQUENCE: 53

Xaa Xaa Xaa Xaa Xaa Xaa
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: misc_feature
<222> LOCATION: (1)..(1)
<223> OTHER INFORMATION: X is L-Pro
<220> FEATURE:
<221> NAME/KEY: misc_feature
<222> LOCATION: (2)..(2)
<223> OTHER INFORMATION: X is L-Asp
<220> FEATURE:
<221> NAME/KEY: misc_feature
<222> LOCATION: (3)..(3)
<223> OTHER INFORMATION: X is L-Tyr
<220> FEATURE:
<221> NAME/KEY: misc_feature
<222> LOCATION: (4)..(4)
<223> OTHER INFORMATION: X is L-Tyr
<220> FEATURE:
<221> NAME/KEY: misc_feature
<222> LOCATION: (5)..(5)
<223> OTHER INFORMATION: X is L-Arg
<220> FEATURE:
<221> NAME/KEY: misc_feature
<222> LOCATION: (6)..(6)
<223> OTHER INFORMATION: X is L-Met

<400> SEQUENCE: 54

Xaa Xaa Xaa Xaa Xaa Xaa
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic pepride
<220> FEATURE:
<221> NAME/KEY: misc_feature
<222> LOCATION: (1)..(1)
<223> OTHER INFORMATION: X is any amino acid or absent
<220> FEATURE:
<221> NAME/KEY: misc_feature
<222> LOCATION: (2)..(2)
<223> OTHER INFORMATION: X is any amino acid or absent
<220> FEATURE:
<221> NAME/KEY: misc_feature
<222> LOCATION: (4)..(4)
<223> OTHER INFORMATION: X is His, Leu, or Pro
<220> FEATURE:
<221> NAME/KEY: misc_feature
<222> LOCATION: (6)..(6)
<223> OTHER INFORMATION: X is Arg or Asn
<220> FEATURE:
<221> NAME/KEY: misc_feature
<222> LOCATION: (7)..(7)
<223> OTHER INFORMATION: X is any amino acid or absent
<220> FEATURE:
<221> NAME/KEY: misc_feature
<222> LOCATION: (8)..(8)
<223> OTHER INFORMATION: X is any amino acid or absent

<400> SEQUENCE: 55

Xaa Xaa His Xaa Leu Xaa Xaa Xaa
1               5

<210> SEQ ID NO 56
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X is L-His
<220> FEATURE:
```

```
<221> NAME/KEY: misc_feature
<222> LOCATION: (2)..(2)
<223> OTHER INFORMATION: X is L-Leu
<220> FEATURE:
<221> NAME/KEY: misc_feature
<222> LOCATION: (3)..(3)
<223> OTHER INFORMATION: X is L-Leu
<220> FEATURE:
<221> NAME/KEY: misc_feature
<222> LOCATION: (4)..(4)
<223> OTHER INFORMATION: X is L-Arg

<400> SEQUENCE: 56

Xaa Xaa Xaa Xaa
1

<210> SEQ ID NO 57
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X is L-His
<220> FEATURE:
<221> NAME/KEY: misc_feature
<222> LOCATION: (2)..(2)
<223> OTHER INFORMATION: X is L-Pro
<220> FEATURE:
<221> NAME/KEY: misc_feature
<222> LOCATION: (3)..(3)
<223> OTHER INFORMATION: X is L-Leu
<220> FEATURE:
<221> NAME/KEY: misc_feature
<222> LOCATION: (4)..(4)
<223> OTHER INFORMATION: X is L-Arg

<400> SEQUENCE: 57

Xaa Xaa Xaa Xaa
1

<210> SEQ ID NO 58
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X is any amino acid or absent
<220> FEATURE:
<221> NAME/KEY: misc_feature
<222> LOCATION: (2)..(2)
<223> OTHER INFORMATION: X is any amino acid or absent
<220> FEATURE:
<221> NAME/KEY: misc_feature
<222> LOCATION: (3)..(3)
<223> OTHER INFORMATION: X is Ser, Thr, or Tyr
<220> FEATURE:
<221> NAME/KEY: misc_feature
<222> LOCATION: (4)..(4)
<223> OTHER INFORMATION: X is Pro or Val
<220> FEATURE:
<221> NAME/KEY: misc_feature
<222> LOCATION: (6)..(6)
<223> OTHER INFORMATION: X is Glu, Gly, or Val
<220> FEATURE:
<221> NAME/KEY: misc_feature
<222> LOCATION: (8)..(8)
<223> OTHER INFORMATION: X is Gln, Gly, His, or Pro
<220> FEATURE:
<221> NAME/KEY: misc_feature
```

```
<222> LOCATION: (9)..(9)
<223> OTHER INFORMATION: X any amino acid or absent
<220> FEATURE:
<221> NAME/KEY: misc_feature
<222> LOCATION: (10)..(10)
<223> OTHER INFORMATION: X any amino acid or absent

<400> SEQUENCE: 58

Xaa Xaa Xaa Xaa Ala Xaa Gly Xaa Xaa Xaa
1               5                   10

<210> SEQ ID NO 59
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X is L-Tyr
<220> FEATURE:
<221> NAME/KEY: misc_feature
<222> LOCATION: (2)..(2)
<223> OTHER INFORMATION: X is L-Pro
<220> FEATURE:
<221> NAME/KEY: misc_feature
<222> LOCATION: (3)..(3)
<223> OTHER INFORMATION: X is L-Ala
<220> FEATURE:
<221> NAME/KEY: misc_feature
<222> LOCATION: (4)..(4)
<223> OTHER INFORMATION: X is L-Glu
<220> FEATURE:
<221> NAME/KEY: misc_feature
<222> LOCATION: (5)..(5)
<223> OTHER INFORMATION: X is L-Gly
<220> FEATURE:
<221> NAME/KEY: misc_feature
<222> LOCATION: (6)..(6)
<223> OTHER INFORMATION: X is L-Gln

<400> SEQUENCE: 59

Xaa Xaa Xaa Xaa Xaa Xaa
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X is L-Ser
<220> FEATURE:
<221> NAME/KEY: misc_feature
<222> LOCATION: (2)..(2)
<223> OTHER INFORMATION: X is L-Val
<220> FEATURE:
<221> NAME/KEY: misc_feature
<222> LOCATION: (3)..(3)
<223> OTHER INFORMATION: X is L-Ala
<220> FEATURE:
<221> NAME/KEY: misc_feature
<222> LOCATION: (4)..(4)
<223> OTHER INFORMATION: X is L-Val
<220> FEATURE:
<221> NAME/KEY: misc_feature
<222> LOCATION: (5)..(5)
<223> OTHER INFORMATION: X is L-Gly
<220> FEATURE:
<221> NAME/KEY: misc_feature
<222> LOCATION: (6)..(6)
```

<223> OTHER INFORMATION: X is L-Gln

<400> SEQUENCE: 60

Xaa Xaa Xaa Xaa Xaa Xaa
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X is L-Ser
<220> FEATURE:
<221> NAME/KEY: misc_feature
<222> LOCATION: (2)..(2)
<223> OTHER INFORMATION: X is L-Pro
<220> FEATURE:
<221> NAME/KEY: misc_feature
<222> LOCATION: (3)..(3)
<223> OTHER INFORMATION: X is L-Ala
<220> FEATURE:
<221> NAME/KEY: misc_feature
<222> LOCATION: (4)..(4)
<223> OTHER INFORMATION: X is L-Gly
<220> FEATURE:
<221> NAME/KEY: misc_feature
<222> LOCATION: (5)..(5)
<223> OTHER INFORMATION: X is L-Gly
<220> FEATURE:
<221> NAME/KEY: misc_feature
<222> LOCATION: (6)..(6)
<223> OTHER INFORMATION: X is L-Pro

<400> SEQUENCE: 61

Xaa Xaa Xaa Xaa Xaa Xaa
1               5

<210> SEQ ID NO 62
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X is any amino acid or absent
<220> FEATURE:
<221> NAME/KEY: misc_feature
<222> LOCATION: (2)..(2)
<223> OTHER INFORMATION: X is any amino acid or absent
<220> FEATURE:
<221> NAME/KEY: misc_feature
<222> LOCATION: (4)..(4)
<223> OTHER INFORMATION: X is Asn, His, Tyr, or Glu
<220> FEATURE:
<221> NAME/KEY: misc_feature
<222> LOCATION: (5)..(5)
<223> OTHER INFORMATION: X is Lys, Ser, or Pro
<220> FEATURE:
<221> NAME/KEY: misc_feature
<222> LOCATION: (6)..(6)
<223> OTHER INFORMATION: X is Gly, Leu, Lys, or His
<220> FEATURE:
<221> NAME/KEY: misc_feature
<222> LOCATION: (7)..(7)
<223> OTHER INFORMATION: X is Gln or Asn
<220> FEATURE:
<221> NAME/KEY: misc_feature
<222> LOCATION: (9)..(9)
<223> OTHER INFORMATION: X is any amino acid or absent

```
<220> FEATURE:
<221> NAME/KEY: misc_feature
<222> LOCATION: (10)..(10)
<223> OTHER INFORMATION: X is any amino acid or absent

<400> SEQUENCE: 62

Xaa Xaa Tyr Xaa Xaa Xaa Xaa Val Xaa Xaa
1               5                   10
```

THERMOPLASTIC POLYURETHANE FILM FOR DELIVERY OF ACTIVE AGENTS TO SKIN SURFACES

This application claims the priority of PCT/US2015/057084 (WO 2016/069396), filed Oct. 23, 2015, U.S. Provisional Application Ser. No. 62/073,314, filed Oct. 31, 2014, and U.S. Provisional Application Ser. No. 62/220,552, filed Sep. 18, 2015, from which the PCT application claims priority, the disclosure of each of which is hereby incorporated by reference in its entirety.

BACKGROUND

The exemplary embodiment relates to the delivery of active agents to skin surfaces and finds particular application in connection with a thermoplastic polyurethane film that serves as a vehicle for skin treatment active agents and a face mask or body patch formed from the film.

Face masks have been traditionally used for providing active agents to the face and other skin surfaces. The active agents may include vitamins, moisturizers, cleansers, anti-wrinkle agents, lightening agents, skin toning agents, and others.

Conventional face masks include hydrocolloid layers containing the active agents and other nutrients. The hydrocolloid layers are often held together by fabric or a synthetic mesh which provides a physical and mechanical support. Such multi-layered face masks tend to be time consuming and costly to manufacture. Hydrocolloid face masks are typically formed by hot solution casting of a mixture of polysaccharide polymers such as carrageenan, locust bean gum (galactomannans), agarose, agar, and xanthan gum. Generally the polysaccharide components are added to a mixture of water, glycerin, and polypropylene glycol and heated to approximately 80 to 90° C. to dissolve the polymer and obtain a molten state. The colloid solution is cooled to about 60° C. and the cosmetic additives are added. This intermediate cooling step is to avoid harming temperature-sensitive active agents. The thickened solution is cast as a film with a knife at a set thickness. A rayon reinforcing material may be added. The solution is then cooled to 25° C. and kept between release films until the film sets to a firm gel before cutting to shape. The final gel film thickness is between 0.7 and 0.8 mm for hydrocolloid masks that are not reinforced and about 0.5 mm for reinforced masks.

Hydrocolloid face masks are also often opaque and slippery. This requires the subject being treated to lie down while the face mask is being applied and remain in this position for a treatment period of typically 30-60 minutes. Even if the subject is able to sit or stand, the face mask is very noticeable.

There remains a need for a face mask material with transparency, flexibility, strength and ability to adhere to the skin while the subject is in an upright position, which is able to deliver active agents to the skin and that would enable the subject to walk around and perform other activities while still continuing with the facial treatment. Additionally, the face mask material should not leave behind a residue the skin once it is removed so that there is no need to wash the face unless the skin treatment is to be removed. It would also be advantageous to be able to use cold processing techniques to form the face mask.

BRIEF DESCRIPTION

In accordance with one aspect of the exemplary embodiment, a polymer film includes at least 30 wt. % of a thermoplastic polyurethane polymer which is the reaction product of a first polyether polyol having a molecular weight of at least 3000 daltons, optionally, a second polyether polyol having a molecular weight of no more than 2500 daltons, at least one of a third polyol having a molecular weight of up to 800 daltons, and a chain extender, a diisocyanate, optionally, a catalyst; and up to 5 wt. % water.

In accordance with another aspect of the exemplary embodiment, a method of forming a face mask or body patch includes forming a thermoplastic polyurethane polymer from a first polyether polyol having a molecular weight of at least 3000 daltons, optionally, a second polyether polyol having a molecular weight of no more than 2500 daltons, and at least one of a third polyol having a molecular weight of up to 800 daltons and a chain extender. The method further includes casting the thermoplastic polyurethane polymer with an active agent in solution to form a cast film which includes the active agent dispersed in the thermoplastic polyurethane polymer.

In accordance with another aspect of the exemplary embodiment, a face mask or body patch includes a hydrated film which includes at least 50 wt. % water, 5 to 30 wt. % of a thermoplastic polyurethane polymer, and at least one active agent.

DETAILED DESCRIPTION

Aspects of the exemplary embodiment relate to a polymer film which includes a thermoplastic polyurethane polymer, suited to use as a face mask or body patch, which may include one or more actives and/or excipients. The polymer film is able to absorb a considerable quantity of water that may include the one or more actives and/or excipients.

Figure 1:
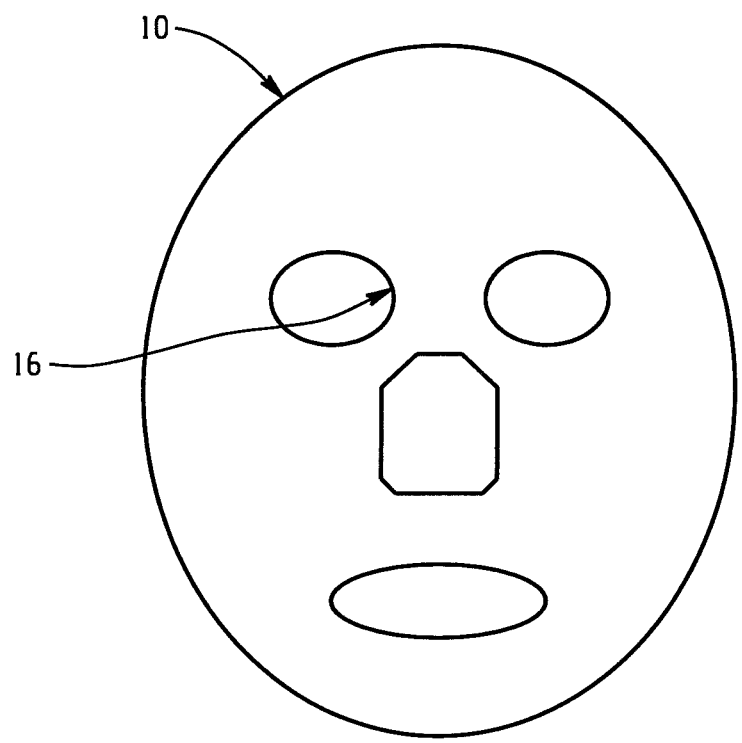
FIG. 1 is a schematic top plan view of a face mask.

With reference to FIG. 1, a cosmetic sheet facial mask (face mask) 10 suited to delivering an active agent 12 to a surface 14 of the skin of a person, such as the face, is shown. The illustrated face mask is contoured to fit the user's face, for example is generally oval in shape, or otherwise shaped to cover at least a part of a face of a wearer, and has apertures 16 appropriately positioned to align with the eyes, nose, and/or mouth of the person.

Figure 2:
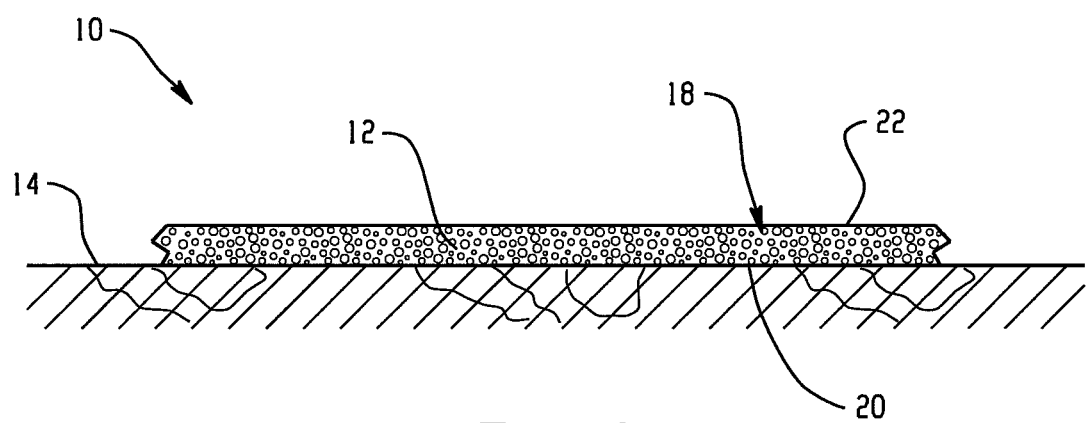
FIG. 2 is a side sectional view of a hydrated face mask on the skin of a wearer.

In one embodiment, shown in FIG. 2 (not to scale), the face mask 10 includes only a single water-insoluble film or layer 18 of a polyurethane material, having a first surface 20 and a second surface 22. In use, the first surface 20 contacts the surface 14 of the wearer's face while the second surface 22 is exposed to the atmosphere.

Figure 3:
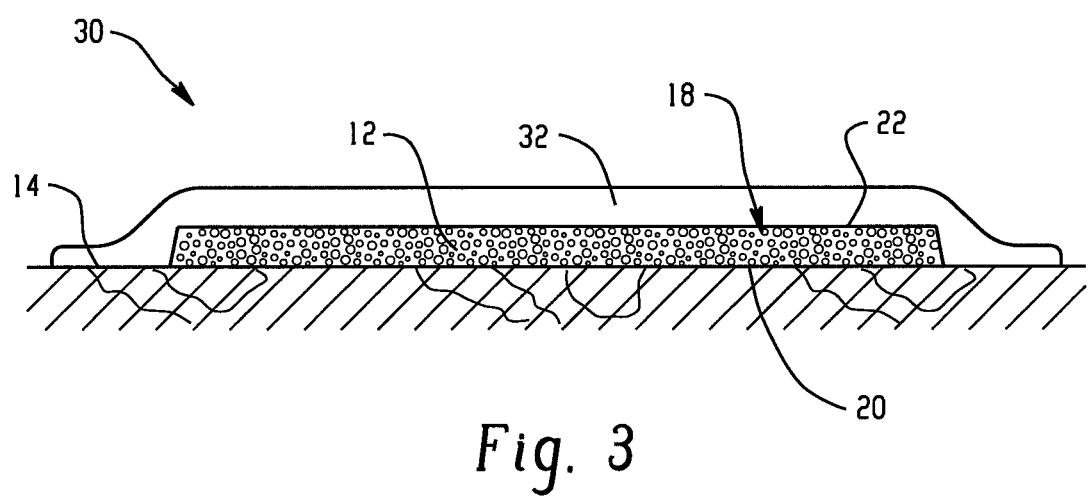
FIG. 3 illustrates a body patch.

FIG. 3 shows another embodiment, which suited to use as a body patch 30. In this embodiment, the film 18 may be at least partially covered, on the outer surface 22, by a second layer 32. The layer 32 may serve as one or more of: an adhesive for assisting in adhering the layer 18 to the skin; a moisture barrier to resist drying out of the hydrated film; and a sterile layer to avoid contamination of the film with dirt, microorganisms, or the like. In this embodiment, the adhesive layer 32 and film 18 may be stored separately until use, e.g., in separate sterile packages, or may be stored as a combination of film and adhesive layer. The layer 32, prior to use, may be covered by a removable liner material (not shown).

As will be appreciated, while the illustrated face mask/patch is formed as a single piece of film, a face mask may be formed from two or more pieces of the film, such as one piece covering an upper part of the wearer's face and one piece for covering a lower part, with a respective aperture or apertures in each part.

The polyurethane material of the film 18 includes a soft, flexible, clear thermoplastic polyurethane (TPU) or a blend of TPUs, which is extruded or solvent cast to form a thin film 18. The exemplary thin film 18 is water-swellable but is not soluble in water.

The dry polyurethane film 18 may have a thickness, prior to hydration, of at least 0.08 mm, or at least 0.1 mm, or at least 0.2 mm and can be up to 1 mm in thickness, or up to 0.6 mm, or up to 0.4 mm, or up to 0.35 mm.

A water content of the dry polyurethane film 18 (prior to hydration) may be less than 5 wt. %, or less than 2 wt. %, or less than 1 wt. %. The thin polyurethane film 18 has a high water pickup. For example, when soaked in an aqueous formulation (at least 50 wt. % water) at room temperature (defined herein as 22-26° C.) for a period of 30 minutes, the film may swell by at least 300 wt. % (2 g water/1 g polymer), or at least 500 wt. % (4 g water/1 g polymer), and in some embodiments, up to 2000 wt. % (19 g water/1 g polymer), or up to 1500 wt. % (14 g water/1 g polymer), or up to 1200 wt. % (10 g water/1 g polymer), or up to 1000 wt. % (9 g water/1 g polymer), while maintaining its integrity as a film.

While particular reference is made in the following to use of the film in a face mask, it is to be appreciated that a body patch is also contemplated.

The dry film 18 (or dry face mask 10 formed therefrom) may include at least 20 wt. % of thermoplastic polyurethane polymer as disclosed herein, or at least 30 wt. %, or at least 40 wt. %, or at least 50 wt. %, or at least 60 wt. %, or at least 70 wt. % of the thermoplastic polyurethane polymer, and in some embodiments up to 99.9 wt. %, or up to 99 wt. % of the thermoplastic polyurethane polymer, at room temperature. Polymers other than the thermoplastic polyurethane polymer disclosed herein which have a molecular weight of over 500 daltons may be present at up to 60 wt. %, or up to 50 wt. %, or up to 40 wt. %, or up to 20 wt. %, or up to 10 wt. % of the dry film.

One or more active agents may be present in the dry film/face mask in a pharmaceutically effective amount, i.e., an amount sufficient to have a beneficial effect on the skin. The amount of each active agent may thus vary, depending on the active agent being used. The one or more active agents may be present in the dry film/face mask at a total concentration of at least 0.00001 wt. %, or at least 0.0001 wt. %, or at least 0.001 wt. %, or at least 0.01 wt. %, or at least 0.1 wt. %, or at least 0.2 wt. %, or at least 0.4 wt. %, or at least 1 wt. %, or about 2 wt. %, and in some embodiments, up to 20 wt. %, or up to 18 wt. %, or up to 16 wt. %, or up to 10 wt. %, or up to 5 wt. %.

In one embodiment, the active agent includes at least one of a skin whitening or depigmenting agent and an anti-acne agent, or combinations thereof, which may be present at a concentration of at least 0.00001 wt. %, or at least 0.0001 wt. %, or at least 0.001 wt. %, or at least 0.01 wt. %, or at least 0.1 wt. %, or at least 0.5 wt. %, or at least 1 wt. % of the dry film, and in some embodiments, up to 10 wt. %, or up to 5 wt. %, or about 2 wt. %. The one or more active agents may be homogeneously incorporated/dispersed in the film/face mask, for example, by casting the film from a dispersion containing the TPU and active agent or by soaking the TPU in a hydrating solution containing the desired active agents and/or excipients.

One or more excipients may be present in the dry film/face mask at a total concentration of at least 0.01 wt. %, or at least 0.2 wt. %, or at least 0.4 wt. %, or at least 1 wt. %, and in some embodiments, up to 10 wt. %. The one or more excipients may be homogeneously dispersed in the film/face mask, for example, by casting the film from a dispersion containing the TPU and active agent and/or excipient.

The hydrated film 18 (or face mask 10 formed therefrom) after swelling in an aqueous formulation for at least 10 minutes, or 30 minutes, at room temperature, may be at least 0.2 or at least 0.5 mm in thickness and in some embodiments, is up to 1.5 mm, or up to 1.2 mm, or up to 1.0 mm, or up to 0.8 mm in thickness. The hydrated film/face mask may include at least 5 wt. % of thermoplastic polyurethane polymer, or at least 10 wt. % thereof, and in some embodiments up to 25 wt. %, or up to 20 wt. %, or up to 18 wt. %, or up to 10 wt. % of the thermoplastic polyurethane polymer at room temperature. Polymers other than thermoplastic polyurethane which have a molecular weight of over 500 daltons may be present at up to 10 wt. %, or up to 5 wt. %, or up to 1 wt. %, or as little as 0% of the hydrated film/face mask. The hydrated film/face mask may include at least 30 wt. % water, or at least 50 wt. % water.

One or more of the active agents may be present in the hydrated film/face mask in a pharmaceutically effective amount. For example, the active agents may be present at a total concentration of at least 0.00001 wt. %, or at least 0.001 wt. %, or at least 0.01 wt. %, or at least 0.1 wt. %, or at least 0.2 wt. %, or at least 0.5 wt. %, or at least 1 wt. %.

In one embodiment, the active agent includes a skin whitening or depigmenting agent, e.g., at a concentration of at least 0.00001 wt. %, or at least 0.1 wt. %, or at least 0.2 wt. % of the hydrated film/face mask. In one embodiment, the active agent includes an anti-acne agent, e.g., at a concentration of at least 0.1 wt. % or at least 0.2 wt. % of the hydrated film/face mask.

One or more excipients may be present in the hydrated film/face mask at a total concentration of at least 0.01 wt. %, or at least 0.1 wt. %, or at least 0.5 wt. %, or at least 1 wt. %, and in some embodiments, up to 50 wt. %.

A ratio by weight of the total amount of active agents to the exemplary thermoplastic polyurethane polymer in the dry film, hydrated film, and/or face mask may be at least 1:100,000, or at least 1:10,000 or at least 1:1000, or at least 1:200, or at least 1:100, or at least 1:50 and may be up to 1:5.

As an example, the hydrated film/face mask includes at least 5 wt. %, and/or up to 30 wt. %, or up to 20 wt. % of (what was) the dry film, at least one active agent at a total concentration of at least 0.0001 wt. %, or at least 0.001 wt. %, or at least 0.001 wt. %, or at least 0.01 wt. %, or at least 0.2 wt. %, optionally at least one excipient, and at least 30 wt. %, or at least 50 wt. %, or at least 60 wt. %, or at least 70 wt. %, or at least 80 wt. % water, and in some embodiments, up to 95% water or up to 90% water.

The hydrated film 18 and contoured face mask 10 formed therefrom are clear and flexible and have the ability to conform and adhere to the contours of the face and body. The hydrated film also has "drape" or "cling" type characteristics that enable them to hold on to the skin even when the face is in an upright position. The film is capable of maintaining film integrity over time, such as for at least 30 minutes or at least 1 hour, and in some cases, for days, weeks, or months under standard storage conditions.

The hydrated film may have high clarity when wet. The hydrated film is generally stronger than hydrocolloid films of the same thickness and thus can be free of all reinforcing materials, such as woven or non-woven fabric or mesh. Thinner sheets can also be used than for hydrocolloid films. The exemplary face mask 10 is free of reinforcing materials.

The hydrated TPU film when tested for wet burst strength may have higher absolute peak force at break and greater % elongation than hydrocolloid films of the same thickness. This facilitates stretching of the film around facial or other body features without ripping and allows it to be handled easily.

The film may be solvent cast or extruded. In one embodiment, the film is solvent cast with or without the active agent 12. For example, the exemplary thermoplastic polyurethanes can be formed into granules which can be easily solubilized in alcohol/water mixtures and cast to form monolithic thin films 18. As an alcohol, ethanol and isopropanol may be used. As an alternative to alcohol, tetrahydrofuran, dimethylacetamide, dimethylformamide, or other water-miscible non-aqueous solvents can be used. The granules can also be extruded to form thin films 18. The films may be cast or extruded onto a release layer.

Being formed of a single layer 18 of material renders the face mask relatively inexpensive to produce. The active agent may be incorporated into the film prior to hydration (e.g. during solvent casting, during the hydration process, or after partial hydration, allowing customers to tailor the active agents to their particular treatments. For example, a cosmetic solution includes water, optionally a moisturizer/humectant, such as glycerin, and one or more (additional) active agents. Dry films of the TPU, on the release layer, may be soaked in a selected hydrating solution containing the selected active agents and excipients. The hydrated film may be shaped to form the face 10 mask, for example, by punching out the cavities 16 for the eyes, nose, and mouth. The hydrated face mask, containing the selected active agents and excipients, may be packaged in a foil pouch. These steps may be performed at different locations, for example, the dry film may be shipped to a facial mask manufacturer who may select and add the hydrating solution. This method eliminates the need for reinforcing the face mask using a mesh, fabric, or other substrate.

While the thin film finds particular use in facial masks, it may be used for applying an active agent to any part of the body, for example to apply an active agent to a wound.

The Thermoplastic Polyurethane

The unhydrated polyurethane film 18 includes, as a significant component (at least 30 wt. %, or at least 50 wt. %, or at least 80 wt. %), a thermoplastic polyurethane which includes a hard segment and a soft segment and optionally an intermediate segment.

In one embodiment, the thermoplastic polyurethane (denoted TPU1) includes a soft segment which is derived from a first high molecular weight polyether polyol (Polyol A) and a second high molecular weight polyether polyol (Polyol B) of lower molecular weight than the first polyol. Polyols A and B may be of the general form HO—$(R^1(R^2)O)_n$—H, where:

$R^1$ is selected from $C_2$—$C_4$ alkylene groups and mixtures thereof, such as —$CH_2CH$— and —$CH_2CH_2CH$—, $R^2$ is a side group and is selected from H and $C_1$—$C_2$ alkyl groups and mixtures thereof, and n is an integer which represents the average number of ether units by weight in each polyol, and where n is at least 20.

A ratio of the value of n for the first polyol to the value of n for the second polyol may be at least 1.5:1 or at least 2:1, or at least 3:1, or at least 4:1, and may be up to 20:1 or up to 10:1. The value of n for Polyol A may be at least 60 or at least 100 or at least 150 and may be up to 500 or up to 240. The value of n for Polyol B may be at least 25, or at least 30, and may be up to 50 or up to 45.

All molecular weights mentioned herein are weight average molecular weights and are expressed in daltons, unless otherwise noted. Polyol A may have an average molecular weight of at least 3000, or at least 4000, or at least 6000 daltons, and in some embodiments, up to 15,000, or up to 12,000, or up to 10,000 daltons. Polyol B may have an average molecular weight of no more than 2500, or no more than 2000, or no more than 1600 daltons, and in some embodiments, at least 800 daltons or at least 1000 daltons. A ratio of the molecular weight of Polyol A to polyol B may be at least 1.4:1 or at least 2:1 and may be up to 15:1 or up to 10:1, or up to 8:1. The soft segment thus has a bimodal distribution of average length of the polyether segments.

A molar ratio of Polyol B to Polyol A in the reaction mixture for forming the thermoplastic urethane may be at least 5:1 or at least 8:1 such as up to 20:1.

A weight ratio of Polyol B to Polyol A in forming the thermoplastic urethane may be from 1:1 to 5:1, such as at least 1.5:1, or at least 1:1.

The hard segment may be derived from a diisocyanate, and at least one of a diisocyanate and a chain extender. The chain extender may also be a polyol, such as a $C_1$—$C_{20}$ or $C_1$—$C_{12}$, or $C_2$—$C_{10}$ alkyl and/or aryl polyol. A molecular weight of the chain extender may be up to 300 daltons, or up to 250 daltons, or up to 200 daltons.

An optional intermediate segment may be derived from a third polyol (Polyol C) and a diisocyanate (in general, the same as is used for generating the hard segment). Polyol C may be a polyether polyol as for Polyols A and B, but where n is at least 3 or at least 5, or at least 7, and may be up to 20 or up to 12. A molecular weight of Polyol C may be at least 200, or at least 250, or at least 300 daltons and may be up to 800 or up to 500, or up to 400 daltons.

An example thermoplastic polyurethane is the reaction product of: 20-30 wt. % Polyol A, 40-70 wt. % Polyol B, 5-20 wt. % polyisocyanate, 0-5 wt. % Polyol C, 0.2-5 wt. % chain extender, optionally, one or more additional polymer forming components, and optionally up to 2 wt. % of a catalyst (totaling 100 wt. %). In combination, Polyols A and B may comprise at least 50 wt. %, or at least 70 wt. % of the total weight of polymer forming components in the reaction mixture.

The thermoplastic polyurethane may have a weight average molecular weight of from about 50,000 to about 1,000,000 daltons, or from about 75,000 to about 500,000, or from about 100,000 to about 300,000 daltons.

In another embodiment a thermoplastic polyurethane composition (TPU2) is as described for TPU1 but includes Polyol A but not Polyol B. In another embodiment a thermoplastic polyurethane composition (TPU3) is as described for TPU1 but includes Polyol B but not Polyol A. Blends of two or more of the thermoplastic polyurethanes TPU1, TPU2, and TPU3 are also contemplated. A weight ratio of TPU1:TPU2 and/or TPU3 may be at least 1:2. In one embodiment, the ratio is at least 1:1.5, or at least 1:1, or at least 2:1, and may be up to 100:1, or higher, such as up to 20:1, or up to 10:1.

The exemplary thermoplastic polyurethane is optionally blended in the dry film with one or more additional polymers. Additional polymers suitable for use herein include thermoplastic polyurethanes and crosslinked poly(acrylic acid) polymers.

Example crosslinked poly(acrylic acid) polymers include those that are crosslinked with an alkyl ether of pentaerythritol or an alkyl ether of sucrose. Suitable crosslinked poly(acrylic acid) polymers are available under the trade name Carbopol® from Lubrizol Advanced Materials, Inc. Examples include Carbopol® 934, Carbopol® 940, Carbopol® 941, Carbopol® 980, and Carbopol® 981, Carbopol® 981F and Carbopol® ETD 2020 polymers. A weight ratio of TPU:cross-linked poly(acrylic acid) polymer(s) may be at least 5:1, or at least 10:1, or at least 20:1, or at least 40:1, or at least 50:1 and may be up to 1000:1 or up to 100:1, such as about 60:1, where the TPU can include one or more of TPUs 1, 2, and 3.

The proportions of hard segment, soft segment, and intermediate segment in the TPU may be calculated as follows:

Wt. % soft segment=wt. % polyols having a molecular weight of at least 250 daltons.

Wt. % hard segment=wt. % isocyanate in hard segment+ wt. % chain extender: low molecular weight diol (less than 200 daltons) or other chain extender.

Wt. % intermediate segment=100 wt. % soft segment wt. % hard segment.

Wt. isocyanate in hard segment=[moles isocyanate moles polyols having a molecular weight of at least 250 daltons]× Mw isocyanate.

In one embodiment, the hard segment content (calculated as above) in the TPU is at least 4 wt. %, or at least 4.3 wt. %. The hard segment content in the TPU may be up to 12 wt. %, or up to 10 wt. %, or up to 9 wt. %.

In one embodiment, the soft segment content (calculated as above) in the TPU is at least 75 wt. %, or at least 80 wt. %. The soft segment content in the TPU may be up to 94 wt. %, or up to 92 wt. %. In one embodiment, the TPU is 9-11 wt. % hard segment, 84-88 wt. % soft segment, and the balance (e.g., 3-4 wt. %) intermediate segment. In one embodiment, the TPU is 4.5-11 wt. % hard segment, 84-91 wt. % soft segment, and the balance (e.g., 2.5-4 wt. %) is intermediate segment.

Polyols A, B, and C

Suitable hydroxyl terminated polyether polyols which are useful as Polyols A and B, and optionally Polyol C are derived from a diol or polyol having a total of, for example, from 2 to 15 carbon atoms, such as an alkyl diol or glycol, which is reacted with an ether comprising an alkylene oxide of, for example, from 2 to 6 carbon atoms, such as ethylene oxide, propylene oxide or a mixture thereof. For example, polyether polyols can be produced by first reacting propylene glycol with propylene oxide followed by subsequent reaction with ethylene oxide. Primary hydroxyl groups resulting from ethylene oxide are more reactive than secondary hydroxyl groups and thus are often more suitable.

Example polyether polyols include poly(ethylene glycol) formed by reaction of ethylene oxide with ethylene glycol, poly(propylene glycol) formed by reaction of propylene oxide with propylene glycol, a copolymer of ethylene oxide and a $C_3$ to $C_{15}$ alkylene oxide, in particular, a $C_3$ to $C_6$ alkylene oxide, such as poly(propylene glycol), e.g., a copolymer polyol comprising poly(propylene glycol) and poly(ethylene oxide) segments, poly(tetramethylene ether glycol) formed by reaction of water with tetrahydrofuran, which can also be described as polymerized tetrahydrofuran, and which is commonly referred to as PTMEG. Suitable polyether polyols also include polyamide adducts of an alkylene oxide and can include, for example, ethylenediamine adduct formed by reaction of ethylenediamine with propylene oxide, diethylenetriamine formed by reaction of diethylenetriamine with propylene oxide, and similar polyamide type polyether polyols.

Copolyethers can also be utilized in the described compositions. Typical copolyethers include the reaction product of THF and ethylene oxide; THF and propylene oxide; or ethylene oxide and propylene oxide. The first two are available from BASF as PolyTHF™ B, a block copolymer, and PolyTHF™ R, a random copolymer. The third is available as PolyG™ 55-56 from Lonza.

Chain Extender

The exemplary TPU composition is made using a chain extender (chain lengthening agent). Chain extenders include diols, diamines, and combinations thereof. The chain extender may have a molecular weight of up to 500 daltons or up to 300 daltons, such as at least 46 daltons.

One or more short chain polyols having from 2 to 20, or 2 to 12, or 2 to 10 or 2-8 carbon atoms may be used as chain extenders in the polyurethane forming composition to increase the molecular weight of the polyurethane. Examples of chain extenders include lower aliphatic polyols and short chain aromatic glycols having molecular weights of less than 500 or less than 300. Suitable chain extenders include organic diols (including glycols) having a total of from 2 to about 20 carbon atoms such as alkane diols, cycloaliphatic diols, alkylaryl diols, and the like. Exemplary alkane diols include ethylene glycol, diethylene glycol, 1,3propanediol, 1,3butanediol, 1,4butanediol, (BDO), 1,3butanediol, 1,5pentanediol, 2,2dimethyl-1,3propanediol, propylene glycol, dipropylene glycol, 1,6hexanediol, 1,7heptanediol, 1,9nonanediol, 1,10decanediol, 1,12dodecanediol, tripropylene glycol, triethylene glycol, and 3methyl-1,5pentanediol. Examples of suitable cycloaliphatic diols include 1,2cyclopentanediol, and 1,4cyclohexanedimethanol (CHDM). Examples of suitable aryl and alkylaryl diols include hydroquinone di(13hydroxyethyl) ether (HQEE), 1,2dihydroxybenzene, 1,3dihydroxybenzene, 1,4dihydroxybenzene, 1,2,3trihydroxybenzene, 1,2di(hydroxymethyl)benzene, 1,4di(hydroxymethyl)benzene, 1,3di (2hydroxyethyl)benzene, 1,2d i(2hydroxyethoxy)benzene, 1,4di(2hydroxyethoxy)benzene, bisethoxy biphenol, 2,2di (4hydroxyphenyl)propane (i.e., bisphenol A), bisphenol A ethoxylates, bisphenol F ethoxylates, 4,4-isopropylidenediphenol, 2,2-di[4-(2-hydroxyethoxy)phenyl]propane (HEPP), and mixtures thereof and the like.

Mixtures of one or more of the above chain extenders can also be utilized.

Chain extenders with functionality greater than 2 may be used so long as the resulting TPU retains its thermoplasticity. Examples of such chain extenders include trimethylolpropane (TMP), glycerin and pentaerythritol. Generally, the addition of such chain extenders should not exceed 10% relative to the weight of the difunctional chain extenders.

In one embodiment, the chain extender is selected from 1,4-butanediol, and 1,10-decanediol.

Chain extenders can also be based on diamines. Exemplary diamines may have molecular weights of less than 500, and include, for example, as ethylenediamine, diethylenediamine, tetramethylenediamine, hexamethylenediamine, diethylenetriamine triethylenetetramine, tetraethylenepentamine, pentaethylenehexamine, piperazine, morpholine, substituted morpholine, piperidine, substituted piperidine, 2-amino-1-ethylpiperazine hydrazine, 1,4-cyclohexanediamine, and mixtures thereof. Alkanolamines, such as ethanolamine, diethanolamine, and triethanolamine, may also be used. Further examples of chain lengthening agents include aniline, and the like.

The molar amount or ratio of the total hydroxyl groups of the one or more chain extenders utilized to the total hydroxyl groups of Polyols A, B, and C may be from about 0.1 to about 5.0, or from about 0.2 to about 4.0, or from about 0.4 to about 2.5.

Polyisocyanate

The polyisocyanate includes one or more polyisocyanates. Suitable polyisocyanates include aromatic diisocyanates, aliphatic diisocyanates, and mixtures thereof.

In order to form relatively long linear polyurethane chains, di-functional or polyfunctional isocyanates are utilized. In one embodiment, one or more diisocyanates are utilized. The polyisocyanates useful herein generally have a formula $R(NCO)_n$, where n is at least 2. R can be an aromatic, a cycloaliphatic, an aliphatic, or combinations thereof having from 2 to about 20 carbon atoms.

Examples of aromatic diisocyanates include 4,4'-diphenylmethane diisocyanate (MDI), m-xylene diisocyanate (XDI), phenylene-1,4-diisocyanate, naphthalene-1,5-diisocyanate, 2,4-toluene diisocyanate (2,4-TDI), 2,6-toluene diisocyanate (2,6-TDI), 1,4-phenylene diisocyanate, 1,3-phenylene diisocyanate, 3,3'-dimethoxy-4,4-biphenylene diisocyanate, 3,3'-dimethyl-4,4'-biphenylene diisocyanate (TODI), 4,4-diisocyanate-diphenyl ether, 2,4-naphthalene diisocyanate, 1,5-naphthalene diisocyanate, 1,3-xylene diisocyanate, 1,4-xylene diisocyanate.

Examples of aliphatic diisocyanates include isophorone diisocyanate (IPDI), 1,4-butane diisocyanate (BDI), tetramethylene diisocyanate, hexamethylene diisocyanate (HDI), 1,4-cyclohexyl diisocyanate (CHDI), decane-1,10-diisocyanate, lysine diisocyanate (LDI), isophorone diisocyanate (PDI), 1,5-naphthalene diisocyanate (ND!), 4,4'-diisocyanato dicyclohexylmethane (H12MDI), 1,3-diisocyanate methylcyclohexane, 1,4-diisocyanate methylcyclohexane, 4,4-diisocyanate dicyclohexane, 4,4-diisocyanato dicyclohexylmethane, and isomers, dimers, trimers and mixtures thereof.

In one embodiment, the isocyanate is selected from cycloaliphatic and aromatic diisocyanates. In one specific embodiment, the isocyanate is selected from MDI and H12MDI.

Suitable polyisocyanates are commercially available from companies such as Bayer Corporation of Pittsburgh, Pa., The BASF Corporation of Parsippany, N.J., The Dow Chemical Company of Midland, Mich., and Huntsman Chemical of Utah.

The molecular weight of the polymers described herein are determined by gel permeation chromatography (GPC) calibrated with a poly(methyl methacrylate) (PMMA) standard. Number average molecular weights are measured by GPC using a PL-GPC 220 high temperature GPC instrument manufactured by Polymer Laboratories (Varian, Inc.). Approximately 0.02 g polymer sample is dissolved in 5 ml of dimethyl acetamide (DMAc), containing 250 ppm of butylated hydroxytoluene (BHT) and 0.05 molar $NaNO_3$. The test sample solution is gently shaken for about two hours and filtered by passing the sample solution through a 0.45 µm PTFE disposable disc filter. The chromatographic conditions are: Mobile phase: DMAc, with 250 ppm BHT and 0.05 M $NaNO_3$, 70° C., 1.0 ml/min. Sample size: 100 µl Column set: PLgel (Guard+2× Mixed-A), all 10 µm, in series. Waters Empower Pro LC/GPC software is used to analyze the results and to calculate Mn. The weight average and number weight average molecular weights of the polymers described herein are obtained by integrating the area under the peak corresponding to the polymer, which is normally the major high molecular weight peak, excluding peaks associated with diluents, impurities, and other additives.

Catalyst

One or more polymerization catalysts may be present during the polymerization reaction. Generally, any conventional catalyst can be utilized to react the diisocyanate with the polyol intermediates and/or the chain extender. Examples of suitable catalysts which in particular accelerate the reaction between the NCO groups of the diisocyanates and the hydroxy groups of the polyols and chain extenders include organic tin compounds such as dibutyltin diacetate, dibutyltin dilaurate (DBTL), dioctyltin dilaurate (DOTDL), and dibutyltin bis(ethoxybutyl 3-mercaptopropionate); titanic acid; organic titanium compounds such as tetraisopropyl titanate, tetra-n-butyl titanate, polyhydroxytitanium stearate and titanium acetylacetonate; tertiary amines such as triethylene diamine, triethylamine N-methylmorpholine, N,N,N',N'-tetramethylethylenediamine, N,N,N',N'-tetramethylhexamethylene diamine, triethylamine, N,N'-dimethylpiperazine, N,N-dimethylaminoethanol, dimethylcyclohexylamine, and diazabicyclo[2.2.2]octane; and mixtures of two or more thereof.

The total amount of the catalyst used may be from 0.0001 to 0.1 part by weight per 100 parts by weight of the polyols A, B, and C.

Other Additives

Various types of optional components can be present during the polymerization reaction, and/or incorporated into the TPU described above to improve processing and other properties. These additives include antioxidants, such as phenolic types, organic phosphites, phosphines and phosphonites, hindered amines, organic amines, organosulfur compounds, lactones and hydroxylamine compounds, biocides, fungicides, antimicrobial agents, compatibilizers, electro-dissipative or anti-static additives, fillers and reinforcing agents, such as titanium dioxide, alumina, clay and carbon black, flame retardants, such as phosphates, halogenated materials, and metal salts of alkyl benzenesulfonates, impact modifiers, such as methacrylate-butadiene-styrene ("MBS") and methyl methacrylate/butyl acrylate ("MBA"), mold release agents such as waxes, fats and oils, pigments and colorants, plasticizers, polymers, rheology modifiers such as monoamines, polyamide waxes, silicones, and polysiloxanes, slip additives, such as paraffinic waxes, hydrocarbon polyolefins and/or fluorinated polyolefins, and UV stabilizers, which may be of the hindered amine light stabilizers (HALS) and/or UV light absorber (UVA) types. Other additives may be used to enhance the performance of the TPU composition or blended product. All of the additives described above may be used in an effective amount customary for these substances.

These additional additives can be incorporated into the components of, or into the reaction mixture for, the preparation of the TPU resin, or after making the TPU resin. In another process, all the materials can be mixed with the TPU resin and then melted or they can be incorporated directly into the melt of the TPU resin.

Active Agents

The hydrated polyurethane film includes one or more active agents. One or more excipients may also be present. One or more of the active agents and/or excipients may be introduced to the preformed dry film in a hydrating composition, such as water, an alcohol or other organic solvent, combination thereof, or the like. In another embodiment, one or more of the active agents and/or excipients is combined with the polyurethane polymer to form a casting solution and cast together to form a polyurethane polymer film, which may be then dried to form the dry polyurethane film.

Active agents useful herein may be categorized or described herein by their therapeutic and/or cosmetic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated application or applications listed.

Active agents useful herein may be delivered to the surface of the skin, known as the stratum corneum, may be delivered to the underlying portions of the skin known as the dermis and epidermis. Active agents may also be medicinal drug substances which penetrate through the initial layers of the skin to the underlying tissue, in this respect the active agents may have local effect and are not systemic. Active agents may also have percutaneous absorption and have a systemic effect where the active agent is considered a medicinal drug substance and after absorption is transported via the blood to the body systemically.

The active agents may be selected from skin whitening or depigmenting agents, anti-acne agents, anti-wrinkle and/or anti-aging agents, pain management agents, agents stimulating healing, emollients, AQP-3 modulating agents, aquaporin modulating agents, proteins from the aquaporin family, collagen synthesis stimulating agents, agents modulating PGC-1-α synthesis, agents modulating the activity of PPARγ, agents which increase or reduce the triglyceride content of adipocytes, agents stimulating or delaying adipocyte differentiation, lipolytic agents or agents stimulating lipolysis, anti-cellulite agents, adipogenic agents, inhibitors of acetylcholine-receptor aggregation, agents inhibiting muscle contraction, anticholinergic agents, elastase inhibiting agents, matrix metalloproteinase inhibiting agents, melanin synthesis stimulating or inhibiting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, skin conditioners, humectants, substances which retain moisture, alpha hydroxy acids, beta hydroxy acids, moisturizers, hydrolytic epidermal enzymes, vitamins, amino acids, proteins, biopolymers, gelling polymers, agents able to reduce or treat the bags under the eyes, exfoliating agents, desquamating agents, keratolytic agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, heat shock proteins, HSP70 synthesis stimulators, heat shock protein synthesis-stimulating agents, hyaluronic acid synthesis-stimulating agents, fibronectin synthesis-stimulating agents, sirtuin synthesis-stimulating agents, agents stimulating the synthesis of lipids and components of the stratum corneum (ceramides, fatty acids), agents that inhibit collagen degradation, agents that inhibit elastin degradation, agents that inhibit serine proteases, agents stimulating fibroblast proliferation, agents stimulating keratinocyte proliferation, agents stimulating adipocyte proliferation, agents stimulating melanocyte proliferation, agents stimulating keratinocyte differentiation, agents that inhibit acetylcholinesterase, skin relaxant agents, glycosaminoglycan synthesis-stimulating agents, antihyperkeratosis agents, comedolytic agents, anti-psoriasis agents, anti-dermatitis agents, anti-eczema agents, DNA repair agents, DNA protecting agents, stabilizers, anti-itching agents, agents for the treatment and/or care of sensitive skin, firming agents, redensifying agents, restructuring agents, anti-stretch mark agents, binding agents, agents regulating sebum production, antiperspirant agents, coadjuvant healing agents, agents stimulating reepithelialization, coadjuvant reepithelialization agents, cytokine growth factors, cytokine growth factors, agents which act on capillary circulation and/or microcirculation, calming agents, anti-inflammatory agents, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, chelating agents, plant extracts, essential oils, marine extracts, agents obtained from a biofermentation process, mineral salts, cell extracts, sunscreens and organic or mineral photoprotective agents active against ultraviolet A and/or B rays, and mixtures thereof.

Skin Whitening and Depigmenting Agents

Exemplary skin-whitening or depigmenting agents include hydrogen peroxide, pyridine-3-carboxamide (nicotinamide), kojic acid, hydroquinine, mulberry root extract, liquorice root extract, *Scutellaria baicalensis* extract, grape extract, ferulic acid, hinokitiol, arbutin, α-arbutin (bearberry extract), and mixtures thereof. extracts of *Achillea millefolium, Aloe vera, Azadirachta indica, Osmunda japonica, Artocarpus incisus, Bidens pilosa, Broussonetia papyrifera, Chlorella vulgaris, Cimicifuga racemosa, Emblica officinalis, Glycyrrhiza glabra, Glycyrrhiza uralensis, Ilex purpurea, Ligusticum lucidum, Ligusticum wallichii, Mitracarpus scaber, Morinda citrifolia, Morus alba, Morus bombycis, Naringi crenulata, Prunus domestica, Pseudostellaria heterophylla, Rumex crispus, Rumex occidentalis, Sapindus mukorossi, Saxifraga sarmentosa, Scutellaria galericulata, Sedum sarmentosum Bunge, Stellaria medica, Triticum Vulgare, Arctostaphylos uva ursi* or *Withania somnifera*, flavonoids, soy extract, lemon extract, orange extract, ginkgo extract, cucumber extract, geranium extract, bearberry (gayuba) extract, carob extract, cinnamon extract, marjoram extract, rosemary extract, clove extract, soluble liquorice extract, blackberry leaf extract, Lipochroman-6™ [INCI: dimethylmethoxy chromanol] and Chromabright™ [INCI: dimethylmethoxy chromanyl palmitate] marketed by Lipotec, Actiwhite™ LS 9808 [INCI: water, glycerin, sucrose dilaurate, polysorbate 20, *Pisum sativum* (pea) extract] and Dermawhite® NF LS 9410 [INCI: mannitol, arginine HCl, phenylalanine, disodium EDTA, sodium citrate, kojic acid, citric acid, yeast extract] marketed by Laboratoires Serobiologiques/Cognis, Lumiskin™ [INCI: caprylic/capric triglyceride, diacetyl-boldine], Melaclear™ [INCI: glycerin, water, dithiaoctanediol, gluconic acid, sutilains, beta-carotene], O.D.A.white™ [INCI: octadecenedioic acid] and Etioline™ [INCI: glycerin, butylene glycol, *Arctostaphylos uva ursi* leaf extract, *Mitracarpus scaber* extract] marketed by Sederma, Sepiwhite™ MSH [INCI: undecylenoyl phenylalanine] marketed by Seppic, Achromaxyl™ [INCI: water, *Brassica napus* extract] marketed by Vincience, Gigawhite™ [INCI: water, glycerin, *Malva sylvestris* (mallow) extract, *Mentha piperita* leaf extract, *Primula veris* extract, *Alchemilla vulgaris* extract, *Veronica officinalis* extract, *Melissa officinalis* leaf extract, *Achillea millefolium* extract], Melawhite® [INCI: leukocyte extract, AHA] or Melfade®-J [INCI: water, *Arctostaphylos uva-ursi* leaf extract, glycerin, magnesium ascorbyl phosphate] marketed by Pentapharm, Albatin® [INCI: 1aminoethylphosphinic acid, butylene glycol, water] marketed by Exsymol, Tyrostat™-11 [INCI: water, glycerin, *Rumex occidentalis* extract] and Melanostatine®-5 [INCI: dextran, nonapeptide-1] marketed by Atrium Innovations, arbutin and its isomers, kojic acid and derivatives thereof, ascorbic acid and derivatives thereof such as 6-O-palmitoylascorbic acid, ascorbyl glucoside, dipalmitoyl ascorbic acid, sodium ascorbyl phosphate (NAP), magnesium ascorbyl phosphate (MAP), aminopropyl ascorbyl phosphate, ascorbyl glucoside or ascorbyl tetraisopalmitate (VCIP); retinol and derivatives thereof including tretinoin and isotretinoin, idebenone, hydroxybenzoic acid and derivatives thereof, niacinamide, liquiritin, resorcinol and derivatives thereof, hydroquinone, α-tocopherol, γ-tocopherol, azelaic acid, potassium azeloyl diglycinate, resveratrol, linoleic acid, α-lipoic acid, dihydrolipoic acid, α-hydroxy acids, β-hydroxy acids, ellagic acid, ferulic acid, cinnamic acid, oleanolic acid, aloesin and its derivatives, serine protease inhibitors, for example tryptase, trypsin and PAR-2 inhibitors, and mixtures thereof.

Anti-Acne Agents

Exemplary anti-acne agents include salicylic acid, glycolic acid, lactobionic acid, azelaic acid, benzoyl peroxide, antibiotics such as Clindamycin, sodium sulfacetamide and erythromycin, retinoids such as adapalene, tazarotene, and tretinoin, which may be sold under trade names such as Retin-A, Differin™, Renova™, and Tazorac™, and mixtures thereof.

Anti-Wrinkle and/or Anti-Aging Agents

Exemplary anti-wrinkle agents and/or anti-aging agents include extracts or hydrolyzed extracts of *Vitis vinifera, Rosa canina, Curcuma longa, Iris pallida, Theobroma cacao, Ginkgo biloba, Leontopodium alpinum, Dunaliella salina*, synthetic compounds or products, such as Matrixyl® [INCI: palmitoyl pentapeptide-4], Matrixyl® 3000 [INCI: palmitoyl tetrapeptide-7, palmitoyl oligopeptide], Essenskin™ [INCI: calcium hydroxymethionine], Renovage™ [INCI: teprenone] or Dermaxyl™ [INCI: palmitoyl oligopeptide] marketed by Sederma/Croda, Vialox™ [INCI: pentapeptide 3], Syn®-Ake [INCI: dipeptide diaminobutyroyl benzylamide diacetate], Syn®Coll [INCI: palmitoyl tripeptide-5], Phytaluronate™ [INCI: locust bean (Ceratonia siliqua) gum] or Preregen™ [INCI: Glycine soja (soybean) protein, oxidoreductases] marketed by Pentapharm/DSM, Myoxinol™ [INCI: hydrolyzed Hibiscus esculentus extract], Syniorage™ [INCI: acetyl tetrapeptide-11], Dermican™ [INCI: acetyl tetrapeptide-9] or DN AGE™ LS [INCI: Cassia alata leaf extract] marketed by Laboratoires Serobiologiques/Cognis, Algisium C™ [INCI: methylsilanol mannuronate] or Hydroxyprolisilane CN™ [INCI: methylsilanol hydroxyproline aspartate] marketed by Exsymol, Argireline™ [INCI: acetyl hexapeptide-8], SNAP-7 [INCI: acetyl heptapeptide-4], SNAP-8 [INCI: acetyl octapeptide-3], Leuphasyl® [INCI: pentapeptide-18], Inyline™ [INCI: acetyl hexapeptide-30], Aldenine® [INCI: hydrolyzed wheat protein, hydrolyzed soy protein, tripeptide 1], Preventhelia® [INCI: diaminopropionoyl tripeptide-33], Decorinyl™ [INCI: tripeptide-10 citrulline], Trylagen® [INCI: Pseudoalteromonas ferment extract, hydrolyzed wheat protein, hydrolyzed soy protein, tripeptide 10 citrulline, Tripeptide 1], Eyeseryl® [INCI: acetyl tetrapeptide-5], Peptide AC29 [INCI; acetyl tripeptide-30 citrulline], Relistase™ [INCI: acetylarginyltriptophyl diphenylglycine], Thermostressine™ [INCI: acetyl tetrapeptide-22], Lipochroman 6 [INCI: dimethylmethoxy chromanol], Chromabright™ [INCI: dimethylmethoxy chromanyl palmitate], Antarcticine® [INCI: Pseudoalteromonas ferment extract], dGlyage™ [INCI: lysine HCl, lecithin, tripeptide-9 citrulline], Vilastene™ [INCI: lysine HCl, lecithin, tripeptide-10 citrulline] or Hyadisine™ [INCI: Pseudoalteromonas ferment extract] marketed by Lipotec, Kollaren™ [INCI: tripeptide 1, dextran] marketed by Institut Europeen de Biologie Cellulaire, Collaxyl™ IS [INCI: hexapeptide-9], Laminixyl IS™ [INCI: heptapeptide], Orsirtine™ GL [INCI: *Oryza sativa* (rice) extract], D'Orientine™ IS [INCI: *Phoenix dactylifera* (Date) seed extract], Phytoquintescine™ [INCI: Einkorn (*Triticum monococcum*) extract] or Quintescine™ IS [INCI: dipeptide-4] marketed by Vincience/ISP, BONTLPeptide [INCI: palmitoyl hexapeptide-19] marketed by Infinitec Activos, Deepaline™ PVB [INCI: palmitoyl hydrolyzed wheat protein] or Sepilift™ DPHP [INCI: dipalmitoyl hydroxyproline] marketed by Seppic, Gatuline™ Expression [INCI: *Acmella oleracea* extract], Gatuline™ In-Tense™ [INCI: *Spilanthes acmella* flower extract] and Gatuline™ Age Defense 2 [INCI: *Juglans regia* (walnut) seed extract] marketed by Gattefosse, Thalassine™ [INCI: algae extract] marketed by Biotechmarine, ChroNOline™ [INCI: caprooyl tetrapeptide-3] and Thymulen-4™ [INCI: acetyl tetrapeptide-2] marketed by Atrium Innovations/Unipex Group, EquiStat™ [INCI: Pyrus malus fruit extract, glycine soja seed extract] or Juvenesce [INCI: octyldodecanol, caprylic/capric triglyceride, Retinol, ursolic acid, BHT, butylene glycol, ilomastat] marketed by Coletica/Engelhard/BASF, Ameliox™ [INCI: carnosine, tocopherol, *Silybum marianum* fruit extract] and Phyto-CellTec™ *Malus domestica* [INCI: *Malus domestica* fruit cell culture] marketed by Mibelle Biochemistry, Bioxilift™ [INCI: *Pimpinella anisum* extract] and SMS AntiWrinkle™ [INCI: *Annona squamosa* seed extract] marketed by Silab, antagonists of the $Ca^{2+}$ channel, such as alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, chloride channel agonists, and mixtures thereof.

For example, U.S. Pat. No. 8,110,207 describes compound of general formula (I)

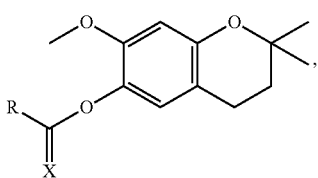

(6substituted 7methoxy-2,2dimethylchromanes), and cosmetically or pharmaceutically acceptable salts, wherein R is a linear or branched, saturated or unsaturated aliphatic group containing 2 to 23 carbon atoms, or a cyclic group, and which can contain substituents selected from hydroxy, alkoxy, amino, carboxyl, cyano, nitro, alkylsulfonyl or halogen atoms; and X is selected from O and S.

Moisturizing Agents, Humectants, Substances that Retain Moisture, and Emollients Exemplary moisturizing agents, humectants and emollients include sodium pyrrolidone carboxylate; betaines, such as N,N,N-trimethylglycine; yeast extract; polyols and polyethers such as glycerin, ethylhexylglycerin, caprylyl glycol, pentylene glycol, butylene glycol, propylene glycol and their derivatives, triethylene glycol, polyethylene glycol, Glycereth-26, Sorbeth-30; panthenol; pyroglutamic acid and its salts and derivatives; amino acids, such as serine, proline, alanine, glutamate or arginine; ectoine and its derivatives; N(2hydroxyethyl)acetamide; N-lauroyl-pyrrolidone carboxylic acid; N-lauroyl-L-lysine; N-alphabenzoyl-L-arginine; urea; creatine; α- and β-hydroxy acids such as lactic acid, glycolic acid, malic acid, citric acid or salicylic acid, and their salts, such as sodium lactate and lactic acid bacteria fermented solution; polyglyceryl acrylate; sugars and polysaccharides, such as glucose, saccharide isomerate, sorbitol, pentaerythritol, inositol, xylitol, trehalose and derivatives thereof, sodium glucuronate, carraghenates (*Chondrus crispus*) and chitosan; glycosaminoglycans such as hyaluronic acid and derivatives thereof such as sodium hyaluronate; aloe vera in any of its forms; honey; soluble collagen; lecithin and phosphatidylcholine; ceramides; cholesterol and its esters; tocopherol and its esters, such as tocopheryl acetate or tocopheryl linoleate; long-chain alcohols such as cetearyl alcohol, stearyl alcohol, cetyl alcohol, oleyl alcohol, isocetyl alcohol or octadecan-2-ol; long-chain alcohol esters such as lauryl lactate, myristyl lactate or $C_{12}$—$C_{15}$ alkyl benzoates; fatty acids such as stearic acid, isostearic acid or palmitic acid; polyunsaturated fatty acids (PUFAs); sorbitans such as sorbitan distearate; glycerides such as glyceryl monoricinoleate, glyceryl monostearate, glyceryl stearate citrate or caprylic and capric acid triglyceride; saccharose esters such as saccharose palmitate or saccharose oleate; butylene glycol esters, such as dicaprylate and dicaprate; fatty acid esters such as isopropyl isostearate, isobutyl palmitate, isocetyl stearate, isopropyl laurate, hexyl laurate, decyl oleate, cetyl palmitate, di-n-butyl sebacate, isopropyl myristate, isopropyl palmitate, isopropyl stearate, butyl stearate, butyl myristate, isopropyl linoleate, 2-ethylhexyl palmitate, 2ethylhexyl cocoate, decyl oleate, myristyl myristate; squalene; mink oil; lanolin and its derivatives; acetylated lanolin alcohols; silicone derivatives such as cyclomethicone, dimethicone or dimethylpolysiloxane; Antarcticine® [INCI: Pseudoalteromonas Ferment extract] or acetyl-glutamyl-methionyl-alanyl-isoleucine, acetyl-arginyl-phenylglycyl-phenylglycine or acetyl-arginyl-6aminohexanoyl-alanine marketed by Lipotec, petrolatum; mineral oil; mineral and synthetic waxes; beeswax (*Cera alba*); paraffin; or waxes and oils with vegetable origins such as candelilla wax (*Euphorbia cerifera*), carnauba wax (*Copernicia cerifera*), shea butter (*Butirospermum parkii*), cocoa butter (*Theobroma cacao*), castor oil (*Ricinus communis*), sunflower oil (*Helianthus annuus*), olive oil (*Olea europaea*), coconut oil (*Cocos nucifera*), palm oil (*Elaeis guineensis*), wheat germ oil (*Triticum vulgare*), sweet almond oil (*Prunus amygdalus dulcis*), musk rose oil (*Rosa moschata*), soya bean oil (*Glycine soja*), grape seed oil (*Vitis vinifera*), calendula oil (*Calendula officinalis*), jojoba oil (*Simmondsia chinensis*), mango oil (*Mangifera indica*), avocado oil (*Persea gratissima*), and mixtures thereof.

Anti-Inflammatory Agents

Exemplary anti-inflammatory agents include seal whip extract, *Polygonum cuspidatum* root extract, allantoin, madecassoside extract, echinacea extract, amaranth seed oil, sandal wood oil, peach tree leaf extract, extract of *Aloe vera, Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforaturn, Lilium candidum, Malva sylvestris, Melaleuca alternifolia, Origanum majorana, Origanum vulgare, Prunus laurocerasus, Rosmarinus officinalis, Salix alba, Silybum marianum, Tanacetum parthenium, Thymus vulgaris, Uncaria guianensis* or *Vaccinium myrtillus*, spike moss extract, lysozyme chloride, mometasone furoate, prednisolone, nonsteroidal anti-inflammatories including loxoprofen sodium, flurbiprofen, diclofenac sodium, tiaramide hydrochloride, cyclooxygenase or lipoxygenase inhibitors, benzydamine, acetylsalicylic acid, rosmarinic acid, ursolic acid, glycyrrhizic acid and sodium, potassium and ammonium salts thereof, α-bisabolol, azulene and analogues, sericoside, ruscogenin, escin, scoline, rutin and analogues, hydrocortisone, clobetasol, dexamethasone, prednisone, paracetamol, amoxiprin, benorilate, choline salicylate, faislamine, methyl salicylate, magnesium salicylate, salsalate, diclofenac, aceclofenac, acemetacin, bromfenac, etodolac, indomethacin, oxametacin, proglumetacin, sulindac, tolmetin, ibuprofen, dexibuprofen, carprofen, fenbufen, fenoprofen, flurbiprofen, ketoprofen, dexketoprofen, ketorolac, loxoprofen, naproxen, miroprofen, oxaprozin, pranoprofen, tiaprofenic acid, suprofen, mefenamic acid, meclofenamate, meclofenamic acid, flufenamic acid, tolfenamic acid, nabumetone, phenylbutazone, azapropazone, clofezone, kebuzone, metamizole, mofebutazone, oxyphenbutazone, phenazone, sulfinpyrazone, piroxicam, lornoxicam, meloxicam, tenoxicam, celecoxib, etoricoxib, lumiracoxib, parecoxib, rofecoxib, valdecoxib, nimesulide, naproxcinod, fluproquazone or licofelone, omega-3 and omega-6 fatty acids, morphine, codeine, oxycodone, hydrocodone, diamorphine, pethidine, tramadol, buprenorphine, benzocaine, lidocaine, chloroprocaine, tetracaine, procaine, amitriptyline, carbamazepine, gabapentin, pregabalin, bisabolol, Neutrazen™ [INCI: water, butylene glycol, dextran, palmitoyl tripeptide-8] marketed by Atrium lnnovations/Unipex Group, Meliprene® [INCI: dextran, Acetyl Heptapeptide-1] marketed by Institut Europeen de Biologie Cellulaire/Unipex Group, Skinasensyl™ [INCI: acetyl tetrapeptide-15] or Anasensyl™ [INCI: mannitol, ammonium glycyrrhizate, caffeine, *Hippocastanum* (Horse Chestnut) extract] marketed by Laboratoires Serobiologiques/Cognis, Calmosensine™ [INCI: acetyl dipeptide-1] marketed by Sederma, coenzyme Q10 or alkylglyceryl ethers, and mixtures thereof.

DNA Repair Agents

Exemplary DNA repair agents include C1—C8 alkyl tetrahydroxycyclohexanoate, micrococcus lysate, bifida ferment lysate, DNA repair enzymes such as photolyase and T4 endonuclease V, and mixtures thereof.

Skin Lipid Barrier Repair Agents

Exemplary skin lipid barrier repair agents include phytosphingosine, linoleic acid, cholesterol, and mixtures thereof.

Anti-Cellulite Agents

Exemplary anti-cellulite agents include *Coleus forskohlii* root extract, *Magnolia grandiflora* bark extract, *Nelumbo nucifera* leaf extract, and mixtures thereof.

Wound Healing Agents

Exemplary wound-healing agents, coadjuvant healing agents, agents stimulating re-epithelialization and/or coadjuvant re-epithelialization agents include extracts of *Aristolochia clematis, Centella asiatica, Rosa moschata, Echinacea angustifolia, Symphytum officinale, Equisetum arvense, Hypericum perforaturn, Mimosa tenuiflora, Persea gratissima, Prunus africana, Tormentilla erecta, Aloe vera*, soybean protein, Polyplant® Epithelizing [INCI: *Calendula officinalis, Hypericum perforatum, Chamomilla recutita, Rosmarinus officinalis*] marketed by Provital, Cytokinol® LS 9028 [INCI: hydrolyzed casein, hydrolyzed yeast protein, lysine HCl] marketed by Laboratories Serobiologiques/Cognis or Definer® [INCI: *Zea May* (Corn) Kernel extract] marketed by Coletica/Engelhard/BASF, allantoin, cadherins, integrins, selectins, hyaluronic acid receptors, immunoglobulins, fibroblast growth factor, connective tissue growth factor, platelet-derived growth factor, vascular endothelial growth factor, epidermal growth factor, insulin-like growth factor, keratinocyte growth factors, colony-stimulating factors, transforming growth factor beta, tumor necrosis factor alpha, interferons, interleukins, matrix metalloproteinases, cytokines, extra cellular matrices such as collagen I, II, and III, receptor protein tyrosine phosphatases, Antarcticine® [INCI: *Pseudoalteromonas* ferment extract], Decorinyl® [INCI: Tripeptide-10 citrulline], Trylagen® [INCI: Pseudoalteromonas ferment extract, hydrolyzed wheat protein, hydrolyzed soy protein, tripeptide-10 citrulline, Tripeptide-1], Bodyfensine™ [INCI: acetyl dipeptide-3 aminohexanoate], marketed by Lipotec, and mixtures thereof.

Muscle Relaxants, Aagents Inhibiting Muscle Contraction, Agents Inhibiting Acetylcholine Receptor Clustering and Anticholinergic Agents Exemplary muscle relaxants, agents inhibiting muscle contraction, agents inhibiting acetylcholine receptor clustering and anticholinergic agents include extracts of *Atropa belladonna, Hyoscyamus niger, Mandragora officinarum, Chondrodendron tomentosum*, plants of the *Brugmansia* genus, or the *Datura* genus, *Clostridium botulinum* toxin, peptides derived from the protein SNAP-25 or Inyline™ [INCI: acetyl hexapeptide-30] marketed by Lipotec, baclofen, carbidopa, levodopa, bromocriptine, chlorphenesin, chlorzoxazone, donepezil, mephenoxalone, reserpine, tetrabenazine, dantrolene, thiocolchicoside, tizanidine, clonidine, procyclidine, glycopyrrolate, atropine, hyoscyamine, benztropine, scopolamine, promethazine, diphenhydramine, dimenhydrinate, dicyclomine, cyclobenzaprine, orphenadrine, flavoxate, cyclopentolate, ipratropium, oxybutynin, pirenzepine, tiotropium, trihexyphenidyl, tolterodine, tropicamide, solifenacin, darifenacin, mebeverine, trimethaphan, atracurium (besylate), cisatracurium, doxacurium, fazadinium, metocurine, mivacurium, pancuronium, pipecuronium, rapacuronium, tubocurarine, dimethyl tubocurarine, rocuronium, vecuronium, suxamethonium, 18-methoxycoronaridine, carisoprodol, febarbamate, meprobamate, metocarbamol, phenprobamate, tibamate, anticonvulsant agents such as levetiracetam, stiripentol, phenobarbital, methylphenobarbital, pentobarbital, metharbital, barbexaclone, primidone, carbamazepine, oxcarbazepine, benzodiazepines, for example clonazepam, cloxazolam, clorazepate, diazepam, flutoprazepam, lorazepam, midazolam, nitrazepam, nimetazepam, phenazepam, temazepam, tetrazepam, clobazam, hydrochloric acid epihydrochloride, talipexole hydrochloride, tolperisone hydrochloride, and mixtures thereof.

Pain Management Agents

Exemplary pain management agents and local anesthetics include lidocaine and salts such as lidocaine hydrochloride, bupivacaine and bupivacaine hydrochloride, mepivacaine and mepivacaine hydrochloride, etidocaine, prilocaine and prilocaine hydrochloride, tetracaine, procaine, chloroprocaine, benzocaine, and their salts; counterirritant agents that mask pain such as menthol, camphor, methylsalicylate, cinnamaldehyde, capsaicin and mixtures thereof, acetylsalicylic acid (aspirin) and other salicylic acid esters, diclofenac and salts thereof such as sodium, diethylamine, ibuprofen, ketoprofen, acetaminophen and other non-steroidal anti-inflammatory drugs, analgesic drugs such as morphine hydrochloride, fentanyl citrate, buprenorphine hydrochloride, and the like, and mixtures thereof.

Hair Growth Retardation and Stimulation Agents

Exemplary hair growth retardation agents include ursolic acid, Boswellia serrata extract, activin and activin agonists, flavonoids such as quercetin, curcumin, galangin, fisetin, myricetin, apigenin; propyl gallate, nordihydroguaiaretic acid, caffeic acid, tyrosine kinase inhibitors such as lavendustin, erbstatin, tyrphostins, benzoquinone-ansamycin herbimycin A, thiazolidinediones, phenazocine, 2,3-dihydro-2thioxo-1Hindo1-3alkanoic acids, phenothiazine derivatives such as thioridazine; sphingosine and derivatives thereof such as phytosphingosine; staurosporine and derivatives thereof, glycyrrhetinic acid, lauryl isoquinolinium bromide, Decelerine™ [INCI: lauryl isoquinolinium bromide, Pseudoalteromonas ferment extract] marketed by Lipotec, serine protease inhibitors, trypsin, and mixtures thereof.

Exemplary hair growth stimulating agents include *Serenoa serrulata* fruit extract, licorice extract, *Tussilago farfara* or *Achillea millefolium*, nicotinic acid esters such as $C_3$—$C_6$ alkyl nicotinates such as methyl or hexyl nicotinate, benzyl nicotinate, or tocopheryl nicotinate; biotin, 5α-reductase-inhibiting agents, anti-inflammatory agents, retinoids, for example all-trans-retinoic acid or tretinoin, isotretinoin, retinol or vitamin A, and derivatives thereof, such as zinc salt of acetate, palmitate, propionate, motretinide, etretinate and trans-retinoate; anti-bacterial agents, calcium channel blockers, for example cinnarizine and diltiazem; hormones, for example estriol and its analogues and thyroxine and its analogues and/or salts; antiandrogenic agents, for example oxendolone, spironolactone and diethylstilbestrol; anti-radical agents, esterified oligosaccharides, for example those described in documents EP 0211610 and corresponding U.S. Pat. No. 4,761,401 and EP 0064012 and corresponding U.S. Pat. No. 4,607,025; derivatives of hexosaccharic acids, for example glucosaccharic acid or those described in EP 0375388 and corresponding U.S. Pat. No. 5,081,151; glucosidase inhibitors, for example D-glucaro-1,5lactam and those described in document EP 0334586 and corresponding U.S. Pat. No. 4,975,441; glycosaminoglycanase and proteoglycanase inhibitors, for example L-galactono-1,4-lactone and those described in document EP 0277428 and corresponding U.S. Pat. No. 5,015,470; tyrosine kinase inhibitors, for example 1amido-1-cyano(3,4-dihydroxyphenyl)ethylene and those described in document EP 0403238 and corresponding U.S. Pat. No. 5,124,354, diazoxides, for example 7-(acetylthio)-4',5'-dihydrospiro[androst-4-ene-17,2'-(3H)furan]-3-one, 1,1-dioxide of 3-methyl-7-chloro[2H]-1,2,4-benzothiadiazine and spirooxazine; phospholipids, for example lecithin; salicylic acid and derivatives thereof, hydroxycarboxylic and keto carboxylic acids and esters thereof, lactones and their salts; anthralin, eicosa-5,8,11-trienoic acids and esters thereof and amides among others, minoxidil and derivatives, acetyl glucosamine, and mixtures thereof.

Agents for Reducing Bags Under the Eyes

Exemplary agents for reducing bags under the eye and dark circles include hesperidin methyl chalcone, dipeptide-2, *Passiflora incarnate* flower extract, linoleic acid, isolinoleic acid, peptides as described in U.S. 20100098769, and mixtures thereof.

Collagen Synthesis or Blood Circulation Enhancing Agents

Exemplary collagen synthesis or blood circulation enhancing agents include arginine, *Ascophyllum nodosum* extract, *Asparagopsis armata* extract, and mixtures thereof.

Antioxidants

Exemplary antioxidants include nordihydroguaiaretic acid, butylhydroxyanisole (BHA), butylhydroxytoluene (BHT), propyl gallate, erythorbic acid, sodium erythorbate, para-hydroxyanisole, tert-butylhydroquinone (TBHQ), 2,6,-di-tert-butyl-4methylphenol, gallic acid esters such as propyl gallate and octyl gallate, probucol, polyphenols, ascorbic acid and its salts, enzymes such as catalase, superoxide dismutase and peroxidases; citric acid, citrates, monoglyceride esters, calcium metabisulfite, lactic acid, malic acid, succinic acid, tartaric acid, vitamin A or β-carotene, vitamins E and C, tocopherols such as vitamin E acetate, ascorbic acid esters such as ascorbyl palmitate and ascorbyl acetate, zinc, copper, mannitol, reduced glutathione, carotenoids such as cryptoxanthin, astaxanthin and lycopene; cysteine, uric acid, carnitine, taurine, tyrosine, lutein, zeaxanthin, N-acetyl-cysteine, carnosine, γ-glutamylcysteine, quercetin, lactoferrin, dihydrolipoic acid, tea catechins, retinyl palmitate and derivatives thereof, bisulfate, metabisulfite and sodium sulfite, chromans, chromenes and their analogues, Lipochroman-6 [INCI: Dimethylmethoxy Chromanol], chelating agents of metals such as EDTA, sorbitol, phosphoric acid or dGlyage™ [INCI: Lysine HCl, Lecithin, Tripeptide-9 Citrulline]; extract of *Ginkgo Biloba*, plant extracts such as sage, pomegranate, rosemary, oregano, ginger, marjoram, cranberry, grape seed, tomato, green leaf tea and black leaf tea; oleoresin extract, extract of plants which contain phenols such as vanillin, ellagic acid and resveratrol; tertiary butylhydroquinone or mixtures thereof, metal salts with a valence of 2 such as selenium, cadmium, vanadium or zinc; α-lipoic acid, coenzyme Q, idebenone and derivatives thereof, and mixtures thereof.

Antihistamine Agents

Exemplary antihistamine agents include chlorpheniramine maleate, promethazine hydrochloride, cetirizine hydrochloride, and mixtures thereof.

UV Absorbers

Exemplary ultraviolet ray absorbers and agents capable of filtering UV rays include benzophenone derivatives such as 2,4-dihydroxybenzophenone, organic and mineral photoprotective agents active against A and/or B ultraviolet rays such as substituted benzotriazoles, substituted diphenylacrylates, organic nickel complexes, umbelliferone, urocanic acid, biphenyl derivatives, stilbene, 3-benzylidene camphor, and derivatives thereof such as 3-(4-methylbenzylidene)camphor; 4-aminobenzoic acid and derivatives thereof, 2-ethylhexyl 4-(dimethylamino)benzoate, 2-octyl 4-(dimethylamino)benzoate and amyl 4-(dimethylamino)benzoate; cinnamic acid derivatives such as benzyl cinnamate, cinnamic acid esters, such as 2-ethylhexyl 4-methoxycinnamate and diethylamino hydroxybenzoyl hexyl benzoate, propyl 4methoxycinnamate, isoamyl 4-methoxycinnamate, 2-ethylhexyl-2-cyano-3,3-diphenyl cinnamate (octocrylene); salicylic acid derivatives such as benzyl salicylate and salicylic acid esters, such as 2-ethylhexyl salicylate, 4-isopropylbenzyl salicylate, homonienthyl salicylate; benzophenone derivatives, such as 2-hydroxy-4-methoxybenzophenone, 2-hydroxy-4-methoxy-4'-methylbenzophenone, and 2,2'-dihydroxy-4-methoxybenzophenone; benzalmalonic acid esters, such as di-2-ethylhexyl 4methoxybenzalmalonate; triazine derivatives, such as 2,4,6-trianilino-(p-carbo-2'ethyl-1'-hexyloxy)-1,3,5-triazine, octyl triazone or diethylhexyl butamido triazone; propane-1,3-diones, such as 1-(4-tert-butylphenyI)-3-(4'-methoxyphenyl)propane-1,3dione; ketotricyclo(5.2.1.0)decane derivatives; 2-phenylbenzimidazole-5sulfonic acid; benzophenone sulfonic acid derivatives, such as 2hydroxy-4-methoxybenzophenone-5-sulfonic acid and its salts; 4(2oxo-3-bornylidenemethyl)benzenesulfonic acid, benzoyl methane derivatives, such as benzoyl methane 2methyl-5-(2-oxo-3-bornylidene)sulfonic acid, such as 1(4'-tert-butylphenyl)-3-(4'-methoxyphenyl) propane-1,3-dione, 4-tertbutyl-4'-methoxydibenzoylmethane, 1-phenyl-3-(4'-isopropylphenyl)-propane-1,3-dione, enamine compounds, anthranilates, silicons, benzimidazole derivatives, imidazolines, benzoyl derivatives, Chromabright™ [INCI: dimethylmethoxy chromanyl palmitate] and Preventhelia® [INCI: diaminopropionoyl tripeptide-33] both marketed by Lipotec, metal oxides such as zinc oxide, titanium, iron, zirconium, silicon, manganese, aluminum and cerium; silicates, talc, barium sulfate, zinc stearate, carbon nanotubes, and mixtures thereof.

Amino Acids and Their Salts

Exemplary amino acids include glycine, alanine, valine, leucine, isoleucine, serine, threonine, phenylalanine, tyrosine, tryptophan, cystine, cysteine, methionine, citrulline, proline, hydroxyproline, aspartic acid, asparagine, glutamic acid, glutamine, arginine, histidine, lysine, γ-aminobutyric acid, salts thereof and mixtures thereof. Example salts include glutamate, trisodium methylglycine diacetate (e.g., Trilon® M marketed by BASF), derivatives of amino acids which contain cysteine, in particular N-acetyl cysteine, ergothioneine or S-carboxymethylcysteine, and/or mixtures thereof.

Peptides and Commercial Formulations Containing Them

Exemplary peptides and commercial mixtures which contain them some of which are mentioned elsewhere herein for particular effects, and may include wheat peptides, soybean peptide, copper peptide GHKCu [INCI: Tripeptide-1], acetyl-glutamyl-methionyl-alanyl-isoleucine, acetyl-arginyl-phenylglycyl-phenylglycine, Bodyfensine™ [INCI: acetyl dipeptide-3 aminohexanoate], Relistase™ [INCI: acetylarginyltriptophyl diphenylglycine], acetyl-arginyl-phenylglycyl-valyl-glycine, acetyl-arginyl-phenylglycyl-valyl-phenylglycine, diaminopropionyl-alanyl-asparaginyl-histidine, acetyl-arginyl-asparaginyl-histidyl-citrulline-amide, Aldenine® [INCI: hydrolyzed wheat protein, hydrolyzed soy protein, tripeptide-1], Decorinyl® [INCI: tripeptide-10 citrulline], Serilesine® [INCI: hexapeptide-10], Peptide AC29 [INCI: acetyl tripeptide-30 citrulline], Vilastene™ [INCI: lysine HCl, lecithin, tripeptide-10 citrulline], dGlyage™ [INCI: Lysine HCl, Lecithin, Tripeptide-9 Citrulline], Eyeseryl® [INCI: acetyl tetrapeptide-5], Preventhelia® [INCI: diaminopropionoyl tripeptide-33], Argireline® [INCI: acetyl hexapeptide-8], SNAP-7 [INCI: acetyl heptapeptide-4], SNAP-8 [INCI: acetyl octapeptide-3], Leuphasyl® [INCI: pentapeptide-18], Trylagen® [INCI: Pseudoalteromonas ferment extract, hydrolyzed wheat protein, hydrolyzed soy protein, tripeptide-10 citrulline, tripeptide-1], Inyline™ [INCI: acetyl hexapeptide-30], Melatime™ [INCI: acetyl tripeptide-40], Thermostressine™ [INCI: acetyl tetrapeptide-22] and Liporeductyl® [INCI: caffeine, Butcher's broom (*Ruscus Aculeatus*) root extract, triethanolaminehydroiodide, carnitine, Ivy (Hedera helix) extract, escin, tripeptide-1] marketed by Lipotec, Matrixyl® [INCI: Palmitoyl Pentapeptide-4], Matrixyl® 3000 [INCI: palmitoyl tetrapeptide-7, palmitoyl oligopeptide], Dermaxyl® [INCI: palmitoyl oligopeptide], Calmosensine™ [INCI: acetyl dipeptide-1], Biopeptide CL™ [INCI: glyceryl polymethacrylate, propylene glycol, palmitoyl oligopeptide] and Biopeptide EL™ [INCI: palmitoyl oligopeptide] marketed by Sederma, pseudodipeptides, IP 2000 [INCI: dextran, trifluoroacetyl tripeptide-2] marketed by IEB and Atrium, Pepha®TIMP [INCI: Human Oligopeptide-20], ECMProtect® [INCI: Water (water), dextran, Tripeptide-2] and Melanostatine®-5 [INCI: dextran, nonapeptide-1] marketed by Atrium Innovations, TIMP-Peptide™ [proposed INCI: acetyl hexapeptide], Bronzing S. F. [proposed INCI: butyryl pentapeptide], BONTL Peptide [INCI: Palmitoyl Hexapeptide-19] and ECM Moduline [proposed INCI: Palmitoyl tripeptide-28] marketed by Infinitec Activos, IP2000™ [INCI: dextran, Trifluoroacetyl tripeptide-2] marketed by Institut Européen de Biologie Cellulaire, Syn®Coll [INCI: Palmitoyl Tripeptide-5] marketed by Pentapharm, Neutrazen™ [INCI: Water, butylene Glycol, dextran, Palmitoyl Tripeptide-8], ChroNOline™ [INCI: Caprooyl Tetrapeptide-3] and Thymulen-4 [INCI: Acetyl Tetrapeptide-2] marketed by Atrium Innovations/Unipex Group, Meliprene® [INCI: dextran, Acetyl Heptapeptide-1] and Melitane® [INCI: Acetyl Hexapeptide-1] marketed by Institut Européen de Biologie Cellulaire/Unipex Group, Skinasensyl™ [INCI: Acetyl Tetrapeptide-15] marketed by Laboratoires Serobiologiques/Cognis, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Syniorage™ [INCI: Acetyl Tetrapeptide-11], Dermican™ [INCI: Acetyl Tetrapeptide-9] marketed by Laboratoires Serobiologiques/Cognis, Kollaren® [INCI: Tripeptide-1, dextran] marketed by Institut Européen de Biologie Cellulaire, Collaxyl® IS [INCI: Hexapeptide-9], Laminixyl IS™ [INCI: Heptapeptide], Quintescine™ IS [INCI: Dipeptide-4], UCPeptide™ V [INCI: Pentapeptide] and AT Peptide™ IS [INCI: Tripeptide-3] marketed by Vincience/ISP, glutathione, carnosine and/or mixtures thereof; and peptides of pharmaceutical use, such as glucagon, leuprolide, goserelin, triptorelin, buserelin, nafarelin, deslorelin, histrelin, avorelin, abarelix, cetrorelix, ganirelix, degarelix, desmopressin, somatostatin and analogues of somatostatin such as octreotide, vapreotide and lanreotide, among others.

Specific examples of peptides include those described in the following U.S. Publications, patents, and international applications, where in each case, $R_1$ and $R_2$ are respective N and C peptide terminating groups which are generally not α-amino acids, examples of which are given in the respective patent documents:

U.S. Pat. No. 6,169,074, which describes an isolated excitationsecretory uncoupling peptide (ESUP) for inhibiting neurotransmitter secretion from neuronal cells, consisting of the amino acid sequence of SEQ ID NO.: 1 (170-EIDTQNRQIDRIMEKADSNKTRIDEANQRATKMLGSG-206, which is the amino acid sequence of the substrate binding domain of SNAP-25), SEQ ID NO.: 2 (170-EIDTQNRQIDRIMEKADSNK-189, which is the amino acid sequence of ESUP/E20h), SEQ ID NO.: 3 (181IMEKADSNKTRIDEANQRATKMLGSG-206, which is the amino acid sequence of ESUP/E26h), SEQ ID NO.: 4 (187SNKTRIDEANQRATKMLGSG-206, the amino acid sequence of ESUP/A20h), and SEQ. ID. NO.: 5 (Gln-Asn-Arg-Gln-Ile-Asp-Arg-Ile-Met-Glu-Lys-Ala-Asp-Ser-Asn-Lys, the amino acid sequence of an ESUP derived from SNAP-25). All residues correspond to substrate binding domain residues.

U.S. Pat. Nos. 7,015,192 and 7,473,679, which describe peptides having a sequence at least 3 and no more than 30 adjacent amino acids from the amino end of protein SNAP-25 and which is useful as neuronal exocytosis inhibitor, in particular, the synthetic peptide whose complete amino acid sequence is selected from the amino acid sequence of SEQ ID NO: 6 (Glu Glu Met Gln Arg Arg) and the amino acid sequence of SEQ ID NO: 7 (Glu Leu Glu Glu Met Gln Arg Arg Ala Asp Gln Leu Ala). The N-terminus of the peptide may be acetylated and the amino acid at the C-terminus of the peptide may be amidated.

U.S. Pat. No. 7,943,156, which describes peptides capable of increasing firmness of skin and delaying aging of skin. These XIKVAV peptides of general formula (III): X-SEQ ID NO. 8-Y:

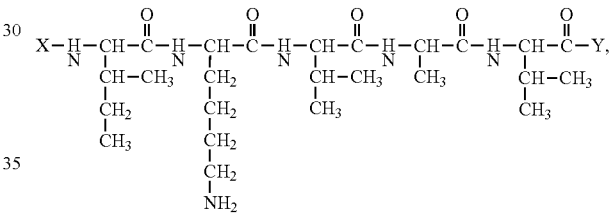

wherein X is selected from the group consisting of hydrogen, an amino acid and an acyl group and Y is selected from the group consisting of amino, hydroxyl and thiol. The XIKVAV peptides of general formula X-SEQ ID NO. 8-Y stimulate bioadhesion of cutaneous cells by increasing expression of bioadhesion peptides.

U.S. 20100021510, which describes a peptide capable of regulating neuronal exocytosis, of the general formula (IV): $R_1$-AA-$R_2$ its stereoisomers, mixtures thereof, and its cosmetically and pharmaceutically acceptable salts, wherein AA is a sequence of a least 3 and up to 40 adjacent amino acids contained in the amino acid sequence SEQ ID No.: 9 selected from SEQ ID NO.: 10 (MAEDADMRNELEEMQRRADQL), SEQ ID NO.: 11 (ADESLESTRRMLQLVEESKDAGI), SEQ ID NO.: 12 (ELEEMQRRADQLA), SEQ ID NO.: 13 (ELEEMQRRADQL), SEQ ID NO.: 14 (ELEEMQRRADQ), SEQ ID NO.: 15 (ELEEMQRRAD), SEQ ID NO.: 16 (ELEEMQRRA), SEQ ID NO.: 17 (ELEEMQRR), SEQ ID NO.: 18 (LEEMQRRADQL), SEQ ID No.: 19 (LEEMQRRADQ), SEQ ID NO.: 20 (LEEMQRRAD,), SEQ ID No.: 21 (LEEMQRRA,), SEQ ID NO.: 22 (LEEMQRR), SEQ ID NO.: 23 (EEMQRRADQL), SEQ ID NO.: 24 (EEMQRRADQ), SEQ ID NO.: 25 (EEMQRRAD), SEQ ID NO.: 26 (EEMQRRA), SEQ ID NO.: 27 (EEMQRR), SEQ ID NO.: 28 (LESTRRMLQLVEE), SEQ ID NO.: 29 (NKDMKEAEKNLT), SEQ ID NO: 30 (KNLTDL), SEQ ID NO.: 31 (IMEKADSNKTRIDEANQRATKMLGSG), SEQ ID NO.: 32 (SNKTRID- EANQRATKMLGSG), SEQ ID NO.: 33 (TRID-EANQRATKMLGSG), SEQ ID NO.: 34 (DEANQRATKMLGSG), SEQ ID NO.: 35 (NQRATKMLGSG) and SEQ ID NO.: 36 (QRATKMLGSG), SEQ ID NO.: 9 being Met Ala Glu Asp Ala Asp Met Arg Asn Glu Leu Glu Glu Met Gln Arg Ala Asp Gln Leu Ala Asp Glu Ser Leu Glu Ser Thr Arg Arg Met Leu Gln Leu Val Glu Glu Ser Lys Asp Ala Gly Ile Arg Thr Leu Val Met Leu Asp Glu Gln Gly Glu Gln Leu Glu Arg Ile Glu Glu Gly Met Asp Gln Ile Asn Lys Asp Met Lys Glu Ala Glu Lys Asn Leu Thr Asp Leu Gly Lys Phe Cys Gly Leu Cys Val Cys Pro Cys Asn Lys Leu Lys Ser Ser Asp Ala Tyr Lys Lys Ala Trp Gly Asn Asn Gln Asp Gly Val Val Ala Ser Gln Pro Ala Arg Val Val Asp Glu Arg Glu Gln Met Ala Ile Ser Gly Gly Phe Ile Arg Arg Val Thr Asn Asp Ala Arg Glu Asn Glu Met Asp Glu Asn Leu Glu Gln Val Ser Gly Ile Ile Gly Asn Leu Arg His Met Ala Leu Asp Met Gly Asn Glu Ile Asp Thr Gln Asn Arg Gln Ile Asp Arg Ile Met Glu Lys Ala Asp Ser Asn Lys Thr Arg Ile Asp Glu Ala Asn Gln Arg Ala Thr Lys Met Leu Gly Ser Gly.

U.S. 20100098769, which describes a peptide capable of reducing or removing bags formed under the eyes of general formula (V):

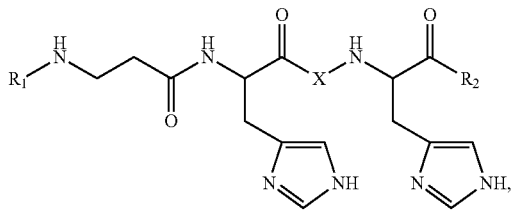

its stereoisomers, mixtures thereof, and its cosmetically and dermopharmaceutically acceptable salts, where X is selected from cysteinyl, seryl, threonyl and aminobutyryl.

U.S. 20110002969, which describes a peptide which includes only four amino acids and which is capable of inhibiting the activity of matrix metalloproteinases, of general formula (VI): R1-$AA_1$-$AA_2$-$AA_3$-$AA_4$-$R_2$ ($R_1$-(SEQ ID NO.: 37)-$R_2$), stereoisomers thereof, mixtures thereof and cosmetically or pharmaceutically acceptable salts thereof, wherein: $AA_1$ is -Arg-; $AA_2$ is selected from -His- and -Asn-; $AA_3$ is selected from -His- and -Arg-; $AA_4$ is-Cit-, Specific examples include $R_1$-Arg-His-His-Cit-$R_2$ ($R_1$-(SEQ ID NO.: 38)-$R_2$), $R_1$-Arg-Asn-Arg-Cit-$R_2$ ($R_1$-(SEQ ID NO.: 39)-$R_2$), and stereoisomers, mixtures thereof and/or cosmetic or pharmaceutical acceptable salts thereof.

U.S. 20090155317, which describes a peptide which includes only four amino acids and which is capable of reducing facial wrinkles, of general formula (VII):

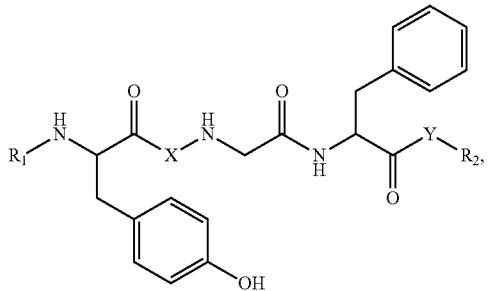

and cosmetically or dermopharmaceutically acceptable salts thereof, wherein: X and Y are selected from natural amino acids in their L- or D-form and non-encoded amino acids. Specific examples include peptides where X is glycyl, D-alanyl or D-seryl, and/or where Y is L-methionyl or L-leucyl.

U.S. 20110195102, which describes a peptide of only four amino acids, which is capable of inhibiting the activity of Reactive Carbonyl Species (RCS) with general formula (VIII): $R_1$-$AA_1$-$AA_2$-$AA_3$-$AA_4$-$R_2$ ($R_1$-SEQ ID NO.: 40)-$R_2$), its stereoisomers, mixtures thereof, and its cosmetically or pharmaceutically acceptable salts, wherein $AA_1$ is selected from -Lys-, -Orn-, -Dab-, -Dpr-, -Agl-, -3,4-dehydrolysine and -4,5-dehydrolysine; $AA_2$ is -Ala-; $AA_3$ is selected from -Asp-, -Ala-, -Asn-, -Glu- and -Pro-; and $AA_4$ is -His-. Specific examples include $R_1$-L-Dpr-D-Ala-L-Ala-L-His-$R_2$ ($R_1$-(SEQ ID NO.: 41)-$R_2$), $R_1$L-Dpr-D-Ala-L-Pro-L-His-$R_2$ ($R_1$-(SEQ ID NO.: 42)-$R_2$), $R_1$L-Dpr-L-Ala-L-Pro-L-His$R_2$ ($R_1$-(SEQ ID NO.: 43)-$R_2$), and stereoisomers, mixtures thereof and/or cosmetic or pharmaceutical acceptable salts thereof.

U.S. 20110300199, which describes a peptide having a maximum of seven amino acids which is capable of inhibiting elastase activity and/or stimulating collagen synthesis in the skin of general formula (IX): $R_1$-$W_p$-$X_n$-$AA_1$-$AA_2$-$AA_3$-$AA_4$-$Y_m$-$R_2$ ($R_1$-(SEQ ID NO.: 44)-$R_2$), its stereoisomers, mixtures thereof, and/or its cosmetically or pharmaceutically acceptable salts, wherein at least one of the amino acids $AA_1$, $AA_2$ and $AA_4$ is uncoded; $AA_1$ is selected from -Arg-, -Phg- and -Nle- or is absent; $AA_2$ is selected from -Ala-, -Phg-, -Cit- and -Nle-; $AA_3$ is selected from -Trp-, -Val- and -Tyr-; $AA_4$ is selected from -Phg- and -Gly-; W, X and Y are independently selected from the group consisting of coded and uncoded amino acids; and p, n and m each range between 0 and 1. Specific examples include R1-L-Arg-L-Nle-L-(or D-)-Phg-L-Tyr-L-(or D)-Phg$R_2$ ($R_1$-(SEQ ID No.: 45)-$R_2$), $R_1$-L-Arg-(or L-Nle or absent)-L-(or D)-Phg-L-Tyr-L-(or D)-Phg-$R_2$ ($R_1$-(SEQ ID No.: 46)-$R_2$), $R_1$-L-Arg-L-(or D-)-Phg-L-Val-L-(or D-)-Phg (or -L-Gly-)$R_2$ ($R_1$-(SEQ ID No.: 47)-$R_2$), and $R_1$-L-(or D-)-Phg-L-(or D-)-Phg-L-Trp-L-(or D-)-Phg-$R_2$ ($R_1$-(SEQ ID No.: 48)-$R_2$), and corresponding peptides wherein at least one of W, X, and Y is present, and stereoisomers, mixtures thereof and/or cosmetic or pharmaceutical acceptable salts thereof.

U.S. 20120021029, which describes a peptide having only three amino acids of general formula (X): R1-$AA_1$-$AA_2$-$AA_3$-$R_2$, its stereoisomers, mixtures thereof and/or its cosmetic or pharmaceutical acceptable salts, wherein: $AA_1$ and $AA_2$ are independently selected from -Tyr- and -Phe-; and $AA_3$ is selected from -Nle- and -Met-. Specific examples include $R_1$L-Tyr-L-Tyr-L-Met-$R_2$, $R_1$-L-Tyr-L-Phe-L-Met-$R_2$, and $R_1$-L-Tyr-L-Tyr-L-Nle-$R_2$, and stereoisomers, mixtures thereof and/or cosmetic or pharmaceutical acceptable salts thereof.

U.S. 20120121675, which describes a peptide of general formula (XI): $R_1$-$W_n$-$X_m$-$AA_1$-$AA_2$-$AA_3$-$AA_4$-$AA_5$-$AA_6$-$Y_p$-$Z_s$$R_2$ ($R_1$-(SEQ ID No.: 49)-$R_2$), its stereoisomers, mixtures thereof and/or its cosmetic or pharmaceutical acceptable salts, wherein $AA_1$ is selected from Asp, Glu and Pro; $AA_2$ is Asp; $AA_3$ is selected from Tyr and Arg; $AA_4$ is selected from Phe and Tyr; $AA_5$ is selected from Arg and Lys; $AA_6$ is selected from Leu and Met; W, X, Y and Z are independently selected from coded amino acids and non-coded amino acids; n, m, p and s independently have a value of between 0 and 1. Specific examples include 131-L-Glu-L-Asp-L-Tyr-L-Tyr-L-Arg-L-Leu-$R_2$ ($R_1$-(SEQ ID No.: 50)-$R_2$), $R_1$-L-Pro-L-Asp-L-Tyr-L-Tyr-L-Lys-L-Leu-$R_2$ ($R_1$-(SEQ ID No.: 51)-$R_2$), $R_1$-L-Glu-L-Asp-L-Arg-L-Phe-L-Arg-L-Met-$R_2$ ($R_1$-(SEQ ID No.: 52)-$R_2$), $R_1$-L-Glu-L-Asp-L-Tyr-L-Tyr-L-Arg-L-Met-$R_2$ (R1-(SEQ ID No.: 53)-$R_2$), and $R_1$-L-Pro-L-Asp-L-Tyr-L-Tyr-L-Arg-L-Met-$R_2$ ($R_1$-(SEQ ID No.: 54)-$R_2$), and corresponding peptides wherein at least one of W, X, Y and Z is present, and stereoisomers, mixtures thereof and/or cosmetic or pharmaceutical acceptable salts thereof.

U.S. 20130101662, which describes a peptide of general formula (XII): $R_1$-$W_n$-$X_m$-$AA_1$-$AA_2$-$AA_3$-$AA_4$-$Y_p$-$Z_1$-$R_2$ ($R_1$-(SEQ ID No.: 55)-$R_2$), its stereoisomers, mixtures thereof and/or its cosmetically or pharmaceutically acceptable salts, wherein: $AA_1$ is -His-; $AA_2$ is selected from the group consisting of -His-, -Leu- and -Pro-; $AA_3$ is -Leu-; $AA_4$ is selected from the group consisting of -Arg- and -Asn-; W, X, Y and Z are independently selected from amongst themselves from the group consisting of the codified amino acids and uncodified amino acids; n, m, p and q are independently selected from amongst themselves and have a value between 0 and 1; n+m+p+q is less or equal to 2. Specific examples include $R_1$-L-His-L-Leu-L-Leu-L-Arg-$R_2$ ($R_1$-(SEQ ID No.: 56)-$R_2$) and $R_1$-L-His-L-Pro-L-Leu-L-Arg-$R_2$ ($R_1$-(SEQ ID No.: 57)-$R_2$).

U.S. 20130309281, which describes a peptide of general formula (XIII):

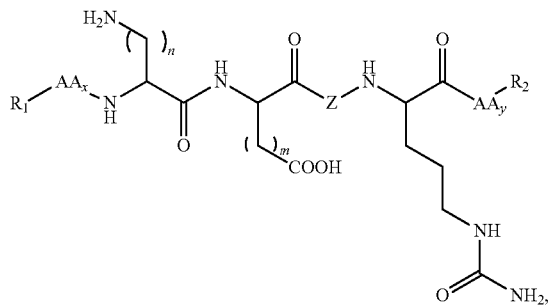

stereoisomers thereof, mixtures thereof, and cosmetically and dermopharmaceutically acceptable salts thereof, wherein: Z is selected from the group consisting of alanyl, alto-isoleucyl, glycyl, isoleucyl, isoseryl, isovalyl, leucyl, norleucyl, norvalyl, prolyl, seryl, threonyl, allo-threonyl or valyl; n and m range independently from one another between 1 and 5; AA is selected from the group consisting of natural encoded amino acids in their L- or D-form and non-encoded amino acids; x and y range independently from one another between 0 and 2. Specific examples include those where wherein Z is L-isoleucyl, L-threonyl or L-valyl and wherein x and y are 0, and stereoisomers, mixtures thereof and/or cosmetic or pharmaceutical acceptable salts thereof.

U.S. 20140120141, which describes a peptide of general formula (XIV): $R_1$-$W_n$-$X_m$-$AA_1$-$AA_2$-$AA_3$-$AA_4$-$AA_5$-$AA_6$-$Y_p$-$Z_q$-$R_2$ ($R_1$-(SEQ ID No.: 58)-$R_2$) its stereoisomers, mixtures thereof and/or its cosmetic or pharmaceutical acceptable salts, wherein: $AA_1$ is selected from the group consisting of -Ser-, -Thr- and -Tyr-; $AA_2$ is selected from the group consisting of -Pro- and -Val-; $AA_3$ is -Ala-; $AA_4$ is selected from the group consisting of -Glu-, -Gly- and -Val-; $AA_5$ is -Gly-; $AA_6$ is selected from the group consisting of -Gln-, -Gly-, -His- and -Pro-; W, X, Y, Z are amino acids and are independently selected from amongst themselves; n, m, p and q are independently selected from amongst themselves and have a value of 0 or 1; n+m+p+q is lower than or equal to 2. Specific examples include $R_1$-L-Tyr-L-Pro-L-Ala-L-Glu-L-Gly-L-Gln-$R_2$, ($R_1$-(SEQ ID No.: 59)-$R_2$) $R_1$-L-Ser-L-Val-L-Ala-L-Val-L-Gly-L-Gln-$R_2$ ($R_1$-(SEQ ID No.: 60)-$R_2$), and $R_1$L-Ser-L-Pro-L-Ala-L-Gly-L-Gly-L-Pro-$R_2$ ($R_1$-(SEQ ID No.: 61)-$R_2$), and stereoisomers, mixtures thereof and/or cosmetic or pharmaceutical acceptable salts thereof.

U.S. 20150183823, which describes peptides of general formula (XV): $R_1$-$AA_1$-$AA_2$-$AA_3$-$R_2$, where $AA_1$ is selected from -Tyr- and -Phe-, $AA_2$ is -Tyr-, and $AA_3$ is selected from -Nle- and -Met-, its stereoisomers, mixtures thereof and/or their cosmetically or pharmaceutically acceptable salts, which is suited to the treatment and/or care of conditions, disorders and/or diseases of the skin and/or hair by stimulating cyclic adenosine monophosphate synthesis (cAMP). Specific examples include $R_1$-L-Tyr-L-Tyr-L-Met-$R_2$, $R_1$L-Tyr-L-Phe-L-Met-$R_2$, and $R_1$L-Tyr-L-Tyr-L-Nle-$R_2$, and stereoisomers, mixtures thereof and/or cosmetic or pharmaceutical acceptable salts thereof.

WO2014/086785 (and U.S. Ser. No. 14/649,747; Filed Jun. 4, 2015), which describes compounds capable of accelerating the DNA protection and repair processes of general formula (XVII):

$R_1$-$W_n$-$X_m$-$AA_1$-$AA_2$-$AA_3$-$AA_4$-$AA_5$-$AA_6$-$Y_p$$Z_q$-$R_2$ (R,-(SEQ ID No.: 62)-$R_2$), its stereoisomers, mixtures thereof and/or its cosmetically or pharmaceutically acceptable salts, wherein $AA_1$ is -Tyr-; $AA_2$ is selected from -Asn-, -His-, -Tyr- and -Glu-; $AA_3$ is selected from -Lys-, -Ser- and -Pro-; $AA_4$ is selected from -Gly-, -Leu-, -Lys- and -His-; $AA_5$ is selected from -Gln- and -Asn-; $AA_6$ is -Val-; W, X, Y, Z are independently selected from amino acids. n, m, p and q independently have a value of 0 or 1; n+m+p+q is smaller than or equal to 2.

WO2014/170347 (and U.S. application Ser. No. 14/783,689, filed Oct. 9, 2015), which describes a compound of general formula (XVI):

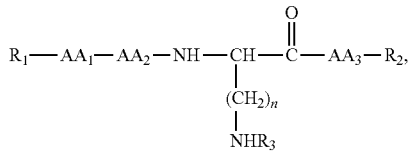

its stereoisomers, mixtures thereof and/or its cosmetic or pharmaceutical acceptable salts, wherein $AA_1$ is selected from -Asp-, -Glu-, -Asn-, -Gln-, -Lys- and -Gly-, $AA_2$ is selected from -Val-, -Leu-, -Ile-, -Met-, -Cit-, -His-, -Thr- and -Gln-; $AA_3$ is selected from -Tyr-, -Trp- and 4-Abz; n is selected from 1, 2, 3 and 4, $R_3$ is selected from H and -$AA_2$-$AA_1$-$R_1$, $R_1$ is selected from H, a polymer derived from polyethylene glycol, substituted or unsubstituted non-cyclic aliphatic groups, substituted or unsubstituted alicyclyl groups, substituted or unsubstituted heterocyclyl groups, substituted or unsubstituted heteroarylalkyl groups, substituted or unsubstituted aryl groups, substituted or unsubstituted aralkyl groups and $R_6$—CO—, wherein $R_6$ is selected from H, substituted or unsubstituted non-cyclic aliphatic groups, substituted or unsubstituted alicyclyl groups, substituted or unsubstituted aryl groups, substituted or unsubstituted aralkyl groups, substituted or unsubstituted heterocyclyl groups and substituted or unsubstituted heteroarylalkyl groups; R2 is selected from —$NR_4R_5$, —$OR_4$ and —$SR_4$, wherein $R_4$ and $R_5$ are independently selected from H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and $R_1$ and/or $R_2$ are not α-amino acids.

Vitamins

Example vitamins and factors acting like a vitamin include vitamin A and analogues thereof such as retinol and retinoic acid, carotenoids such as a-carotene and (3-carotene, vitamin $B_1$ and analogues thereof such as thiamines, vitamin B2 and analogues thereof such as riboflavin, vitamin $B_6$ and analogues thereof such as pyridoxine, vitamin B12 and analogues thereof such as cyanocobalamin, folic acid, nicotinic acid, pantothenic acid, vitamin C and analogues thereof such as L-ascorbic acid, vitamin D and analogues thereof such as ergocalciferol and cholecalciferol, vitamin E and analogues thereof such as d-α-tocopherol and γ-tocopherol, Coenzyme Q10, vitamin K and analogues thereof, carnitine, ferulic acid, a-lipoic acid, orotic acid, and mixtures thereof.

In one specific embodiment, the vitamins are selected from hydrosoluble vitamins, such as vitamin C, vitamin B1, vitamin B2, vitamin B3, vitamin B5, vitamin B6, vitamin B7, vitamin B9, vitamin B12, carnitine and/or mixtures thereof.

Free Radical Scavengers, Anti-Atmospheric Pollution Agents, and Reactive Carbonyl Species Scavengers Exemplary free radical scavengers and/or anti-atmospheric pollution agents, and/or reactive carbonyl species scavengers include tea extract, olive leaf extract, extract of Rosmarinus officinalis or extract of Eichhornia crassipes, benzopyrenes, vitamin C and derivatives thereof, vitamin E and derivatives thereof, in particular tocopheryl acetate, ascorbyl glycoside, phenols and polyphenols, in particular tannins, tannic acid and ellagic acid, gallocatechol, anthocyanins, chlorogenic acid, stilbenes, indoles, cysteine-containing amino acid derivatives, in particular N-acetylcysteine, ergothioneine, S-carboxymethylcysteine, chelating agents, in particular ethylene diamine tetraacetic acid (EDTA) trisodium ethylenediamine hydroxyethyl triacetate, sodium citrate, gluconic acid, phytic acid, sodium polyphosphate, sodium metaphosphate and ethylenediamines, carotenoids, bioflavonoids, ubiquinone, idebenone, catalase, superoxide dismutase, lactoperoxidase, glutathione peroxidase, glutathione, benzylidene camphor, pidolates, lignans, melatonin, oryzanol, carnosine and derivatives thereof, GHK [INCI: tripeptide-1] and its salts and/or derivatives, Aldenine® [INCI: hydrolyzed wheat protein, hydrolyzed soy protein, tripeptide-1], Preventhelia® [INCI: diaminopropionoyl tripeptide-33], diaminopropionyl-alanyl-asparaginyl-histidine, and Lipochroman™-6 [INCI: dimethylmethoxy chromanol] marketed by Lipotec, and mixtures thereof.

Hydrophilic Cosmetic, Pharmaceutical and Alimentary Active Agents

Examples of hydrophilic cosmetic, pharmaceutical and/or alimentary active agents include amino acids, peptides, proteins, hydrolyzed proteins, enzymes, hormones, vitamins, mineral salts, sugars, nucleotides, nucleic acids, molecules and extracts of biological and biotechnological origin, vaccines, synthetic or partially synthetic hydrophilic molecules and/or mixtures thereof.

Exemplary proteins, hydrolyzed protein, enzymes and hormones, as well as the commercial mixtures which contain them, include Elhibin® [INCI: glycine soja (soybean) protein], Preregen® [INCI: glycine soja (soybean) protein, oxidoreductases] and Regu®-Age [INCI: hydrolyzed rice bran protein, glycine soja (soybean) protein, oxidoreductases] marketed by Pentapharm/DSM, cadherins, integrins, selectins, hyaluronic acid receptors, immunoglobulins, fibroblast growth factor, connective tissue growth factor, platelet-derived growth factor, vascular endothelial growth factor, epidermal growth factor, insulin-like growth factor, keratinocyte growth factors, colony-stimulating growth factors, transforming growth factor-beta, tumor necrosis factor-alpha, interferons, interleukins, matrix metalloproteinases, receptor protein tyrosine phosphatases, hydrolyzed vegetable proteins such as hydrolyzed wheat protein, hydrolyzed soy protein or hydrolyzed whey protein, hydrolyzed vegetable protein, Collalift® [INCI: hydrolyzed malt extract] marketed by Coletica/Engelhard, Colhibin PF® [INCI: hydrolyzed rice protein] marketed by Pentapharm, Cytokinol® LS [INCI: hydrolyzed casein, hydrolyzed yeast protein, lysine HCL] marketed by Laboratoires Serobiologiques/Cognis, Liftline® [INCI: hydrolyzed wheat protein] and Ridulisse C® [hydrolyzed soy protein] marketed by Silab, catalase, superoxide dismutase, lactoperoxidase, glutathione peroxidase, lactoprotein, casein, lactoperoxidase, lysozyme, glycosidases, stratum corneum chymotryptic enzyme (SCCE); proteases such as trypsin, chymotrypsin, sutilain, papain and bromelain; DNA repair enzymes such as photolyase or T4 endonuclease V, lipase, luteinizing hormone (LH), follicle-stimulating hormone (FSH), growth hormone, insulin, and mixtures thereof.

Exemplary extracts of biological or biotechnological origin, which can be chemically modified, as well as the commercial mixtures which contain them, include vegetable extracts, marine extracts, cell extracts and extracts produced by microorganisms.

Exemplary vegetable extracts include hydrosoluble vegetable extracts, for example hydrosoluble extracts of chamomile, ivy, lemon, ginseng, raspberry, *Roast amaranth, Rehmanniae radix*, gardenia, carrot, orange, peach, pineapple, gentian, hibiscus flower, walnut leaf, pumpkin, peony, quinoa, boldo, rough bindweed, salvia, pomegranate, oregano, ginger, marjoram, cranberry, grape, tomato, green tea, black tea, aloe vera (*Aloe Barbadensis*), *Sophora japonica*, papaya, pineapple, pumpkin, sweet potato, *Bupleurum chinensis, Cecropia obtusifolia, Celosia cristata, Centella asiatica, Chenopodium quinoa, Chrysanthellum indicum, Citrus aurantium amara, Coffea arabica, Coleus Forskohlii, Commiphora myrrha, Crithmum maritimum, Eugenia caryophyllus, Ginkgo biloba, Hedera helix* (ivy), *Hibiscus sabdariffa, Ilex paraguariensis, Laminaria digitata, Nelumbium speciosum, Paullinia cupana, Peumus boldus, Phyllacantha fibrosa, Prunella vulgaris, Prunus amygdalus dulcis, Ruscus aculeatus* (Butcher's broom extract), *Sambucus nigra, Spirulina platensis Algae, Uncaria tomentosa, Verbena Officinalis, Opuntia ficus-indica, Salix alba, Lupinus* spp., *Secale cereale, Tussilago farfara, Achillea millefolium, Azadirachta indica, Osmunda japonica, Artocarpus incisus, Bidens pilosa, Broussonetia papyrifera, Chlorella vulgaris, Cimicifuga racemosa, Emblica officinalis, Glycyrrhiza glabra, Glycyrrhiza uralensis, Ilex purpurea, Ligusticum lucidum, Ligusticum wallichii, Mitracarpus scaber, Morinda citrifolia, Morus alba, Morus bombycis, Naringi crenulata, Prunus domestica, Radix pseudostellaria, Rumex crispus, Rumex occidentalis, Sapindus mukorossi, Saxifraga sarmentosa, Scutellaria Galericulata, Sedum sarmentosum Bunge, Stellaria medica, Triticum Vulgare, Uva ursi, Withania somnifera, Aristolochia clematis, Rosa moschata, Echinacea angustifolia, Symphytum officinale, Equisetum arvense, Hypericum perforaturn, Mimosa tenuiflora, Persea gratissima, Prunus africana, Tormentilla erecta, Solanum tubero-*

*sum, Rosmarinus officinalis, Vaccinium angustifolium, Macrocystis pyrifera algae, Padina pavonica, Malpighia puniciflolia, Cynara scolymus, Gossypium herbaceum, Panicum miliaceum, Morus nigra, Sesamum indicum, Glycine soja, Triticum vulgare, Glycine Max* (soy), malt, flax, red clover, kakkon-to, white lupine, hazelnut, maize, beech tree shoots, *Trifolium pratense* (red clover), *Phormium tenax* (New Zealand flax), *Cinnamomum verum, Laminaria saccharina, Spiraea ulmaria*, Nettle Root, *Pygeum africanum, Avena sativa, Arnica montana, Cinchona succirubra, Eugenia caryophyllata, Humulus lupulus, Hypericum perforatum, Mentha piperita, Rosmarinus officinalis, Thymus vulgaris*, plant extract of the genus *Silybum*, extract of legume seeds, extracts of red algae from the genus *Porphyra*, Phytovityl C® [INCI: water, *Zea Mays* extract] marketed by Solabia, Micromerol™ [INCI: Pyrus Malus extract] and heather extract [INCI: *Calluna vulgaris* extract] marketed by Coletica/Engelhard/BASF, Proteasyl® TP LS8657 [INCI: *Pisum sativum* extract] marketed by Laboratoires Serobiologiques/Cognis, Radicaptol™ [INCI: propylene glycol, water, *Passiflora incarnata* Flower extract, *Ribes nigrum* (blackcurrant) leaf extract, *Vitis vinifera* (grape) leaf extract] marketed by Solabia and ViaPure™ Boswellia [INCI: olibanum (*Boswellia serrata*) extract] marketed by Soliance, EquiStat™ [INCI *Pyrus malus* fruit extract, glycine soja seed extract] marketed by Coletica/Engelhard, Litchiderm™ [INCI: *Litchi chinensis* pericarp extract] and Arganyl™ [INCI: Argania spinosa leaf extract] marketed by Laboratories Serobiologiques/Cognis, Dakaline™ [INCI: *Prunus amygdalus dulcis, Anogeissus leiocarpus* bark extract] marketed by Soliance, Actimp 1.9.3® [INCI: hydrolyzed lupine protein] marketed by Expanscience® Laboratoires, Pronalen® Firming HSC [INCI: *Triticum vulgare, Silybum marianum*, glycine soy, *Equisetum arvense, Alchemilla vulgaris, Medicago sativa, Raphanus sativus*] and Polyplant® Firming [INCI: coneflower, *Centella asiatica*, fucus, fenugreek] marketed by Provital, Lanablue® [INCI: sorbitol, algae extract] marketed by Atrium Innovations, Firmiderm® LS 9120 [INCI: *Terminalia catappa* leaf extract, *Sambucus nigra* flower extract, PVP, tannic acid] marketed by Laboratoires Serobiologiques/Cognis, among others.

The amount of hydrophilic active ingredient contained in the face mask or body patch may be from 0.00001 to 50 wt. % of the total weight of the mask (on an unhydrated basis), such as at least 0.0001 wt. %, or at least 0.001 wt. %, or at least 0.01 wt. %, and may be up to 40 wt. %, or up to 30 wt. %, or up to 10 wt. %.

Agents Inhibiting Elastin Degradation

Exemplary agents inhibiting elastin degradation include Elhibin® [INCI: glycine soja (Soybean) protein], Preregen® [INCI: glycine soja (soybean) protein, oxidoreductases] or Regu®-Age [INCI: hydrolyzed rice bran protein, glycine soja (Soybean) protein, oxidoreductases] marketed by Pentapharm/DSM, Juvenesce [INCI: ethoxydiglicol and caprylic triglyceride, retinol, ursolic acid, phytonadione, ilomastat], Micromerol™ [INCI: *Pyrus Malus* extract], heather extract [INCI: *Calluna vulgaris* extract], Extracellium® [INCI: hydrolyzed potato protein] or Flavagrum™ PEG [INCI: PEG-6 isostearate, hesperetin laurate] marketed by Coletica/Engelhard/BASF, Proteasyl® TP LS 8657 [INCI: *Pisum sativum* extract] marketed by Laboratoires Sérobiologiques/Cognis, Relistase™ [INCI: acetylarginyltriptophyl diphenylglycine] marketed by Lipotec, Sepilift™ DPHP [INCI: dipalmitoyl hydroxyproline] marketed by Seppic, Vitaderm® [INCI: alcohol, water, glycerin, hydrolyzed rice protein, *Ilex aquifolium* extract, sodium ursolate, sodium oleanolate] marketed by Rahn, Gatuline® Age Defense 2 [INCI: *Juglans regia* (walnut) seed extract] marketed by Gattefossé, IP 2000 [INCI: dextran, trifluoroacetyl tripeptide-2] marketed by IEB and Atrium, Radicaptol™ [INCI: propylene glycol, water, *Passiflora incarnata* flower extract, *Ribes nigrum* (blackcurrant) leaf extract, *Vitis vinifera* (grape) leaf extract] marketed by Solabia or ViaPure™ Boswellia [INCI: olibanum (*Boswellia serrata*) extract] marketed by Soliance, and mixtures thereof.

Agents Stimulating Dermal or Epidermal Macromolecular Synthesis

Exemplary agents stimulating dermal or epidermal macromolecular synthesis include agents stimulating collagen synthesis, agents stimulating elastin synthesis, agents stimulating decorin synthesis, agents stimulating laminin synthesis, agents stimulating chaperone synthesis, agents stimulating sirtuin synthesis, agents stimulating hyaluronic acid synthesis, agents stimulating aquaporin synthesis, agents stimulating fibronectin synthesis, agents inhibiting collagen degradation, agents inhibiting elastin degradation, agents inhibiting serine proteases such as leukocyte elastase or cathepsin G, agents stimulating fibroblast proliferation, agents stimulating adipocyte proliferation, agents stimulating adipocyte differentiation, agents stimulating angiogenesis, agents stimulating glycosaminoglycan synthesis, DNA repair agents and/or DNA protecting agents, for example extracts of *Centella asiatica, Saccharomyces cerevisiae, Solanum tuberosum, Rosmarinus officinalis, Vaccinium angustifolium*, extract of the algae *Macrocystis pyrifera, Padina pavonica*, extract of the plants soy, malt, flax, sage, red clover, kakkon-to, white lupine, hazelnut extract, corn extract, yeast extract, extract of beech tree shoots, extract of leguminosae seeds, extract of plant hormones such as gibberellins, auxins or cytokinins among others, or extract of zooplankton Salina, the product of milk fermentation with *Lactobacillus Bulgaricus*, asiaticosides and derivatives thereof, vitamin C and derivatives thereof, cinnamic acid and derivatives thereof, Matrixyl® [INCI: palmitoyl pentapeptide-3], Matrixyl® 3000 [INCI: palmitoyl tetrapeptide-3, palmitoyl oligopeptide] or Biopeptide CL™ [INCI: glyceryl polymethacrylate, propylene glycol, palmitoyl oligopeptide] marketed by Sederma, Antarcticine® [INCI: Pseudoalteromonas ferment extract], Decorinyl® [INCI: tripeptide-10 citrulline], Serilesine® [INCI: hexapeptide-10], Lipeptide [INCI: hydrolyzed vegetable protein], Aldenine® [INCI: hydrolyzed wheat protein, hydrolyzed soy protein, tripeptide-1], Peptide AC29™ [INCI: acetyl tripeptide-30 citrulline], acetyl-arginyl-phenylglycyl-tryptophyl-phenylglycine, acetyl-arginyl-phenylglycyl-valyl-glycine, or acetyl-arginyl-phenylglycyl-valyl-phenylglycine, marketed by Lipotec, Drieline® PF [INCI: yeast betaglucan] marketed by Alban Muller, Phytovityl Co [INCI: water, *Zea Mays* extract] marketed by Solabia, Collalift® [INCI: hydrolyzed malt extract] marketed by Coletica/Engelhard, Phytocohesine® PSP [proposed INCI: sodium beta-sitosteryl sulfate] marketed by Seporga, minerals such as calcium among others, retinoids and derivatives thereof, isoflavonoids, carotenoids, in particular lycopene, pseudodipeptides, retinoids and derivatives thereof such as retinol and retinyl palmitate, heparinoids, and mixtures thereof.

Matrix Metalloproteinase-Inhibiting Agents

Exemplary matrix metalloproteinase-inhibiting agents include ursolic acid, isoflavones such as genistein, quercetin, carotenoids, lycopene, soy extract, cranberry extract, rosemary extract, *Trifolium pratense* (red clover) extract, *Phormium tenax* (New Zealand flax) extract, kakkon-to extract, sage extract, retinol and derivatives thereof, retinoic acid and derivatives thereof, sapogenins such as diosgenin, hecogenin, smilagenin, sarsapogenin, tigogenin, yamogenin and yuccagenin, Collalift® [INCI: hydrolyzed malt extract], Juvenesce [INCI: ethoxydiglicol and caprylic triglyceride, retinol, ursolic acid, phytonadione, ilomastat] and EquiStat™ [INCI *Pyrus malus* fruit extract, glycine soja seed extract] marketed by Coletica/Engelhard, Pepha®-TIMP [INCI: human oligopeptide-20], Regu®Age [INCI: hydrolyzed rice bran protein, glycine soja protein, oxidoreductases] and Colhibin™ [INCI: hydrolyzed rice protein] marketed by Pentapharm, Lipeptide [INCI: hydrolyzed vegetable protein], Peptide AC29 [INCI: acetyl tripeptide-30 citrulline], and acetyl-arginyl-asparaginyl-histidyl-citrulline-amide marketed by Lipotec, Litchiderm™ [INCI: *Litchi chinensis* pericarp extract] and Arganyl™ [INCI: *Argania spinosa* leaf extract] marketed by Laboratories Serobiologiques/Cognis, MDI Complex® [INCI: glycosaminoglycans] and ECM-Protect® [INCI: water, dextran, tripeptide-2] marketed by Atrium Innovations, Dakaline™ [INCI: *Prunus amygdalus dulcis, Anogeissus leiocarpus* bark extract] marketed by Soliance, Homeostatine™ [INCI: *Enteromorpha compressa, Caesalpinia spinosa*] marketed by Provital, TIMP-Peptide™ [proposed INCI: acetyl hexapeptide] and ECM Moduline™ [proposed INCI: palmitoyl tripeptide] marketed by Infinitec Activos, IP2000 [INCI: dextran, trifluoroacetyl tripeptide-2] marketed by Institut Européen de Biologie Cellulaire, Actimp 1.9.3® [INC!: hydrolyzed lupine protein] marketed by Expanscience Laboratories, Vitaderm® [INCI: alcohol, water, glycerin, hydrolyzed rice protein, ilex aquifolium extract, sodium ursolate, sodium oleanolate] marketed by Rahn, adapalene, tetracyclines and derivatives thereof such as minocycline, rolitetracycline, chlortetracycline, metacycline, oxytetracycline, doxycycline, demeclocycline and their salts, Batimastat [BB94; [4-(N-hydroxyamino)-2R-isobutyl-3S-(thiophene-2-ylthiomethyl) succinyl]-L-phenylalanine-N-methylamide], Marimastat™ [BB2516; [2S-[N4(R*),2R*,3S]]-N4[2,2-dimethyl-1-[methylaminocarbonyl]propyl]-N1,2-dihydroxy-3-(2-methylpropyl)butanediamide], and mixtures thereof.

Firming, Redensifying, and Restructuring Agents

Exemplary firming and/or redensifying and/or restructuring agents include extracts of *Malpighia puniciftolia, Cynara scolymus, Gossypium herbaceum, Aloe Barbadensis, Panicum miliaceum, Morus nigra, Sesamum indicum, Glycine soja, Triticum vulgare,* Pronalen® Firming HSC [INCI: *Triticum vulgare, Silybum marianum,* glycine soy, *Equisetum arvense, Alchemilla vulgaris, Medicago sativa, Raphanus sativus*] and Polyplant® Firming [INCI: Coneflower, *Centella Asiatica*, Fucus, Fenugreek] marketed by Provital, Lanablue® [INCI: sorbitol, algae extract] marketed by Atrium Innovations, Pepha®-Nutrix [INCI: natural nutrition factor] marketed by Pentapharm, vegetable extracts which contain isoflavones, Biopeptide EL™ [INCI: palmitoyl oligopeptide], Biopeptide CL™ [INCI: palmitoyl oligopeptide], Vexel® [INCI: water, propylene glycol, lecithin, caffeine, palmitoyl carnitine], Matrixyl® [INCI: palmitoyl pentapeptide-3], Matrixyl® 3000 [INCI: palmitoyl tetrapeptide-3, palmitoyl oligopeptide] and Bio-Bustyl™ [INCI: glyceryl polymethacrylate, Rahnella soy protein ferment, water, propylene glycol, glycerin, PEG-8, palmitoyl oligopeptide] marketed by Sederma, Dermosaccharides® HC [INCI: glycerin, water, glycosaminoglycans, glycogen], Aglycal® [INCI: mannitol, cyclodextrin, glycogen, *Arctostaphylos uva ursi* leaf extract], Cytokinol® LS [INCI: hydrolyzed casein, hydrolyzed yeast protein, lysine HCl] and Firmiderm® LS 9120 [INCI: *Terminalia catappa* leaf extract, *Sambucus Nigra* Flower extract, PVP, tannic acid] marketed by Laboratoires Serobiologiques/Cognis, Liftline® [INCI: hydrolyzed wheat protein], Raffermine® [INCI: hydrolyzed soy flour] and Ridulisse C® [hydrolyzed soy protein] marketed by Silab, Serilesine® [INCI: hexapeptide-10], Decorinyi™ [INCI: tripeptide-10 citrulline], Trylagen® [INCI: Pseudoalteromonas ferment extract, hydrolyzed wheat protein, hydrolyzed soy protein, tripeptide-10 citrulline, tripeptide-1], marketed by Lipotec, Ursolisome® [INCI: lecithin, ursolic acid, atelocollagen, xanthan gum, sodium chondroitin sulfate] and Collalift® [INCI: hydrolyzed malt extract] marketed by Coletica/Engelhard, Syn®-Coll [INCI: palmitoyl tripeptide-5] marketed by Pentapharm, Hydriame® [INCI: water, glycosaminoglycans, sclerotium gum] marketed by Atrium Innovations, IP2000 [INCI: dextran, trifluoroacetyl tripeptide-2] marketed by Institut Europeen de Biologie Cellulaire, and mixtures thereof.

Anti-Glycation Agents

Exemplary anti-glycation agents include Vaccinium angustifolium extracts, ergothioneine and derivatives thereof, lysine, Aldenine® [INCI: hydrolyzed wheat protein, hydrolyzed soy protein, tripeptide-1], Vilastene™ [INCI: lysine HCl, lecithin, tripeptide-10 citrulline], dGlyage™ [INCI: lysine HCl, lecithin, tripeptide-9 citrulline] and Eyeseryl® [INCI: acetyl tetrapeptide-5] marketed by Lipotec, hydroxystilbenes and derivatives thereof, resveratrol, 3,3',5,5'-tetrahydroxystilbene, and mixtures thereof.

5α-Reductase Inhibiting Agents

Exemplary 5α-reductase inhibiting agents include extracts of *Cinnamomum verum, Laminaria saccharina, Spiraea ulmaria*, Nettle Root, *Pygeum africanum, Avena Sativa, Serenoa repens*, extracts of the plants *Arnica montana, Cinchona succirubra, Eugenia caryophyllata, Humulus lupulus, Hypericum perforatum, Mentha piperita, Rosmarinus officinalis, Salvia officinalis,* and *Thymus vulgaris*, extract of plants of the genus *Silybum*, extracts of plants which contain sapogenins and in particular extract of plants of the genus *Dioscorea*, phytosterols, retinoids and in particular retinol, sulfur and derivatives thereof, zinc salts and in particular zinc lactate, zinc gluconate, zinc pidolate, zinc carboxylate, zinc salicylate and zinc cysteate, selenium chloride, vitamin B6, pyridoxine, caprylol glycine, sarcosine, finasteride, dutasteride, izonsteride, turosteride and their salts, and mixtures thereof.

Lysyl- and/or Prolyl-Hydroxylase-Inhibiting Agents

Exemplary lysyl- and/or prolyl-hydroxylase-inhibiting agents include 2,4-diaminopyrimidine 3-oxide, 2,4-diamino-6-piperidinopyrimidine 3-oxide, and mixtures thereof.

Defensin Synthesis-Stimulating Agents

Exemplary defensin synthesis-stimulating agents include extracts of or hydrolyzed *Aloe Vera*, Roast amaranth, *Rehmanniae radix*, arnica, gardenia, carrot, orange, peach, pineapple, mint, gentian, hibiscus flower, walnut tree leaf, calabaza, peony, quinoa, boldo, rough bindweed, sunflower, elderberry, seaweed, hydrolyzed corn, hydrolyzed soy, hydrolyzed rice, valine and its isomers and derivatives, calcium and its salts, α-MSH and fragments contained in the amino acid sequence of α-MSH, vitamin A and its derivatives and precursors, vitamin D3 and its derivatives, jasmonic acid, fumaric acid, malic acid, citric acid, ascorbic acid, lactic acid, acetic acid, adipic acid, tartaric acid, cinnamic acid, glutamic acid, succinic acid, inulin, alkyl glucosides, poly-D-glutamic acid, glycine, L-methionine, L-alanine, L-citrulline, lactoprotein, casein, lactoperoxidase, lysozyme, polyphenol, alkyl glucosides, *Lactobacillus* extract, fusobacteria extracts, non-photosynthetic and nonfruiting filamentous bacteria, Bodyfensine™ [INCI: acetyl dipeptide-3 aminohexanoate] marketed by Lipotec, and mixtures thereof.

Antiseptic Agents and Disinfectants

Exemplary antiseptic agents and disinfectants include those serving as bactericidal, bacteriostatic, antimicrobial, germicidal, fungicidal, fungistatic and/or germ inhibiting agents.

Examples of such agents include, macrolides, pyranosides, calcium channel blockers, for example cinnarizine and diltiazem; hormones, for example estril and analogues thereof, thyroxine and/or its salts, caprylyl glycol, imidazolidinyl urea, sodium 4-oxybenzoate methyl, methyl 4-hydroxybenzoate [INCI: methylparaben], ethyl 4-oxybenzoate, ethyl 4-hydroxybenzoate [INCI: ethylparaben], propyl 4-oxybenzoate, isopropyl 4oxybenzoate, propyl 4hydroxybenzoate [INCI: propylparaben], butyl 4oxybenzoate, butyl 4hydroxybenzoate [INCI: butylparaben], isobutyl 4hydroxybenzoate [INCI: isobutylparaben], 1,3bis(hydroxymethyl)-5,5dimethylimidazolidine-2,4dione [INCI: DMDM hydantoin], benzyl 4oxybenzoate, benzyl 4hydroxybenzoate [INCI: benzylparaben], benzyl alcohol, dehydroacetic acid, benzoic acid, sodium benzoate, potassium sorbate, dehydroacetic acid, sodium dehydroacetate sorbic acid, salicylic acid, formic acid, propionic acid, 2-bromo-2-nitropropane-1,3-diol, 3-p-chlorophenoxy-1,2-propanediol [INCI: chlorphenesin], dichlorobenzyl alcohol, iodopropynyl butylcarbamate, benzalkonium chloride, odorabsorbing fungicides such as zinc ricinoleate, cyclodextrins, benzethonium chloride, chlorhexidine, ethanol, propanol, 1,3-butanediol, 1,2-propylene glycol, undecylenic acid, dehydroacetic acid, N-methylmorpholine acetonitrile (MMA), isopropanol, methanol, 1,2-hexanediol, 1,2-octanediol, pentylene glycol, glycerin laurate, glycerin caprylate, glyceryl caprate, benzoyl peroxide, chlorhexidine gluconate, triclosan and derivatives thereof, phenoxyethanol, terpinen-4-ol, α-terpineol, resorcinol, stiemycin, erythromycin, neomycin, clindamycin and its esters, tetracyclines, metronidazole, azelaic acid, tolnaftate, nystatin, clotrimazole, ketoconazole, derivatives of zinc such as zinc pyrithionate or trithionate, zinc oxide and zinc undecylenate, piroctone olamine, isothiazolinones, selenium sulfur, benzyl hemiformal, boric acid, sodium borate, 6,6-dibromo-4,4-dichloro-2,2'-methylenediphenol [INCI: bromochlorophene], 5bromo-5-nitro-1,3-dioxane, tosylchloramide sodium [INCI: chloramine T], chloroacetamide, pchloromcresol, 2benzyl-4-chlorophenol [INCI: chlorophene], dimethyl oxazolidine, dodecyl dimethyl-2-phenoxyethyl ammonium bromide [INCI: domiphen bromide], 7ethyl bicyclooxazolidine, hexetidine, glutaraldehyde, N-(4-chlorophenyl)-N[4chloro-3(trifluoromethyl)phenyl]urea [INCI: cloflucarban], 2-hydroxy-4isopropyl-2,4,6cycloheptatriene-1one [INCI: Hinokitiol], isopropylmethylphenol, mercury salts, aluminum salts, nisin, phenoxyisopropanol, o phenylphenol, 3-heptyl-2-[(3-heptyl-4-methyl-3H-thiazole-2-ylidene) methyl]-4-methylthiazole iodide [INCI: Quaternium-73], silver chloride, sodium iodide, thymol, undecylenic acid, diethylenetriaminepentaacetic acid, ethylenediaminetetraacetic acid and ethylenediaminetetraacetates, lactoperoxidase, glucose oxidase, lactoferrin, alkylaryl sulfonates, halogenated phenols, phenol mercury acetate and/or mixtures thereof, benzamidines, isothiazolines, derivatives of phthalimide, derivatives of pyridine, guanidines, quinolines, 1,2dibromo-2,4dicyanobutane, iodine-2-propylbutyl carbamate, iodine, tamed iodines, peroxo compounds, 4chloro-3,5-dimethylphenol, 2,2'-methylene-bis(6-bromo-4-chlorophenol), 3methyl-4(1-methylethyl)phenol, 3-(4-chlorophenoxy)-1,2-propanediol, 3,4,4'-trichlorocarbanilide (TTC), betalactams, thiamine essence, eugenol, farnesol, glycerol monolaurate, diglycerin monocaprinate, N-alkyl salicylic acid amides such as n-octyl salicylic acid amide or n-decyl salicylic acid amide, derivatives of halogenated xylene and cresol, such as p-chloro-meta-cresol or p-chloro-meta-xylene, extracts of *Allium sativum, Calendula officinalis, Chamomilla recutita, Echinacea purpurea, Hyssopus officinalis, Melaleuca alternifolia* or tea tree oil, carnation essence, menthol and mint essence, light sensitive dye No. 101, light sensitive dye No. 201 and light sensitive dye No. 401, and mixtures thereof.

NO-Synthase-Inhibiting Agents

Exemplary NO-synthase-inhibiting agents include extracts of the plants *Vitis vinifera, Olea europaea, Gingko biloba*, and mixtures thereof.

Desquamating Agents and Keratolytic Agents

Exemplary desquamating agents and/or keratolytic agents and/or exfoliating agents include hydroxy acids and derivatives thereof, β-hydroxyacids, in particular salicylic acid and derivatives thereof, and gentisic acid; α-hydroxyacids and its salts, such as glycolic acid, ammonium glycolate, lactic acid, 2-hydroxyoctanoic acid, α-hydroxycaprylic acid, mandelic acid, citric acid, malic acid and tartaric acid; α- and β-hydroxybutyric acids; polyhydroxy acids such as gluconic acid, glucuronic acid and saccharic acid; keto acids such as pyruvic acid, and glyoxylic acid; pyrrolidinecarboxylic acid; cysteic acid and derivatives thereof; aldobionic acids; azelaic acid and derivatives thereof such as azeloyl diglycinate; ascorbic acid and derivatives thereof such as 6-0palmitoylascorbic acid, ascorbyl glucoside, dipalmitoyl ascorbic acid, magnesium salt of ascorbic acid-2phosphate (MAP), sodium salt of ascorbic acid-2phosphate (NAP), ascorbyl tetraisopalmitate (VCIP); nicotinic acid, its esters and nicotinamide (also called vitamin B3 or vitamin PP); nordihydroguaiaretic acid; urea; oligofucoses; cinnamic acid; derivatives of jasmonic acid; hydroxy stilbenes such as resveratrol; *Saccharum officinarum* extract; enzymes involved in desquamation or degradation of the corneodesmosomes, such as glycosidases, stratum corneum chymotryptic enzyme (SCCE) and other proteases such as trypsin, chymotrypsin, sutilain, papain and bromelain; chelating agents such as ethylenediaminetetraacetic acid (EDTA) and salts thereof, aminosulfonic compounds such as 4-(2-hydroxyethyl)piperazine-1-ethanesulfonic acid (HEPES) and sodium methyiglycine diacetate (TRILON® M marketed by BASF); derivatives of 2-oxothiazolidine-4carboxylic acid (procysteine); derivatives of sugars such as O-octanoyl-6-D-maltose and N-acetylglucosamine; chestnut extract (*Castanea sativa*) such as that marketed by SILAB under the name Recoverine® [INCI: water, *Castanea sativa* seed extract]; opuntia extract (*Opuntia ficus*-indica) such as that marketed by SILAB as Exfolactive® [INCI: hydrolyzed *Opuntia ficus Indica* flower extract]; Phytosphingosine SLC® [INCI: salicyloyl phytosphingosine] marketed by Degussa/Evonik, Peel-Moist™ [INCI: glycerin, papain, calcium pantothenate, xanthan gum, caprylyl glycol, urea, magnesium lactate, ethylhexylglycerin, potassium lactate, serine, alanine, proline, magnesium chloride, sodium citrate]; extract or combination of extracts of *Sophora japonica*, papaya, pineapple, pumpkin or sweet potato, and mixtures thereof.

Melanin Stimulating, Propigmenting, Self-Tanning and/or Melanocyte Proliferation Stimulating Agents Example agents which stimulate the synthesis of melanin, the propigmenting agent, the self-tanning agent and/or the melanocyte proliferation stimulating agent include extracts of *Citrus Aurantium Dulcis Fruit, Coleus forskohlii, Coleus esquirolii, Coleus scutellarioides, Coleus xanthanthus, Ballota nigra, Ballota lanata, Ballota suaveolens, Marrubium cylleneum, Cistus creticus, Amphiachyris amoena, Aster oharai, Otostegia fruticosa, Plectranthus barbatus, Halimium viscosum* and *Larix laricina*, dihydroxyacetone and derivatives thereof, sugars, for example erythrulose, melanin and derivatives thereof including melanin polymers and derivatives of melanin with a low molecular weight which are soluble in water, forskolin and derivatives thereof including deacetylforskolin and isoforskolin, tyrosine and derivatives thereof including acetyl tyrosine, oleoyl tyrosine, 3-amino tyrosine and 3-nitrotyrosine, copper salts such as $CuCl_2$, carotenoids, canthaxanthins, polymers of dihydroxyindole carboxylic acid, 3,4-dihydroxybenzoic acid, 3-amino-4-hydroxybenzoic acid, aloin, emodin, alizarin, dihydroxyphenylalanine, 4,5-dihydroxynaphthalene-2-sulfonic acid, 3-dimethylaminophenol and p-aminobenzoic acid, Melatime™ [INCI: acetyl tripeptide-40] marketed by Lipotec, Heliostatine ISR™ [INCI: water, glycerin, *Pisum sativum* extract] marketed by Vincience/ISP, Vegetan® [INCI: dihydroxyacetone] or Vegetan® Premium [INCI: dihydroxyacetone, melanin] marketed by Soliance, Melano-Bronze™ [INCI: *Vitex agnus-castus* extract, acetyl tyrosine] marketed by Mibelle Biochemistry, Melitane® [INCI: acetyl hexapeptide-1] marketed by Institut Européen de Biologie Cellulaire/Unipex Innovations, Actibronze® [INCI: hydrolyzed wheat protein, acetyl tyrosine, copper gluconate] and Instabronze® [INCI: dihydroxyacetone, tyrosine] marketed by Alban Muller, Thalitan™ [INCI: hydrolyzed algin, magnesium sulfate, manganese sulfate] marketed by CODIF, Tyrosilane® [INCI: methylsilanol acetyl tyrosine] marketed by Exsymol, TyrExcel™ [INCI: oleoyl tyrosine, *Luffa Cylindrica* seed oil, oleic acid] or Tyr-Ol™ [INCI: oleoyl tyrosine, butylene glycol, oleic acid] marketed by Sederma/Croda, Bronzing S. F. [proposed INCI: butyryl pentapeptide] marketed by Infinitec Activos or Biotanning® [INCI: hydrolyzed *Citrus aurantium dulcis* fruit extract] marketed by Silab, and mixtures thereof.

Lipolytic Agents, Agents Stimulating Lipolysis, Venotonic Agents and Anti-Cellulite Agents Exemplary lipolytic agents, agents stimulating lipolysis, venotonic agents and/or anticellulite agents include extracts of *Bupleurum chinensis, Cecropia obtusifolia, Celosia cristata, Centella asiatica, Chenopodium quinoa, Chrysanthellum indicum, Citrus aurantium amara, Coffea arabica, Coleus forskohlii, Commiphora myrrha, Crithmum maritimum, Eugenia caryophyllus, Ginkgo biloba, Hedera helix* (ivy extract), *Hibiscus sabdariffa, Ilex paraguariensis, Laminaria digitata, Nelumbium speciosum, Pauffinia cupana, Peumus boldus, Phyllacantha fibrosa, Prunella vulgaris, Prunus amygdalus dulcis, Ruscus aculeatus* (Butcher's broom extract), *Sambucus nigra, Spirulina platensis* algae, *Uncaria tomentosa* and *Verbena officinalis*, dihydromyricetin, coenzyme A, lipase, glaucine, visnadine, Regu®Shape [INCI: isomerized linoleic acid, lecithin, glycerin, polysorbate 80] marketed by Pentapharm/DSM, UCPeptide™ V [INCI: pentapeptide] and AT Peptide™ IS [INCI: tripeptide-3] marketed by Vincience/ISP, Liporeductyl® [INCI: caffeine, Butcher's broom (Ruscus aculeatus) root extract, TEA-hydroiodide, carnitine, ivy (*Hedera helix*) extract, escin, tripeptide-1] marketed by Lipotec, Adiposlim™ [INCI: sorbitan laurate, lauroyl praline] marketed by SEPPIC, caffeine, carnitine, escin, triethanolamine iodide, and mixtures thereof.

Heat Shock Protein Synthesis Stimulating Agents

Exemplary heat shock protein synthesis stimulating agents include extracts of *Opuntia ficus indica, Salix alba, Lupinus* spp., *Secale cereale*, extracts of red algae from the genus *Porphyra*, extracts of crustaceans from the genus *Artemia*, jojoba seed oil, grape seed extracts, green tea extracts, geranylgeranylacetone, celastrol, zinc and its salts, 2-cyclopenten-1-one, proteasome inhibitors, for example bortezomib; prostaglandins and derivatives thereof, hydroxylamine and derivatives thereof, for example bimoclomol; chalcone and derivatives thereof, hyperosmotic agents, for example sorbitol and derivatives thereof, mannitol and derivatives thereof or glycerol and derivatives thereof, isosorbide (dianhydro-D-glucitol) urea or salicylic acid and derivatives thereof among others, Thermostressine™ [INCI: acetyl tetrapeptide-22], and mixtures thereof.

Agents Inhibiting Sweat-Degrading Enzymes

Exemplary agents for inhibiting sweat-degrading enzymes include trialkyl citrates such as trimethyl citrate, tripropyl citrate, triisopropyl citrate, tributyl citrate or triethyl citrate; lanosterine sulfate and lanosterine phosphate, cholesterol, campesterol, stigmasterol and sitosterol; dicarboxylic acids and their esters, such as glutaric acid, monoethyl glutarate, diethyl glutarate, adipic acid, monoethyl adipate, diethyl adipate; malonic acid and diethyl malonate, hydroxycarboxylic acids and their esters such as malic acid, tartaric acid and diethyl tartrate, zinc glycinate, and mixtures thereof.

Agents Stimulating or Regulating Keratinocyte Differentiation

Exemplary agents for stimulating or regulating keratinocyte differentiation include minerals such as calcium, retinoids such as retinol and tretinoin, analogues of vitamin D3 such as calcitriol, calcipotriol and tacalcitol, lupine (Lupinus albus) extract such as that marketed by SILAB under the name Structurin® [INCI: hydrolyzed lupine protein], β-sitosterol sulfate, such as that marketed by Vincience/ISP under the name Phytocohesine PSP® [INCI: sodium beta-sitosterol sulfate], maize (*Zea Mays*) extract such as that marketed by Solabia under the name Phytovityl C® [INCI: water, *Zea Mays* extract], *Helix aspersa Müller* glycoconjugates, and mixtures thereof.

Exopolysaccharides

Exemplary exopolysaccharides, such as those of bacterial origin, include those secreted by a strain of the *Halomonas anticariensis* species, which reduce lipid accumulation, as described in WO 2015/063240, and an exopolysaccharide which inhibits neuronal exocytosis and stimulates the fibroblast proliferation which is excreted by the strain of the *Vibrio* sp. species with deposit number CNCM 1-4239 according to the Budapest Treaty on Sep. 4, 2009, in the "Collection Nationale de Culture de Microorganismes" [National Microorganism Culture Collection] (CNCM), Pasteur Institute, 28 rue du Docteur Roux, 75724 Paris, France, as described in WO 2014147255 and U.S. Ser. No. 14/778,874, filed Sep. 21, 2015.

Exemplary cell extracts and extracts produced by microorganisms, or commercial mixtures which contain them include hydrosoluble cell extracts and hydrosoluble extracts produced by microorganisms, for example Antarcticine® [INCI: Pseudoalteromonas ferment extract] and Trylagen® [INCI: Pseudoalteromonas ferment extract, hydrolyzed wheat protein, hydrolyzed soy protein, Tripeptide-10 citrulline, Tripeptide-1] marketed by Lipotec, yeast extract, extract of *Saccharomyces cerevisiae* and the product of milk fermentation with *Lactobacillus Bulgaricus*, among others.

Excipients

Excipients which may be present include emulsifiers, organic solvents, surfactants, liquid propellants, binders and thickeners, fillers, lubricants, glidants, pigments, dyes, perfumes, flavoring agents, preservatives, and combinations thereof.

Components serving as lubricants, solvents, propellants, binders and thickeners and emulsifiers may include one or more of liquid hydrocarbons, waxes, natural fats and fatty oils, alcohols, ethers, esters, silicone oils, monosaccharides, polymers, and the like.

Exemplary liquid hydrocarbons include α-olefins, $C_{10}$—$C_{40}$ alkanes, $C_{10}$—$C_{40}$ alkenes, and mixtures thereof, such as squalene, ceresin, mineral oils, and petroleum jelly.

Exemplary waxes include microcrystalline wax, natural waxes such as jojoba oil, carnauba wax, candelilla wax, rice bran wax, shellac, lanolin, mink sebaceous wax, spermaceti wax, sugarcane wax, sperm whale oil, beeswax and montan wax.

Exemplary natural fats and fatty oils include avocado oil, almond oil, olive oil, extra virgin olive oil, sesame seed oil, rice bran oil, rice oil, rice germ oil, corn oil, safflower oil, soybean oil, maize oil, rape seed oil, persic oil, palm kernel oil, palm oil, castor oil, sunflower oil, high oleic sunflower oil, grape seed oil, cottonseed oil, coconut oil, hydrogenated coconut oil, beef tallow, hydrogenated oil, horse oil, mink oil, yolk oil, yolk fat oil, rose hip oil, kukui nut oil, evening primrose oil, wheat germ oil, peanut oil, *Camellia japonica* oil, *Camellia kissi* oil, cacao butter, Japan wax, beef bone tallow, nest's-foot oil, swine tallow, equine tallow, ovine tallow, shea butter, macadamia nut oil and meadow foam seed oil.

Exemplary fatty acids include lauric acid, myristic acid, palmitic acid, stearic acid, behenic acid, oleic acid, linoleic acid, linolenic acid, γ-linolenic acid, isostearic acid, 12-hydroxystearic acid, undecenoic acid and coconut oil fatty acid.

Exemplary lower alcohols include ethanol, 1-propanol, 2-propanol, 1-butanol, 2-butanol and benzyl alcohol. Exemplary higher alcohols include isostearyl alcohol, 2-octyldodecan-1-ol, 2-hexyldecan-1-ol, cholesterol, phytosterols, lauryl alcohol, myristyl alcohol, cetyl alcohol, stearyl alcohol, oleyl alcohol, behenyl alcohol and cetostearyl alcohol. Exemplary polyhydric alcohols include ethylene glycol, diethylene glycol, triethylene glycol, polyethylene glycol, propylene glycol, dipropylene glycol, polypropylene glycol, pentanediol, glycerin, diglycerin, polyglycerin, isoprene glycol, 1,3-butylene glycol, 3-methyl-1,3-butanediol, 1,3-butanediol, 1,2-pentanediol and 1,2-hexanediol.

Exemplary alkyl glyceryl ethers include stearyl monoglyceride, 3-hexadecoxypropane-1,2-diol, 3-[(Z)-octadec-9-enoxy]propane-1,2-diol and isostearyl glyceryl ether.

Exemplary esters include isopropyl myristate, butyl myristate, isopropyl palmitate, ethyl stearate, butyl stearate, ethyl oleate, ethyl linoleate, isopropyl linoleate, cetyl caprylate, hexyl laurate, isooctyl myristate, decyl myristate, myristyl myristate, cetyl myristate, octadecyl myristate, cetyl palmitate, stearyl stearate, decyl oleate, oleyl oleate, cetyl ricinoleate, isostearyl laurate, isotridecyl myristate, isocetyl myristate, isostearyl myristate, 2-octyldodecyl myristate, 2-ethylhexyl palmitate, isocetyl palmitate, isostearyl palmitate, 2-ethylhexyl stearate, isocetyl stearate, isodecyl oleate, octyldodecyl oleate, octyldodecyl ricinoleate, ethyl isostearate, isopropyl isostearate, cetyl 2-ethylhexanoate, cetostearyl 2-ethylhexanoate, stearyl 2-ethylhexanoate, hexyl isostearate, ethylene glycol dioctanoate, ethylene glycol dioleate, propylene glycol dicaprylate, propylene glycol dicaprylate/dicaprate, lauryl lactate, myristyl lactate, cetyl lactate, trioctyl citrate, diisostearyl malate, 2-ethylhexyl hydroxystearate, diisopropyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12stearoyl hydroxystearate, stearyl 12stearoyl hydroxystearate, isostearyl 12-stearoyl hydroxystearate, octyl isononanoate.

Exemplary silicone oils include polysiloxanes, polyether modified silicones, alcohol modified silicones, alkyl modified silicones, and amino modified silicones.

Exemplary saccharides include mannitol, sorbitol, xylitol, maltitol, erythritol, pentaerythritol, glucose, sucrose, fructose, lactose, maltose, xylose and trehalose.

Exemplary polymers include sodium alginate, carrageenan, agar, guar gums, tamarind gum, dextrin, starch, locust bean gum, gum arabic, pectin, quince, chitosan, starch, curdlan, xanthan gum, dextran, pullulan, microcrystalline cellulose, methyl cellulose, ethyl cellulose, hydroxyethyl cellulose, hydroxypropyl cellulose, hydroxypropyl methylcellulose, carboxymethyl cellulose, carboxy starch, cationized cellulose, starch phosphate ester, albumin, casein, gelatin, sodium polyacrylate, polyacrylamides, carboxyvinyl polymers, polyethylene imines, polyethylene glycol, polyvinyl alcohol, polyvinyl pyrrolidone, polyvinyl ether, polyacrylamides, acrylic acid copolymers, methacrylic acid copolymers, maleic acid copolymers, vinylpyridine copolymers, ethylene/acrylic acid copolymers, vinyl pyrrolidone based polymers, vinyl alcohol/vinyl pyrrolidone copolymers, N-substituted acrylamide based polymers, amino-modified silicones, dimethylacrylic acid based polymers, acrylic acid based anionic polymers, methacrylic acid based anionic polymers, modified silicone, acrylate/methacrylate $C_{10}$—$C_{30}$ alkyl copolymers, and polyoxyethylene/polyoxypropylene copolymers.

Exemplary anionic surfactants include potassium coconut oil fatty acid, sodium coconut oil fatty acid, triethanolamine coconut oil fatty acid, potassium laurate, sodium laurate, triethanolamine laurate, potassium myristate, sodium myristate, isopropanolamine myristate, potassium palmitate, sodium palmitate, isopropanolamine palmitate, potassium stearate, sodium stearate, triethanolamine stearate, potassium oleate, sodium oleate, castor oil fatty acid sodium, zinc undecylate, zinc laurate, zinc myristate, magnesium myristate, zinc palmitate, zinc stearate, calcium stearate, magnesium stearate, aluminum stearate, calcium myristate, magnesium myristate, aluminum dimyristate, aluminum isostearate, polyoxyethylene lauryl ether acetate, sodium polyoxyethylene lauryl ether acetate, polyoxyethylene tridecyl ether acetate, sodium polyoxyethylene tridecyl ether acetate, sodium stearoyl lactate, sodium isostearoyl lactate, sodium lauroyl sarcosinate, coconut oil fatty acid sarcosinate, sodium coconut oil fatty acid sarcosinate, coconut oil fatty acid sarcosine triethanolamine, lauroyl sarcosine, potassium lauroyl sarcosinate, lauroyl sarcosine triethanolamine, oleoyl sarcosine, sodium myristoyl sarcosinate, sodium stearoyl glutamate, coconut oil fatty acid acyl glutamic acid, potassium coconut oil fatty acid acyl glutamate, sodium coconut oil fatty acid acyl glutamate, lauroyl glutamic acid, potassium lauroyl glutamate, sodium lauroyl glutamate, myristoyl glutamic acid, potassium myristoyl glutamate, sodium myristoyl glutamate, stearoyl glutamic acid, potassium stearoyl glutamate, disodium stearoyl glutamate, sodium hydrogenated beef tallow fatty acid acyl glutamate, sodium coconut oil fatty acid/hydrogenated beef tallow fatty acid acyl glutamate, lauroyl methyl alanine, sodium lauroyl methyl alanine, sodium myristoyl methyl alanine, sodium lauroyl methyl taurate, sodium oleoyl methyl taurate, sodium alkane sulfonate, sodium tetradecene sulfonate, sodium dioctyl sulfosuccinate, disodium lauryl sulfosuccinate, sodium coconut oil fatty acid ethyl ester sulfonate, sodium lauryl sulfate, triethanolamine lauryl sulfate, sodium cetyl sulfate, triethanolamine alkyl sulfates, sodium alkyl sulfates, triethanolamine alkyl sulfates, alkyl ammonium sulfates, diethanolamine alkyl sulfates, triethanolamine alkyl sulfates, triethanolamine alkyl sulfates, lauryl ammonium sulfate, potassium lauryl sulfate, magnesium lauryl sulfate, monoethanolamine lauryl sulfate, diethanolamine lauryl sulfate, sodium myristyl sulfate, sodium stearyl sulfate, sodium oleyl sulfate, triethanolamine oleyl sulfate, sodium polyoxyethylenes lauryl ether sulfates, triethanolamine polyoxyethylene lauryl ether sulfate, sodium polyoxyethylene alkyl ether sulfates, triethanolamine polyoxyethylene alkyl ether sulfates, sodium polyoxyethylene myristyl ether sulfates, sodium higher fatty acid alkanolamide sulfate esters, lauryl phosphate, sodium lauryl phosphate, potassium cetyl phosphate, diethanolamine cetyl phosphate, polyoxyethylene oleyl ether phosphate, polyoxyethylene lauryl ether phosphate, sodium polyoxyethylene lauryl ether phosphate, polyoxyethylene cetyl ether phosphate, sodium polyoxyethylene cetyl ether phosphate, polyoxyethylene stearyl ether phosphate, polyoxyethylene oleyl ether phosphate, sodium polyoxyethylene oleyl ether phosphate, polyoxyethylene alkylphenyl ether phosphates, sodium polyoxyethylene alkylphenyl ether phosphates, triethanolamine polyoxyethylene alkylphenyl ether phosphates, polyoxyethylene octyl ether phosphate, polyoxyethylene alkyl ether phosphate, triethanolamine polyoxyethylene lauryl ether phosphate, and diethanolamine polyoxyethylene oleyl ether phosphate.

Exemplary cationic surfactants include alkyl amines, alkyl imidazolines, ethoxylated amides, quaternary compounds, quaternized esters, and alkyl amine oxides. Examples include lauramine oxide, dicetyldimonium chloride, and cetrimonium chloride.

Exemplary amphoteric and zwitterionic surfactants include betaines, alkyl amidopropyl betaines, alkyl sulfobetaines, alkyl glycinates, alkyl carboxyglycinates, alkyl amphopropionates, alkyl amidopropyl hydroxysultaines, acyl taurates and acyl glutamates wherein the alkyl and acyl groups have from 8 to 18 carbon atoms. Examples include cocoamidopropyl betaine, sodium cocoamphoacetate, cocoamidopropyl hydroxysultaine, and sodium cocoamphopropionate.

Exemplary nonionic surfactants include aliphatic ($C_6$—$C_{18}$) primary or secondary linear or branched chain acids, alcohols or phenols, alkyl ethoxylates, alkyl phenol alkoxylates (especially ethoxylates and mixed ethoxy/propoxy), block alkylene oxide condensate of alkyl phenols, alkylene oxide condensates of alkanols, ethylene oxide/propylene oxide block copolymers, semipolar nonionics (e.g., amine oxides), as well as alkyl amine oxides. Other suitable nonionics include mono- or di-alkyl alkanolamides and alkyl polysaccharides, sorbitan fatty acid esters, polyoxyethylene sorbitan fatty acid esters, polyoxyethylene sorbitol esters, polyoxyethylene acids, and polyoxyethylene alcohols. Examples of nonionic surfactants include alkyl polyglucoside, cocamidopropyl and lauramine oxide, polysorbate 20, ethoxylated linear alcohols, cetearyl alcohol, lanolin alcohol, stearic acid, glyceryl stearate, polyoxyethylene lauryl ether, polyoxyethylene oleyl ether, PEG-100 stearate, sorbitan monooleate, sorbitan isostearate, and oleth-20, and mixtures thereof.

Exemplary powdered fillers include kaolin, silicic anhydride, magnesium aluminum silicate, sericite, talc, boron nitride, mica, montmorillonite, cellulose powder, wheat starch, silk powder, maize starch, and mixtures thereof.

Exemplary dyes and pigments include nitro dyes, azo dyes, nitroso dyes, xanthene dyes, quinoline dyes, anthraquinone dyes, indigo dyes, sepia powder, caramel, cochineal, carbon black, yellow iron oxide, black iron oxide, red iron oxide, titanium oxide, titanium dioxide, and mixtures thereof.

Exemplary pH adjusting agents include sodium hydroxide, potassium hydroxide, triethanolamine, and mixtures thereof.

Exemplary salts include sodium chloride, potassium chloride, magnesium chloride, sodium sulfate, and mixtures thereof.

Exemplary ahydroxy acids include citric acid, glycolic acid, tartaric acid and lactic acid, and mixtures thereof.

Exemplary cosmetic and/or absorbent and/or body odor masking deodorant and/or antiperspirant agent, perfuming substance and/or perfumed oils include the complex zinc salt of ricinoleic acid, Styrax, derivatives of abiotic acid, sage essence, chamomile essence, carnation essence, lemon balm essence, mint essence, cinnamon leaf essence, lime flower essence, juniper berry essence, vetiver essence, olibanum essence, galbanum essence, labdanum essence, lavender essence, peppermint essence, bergamot orange, dihydromyrcenol, lilial, lyral, citronellol, lemon essence, mandarin essence, orange essence, lavender essence, muscat, geranium bourbon essence, aniseed, cilantro, cumin, juniper, extracts of fleur-de-lis, lilac, roses, jasmine, bitter orange blossom; benzyl acetate, p-tert-butylcyclohexyl acetate, linalyl acetate, phenylethyl acetate, ethylmethylphenyl glycinate, linalyl benzoate, benzyl formate, allyl cyclohexyl propionate, styrallyl propionate, benzyl salicylate, benzyl ethyl ether, linear alkanes with from 8 to 18 carbon atoms, citral, ricinoleic acid, citronellal, citronellyl oxyacetaldehyde, cyclamen aldehyde, hydroxycitronellal, bourgeonal, ionones, methyl cedryl ketone, anethole, eugenol, isoeugenol, geraniol, linalool, terpineol, phenylethyl alcohol, α-hexylcinnamaldehyde, geraniol, benzylacetone, cyclamen aldehyde, hydroxycitronellal, ambroxan, indole, hedione, sandelice, cyclovertal, β-damascone, allyl amyl glycolate, dihydromyrcenol, phenoxyethyl isobutyrate, cyclohexyl salicylate, phenylacetic acid, geranyl acetate, irotyl, floramate, active astringent products such as aluminum chloride, aluminum chlorohydrate, aluminum dichlorohydrate, aluminum sesquichlorohydrate, aluminum dihydroxyallantoinate, aluminum chlorotartrate, aluminum and zirconium trichlorohydrate, aluminum and zirconium tetrachlorohydrate, aluminum and zirconium pentachlorohydrate and/or mixtures thereof.

Exemplary essential oils include *Archangelica officinalis* (angelica) oil, *Canangium odoratum* (ylang ylang) oil, *Canarium luzonicum* (elemi) oil, orange oil, *Chamomilla recutita* (matricaria) oil, *Anthemis nobilis* oil, *Elettaria cardamomum* (cardamom) oil, *Acorus calamus* (calamus) oil, *Ferula galbaniflua* (galbanum) oil, *Cinnamomum camphora* (camphor) oil, *Daucus carota* (carrot) seed oil, *Salvia sclarea* (clary sage) oil, *Citrus paradisi* (grapefruit) oil, *Eugenia caryophyllus* (clove) oil, Cinnamon bark oil, *Coriandrum sativum* (coriander) oil, *Cupressus sempervirens* (cypress) oil, *Santalum album* (sandalwood) oil, *Juniperus virginiana* (cedar wood) oil, *Cymbopogon nardus* (citronella) oil, *Cinnamomum verum* (Cinnamon) leaf oil, *Jasmine officinale* (jasmine) absolute oil, *Juniperus communis* (juniper Berry) oil, *Zingiber officinale* (ginger) extract, *Mentha*

*spicata* (spearmint) oil, *Salvia officinalis* (sage) oil, cedar oil, *Pelargonium graveolens* (geranium) oil, *Thymus vulgaris* (thyme) oil, *Melaleuca altemifolia* (tea tree) oil, *Myristica fragrans* (nutmeg) oil, *Melaleuca viridiflora* (niaouli) oil, *Citrus aurantium* (neroli) oil, pine oil, *Ocimum basilicum* (basil) oil, *Mentha arvensis* oil, *Pogostemon cablin* (patchouli) oil, *Cymbopogon martinii* (palmarosa) oil, *Foeniculum vulgare* (fennel) oil, *Citrus bigaradia* (petitgrain) oil, *Piper nigrum* (black pepper) oil, *Boswellia carteri* (frankincense) oil, *Chrysopogon zizanioides* (vetiver) oil, *Mentha piperita* (peppermint) oil, *Citrus bergamia* (bergamot) oil, benzoin oil, *Aniba rosaeodora* (rosewood) oil, *Origanum majorana* (marjoram) oil, mandarin oil, *Commiphora myrrha* (myrrh) oil, *Melissa officinalis* (balm mint) oil, *Eucalyptus globulus* oil, *Citrus junos* oil, *Citrus aurantiifolia* (lime) oil, *Ravensara aromatica* (clove) oil, *Lavandula latifolia* (lavandin) oil, *Lavandula angustifolia* (lavender) oil, *Tilia vulgaris* (linden) oil, lemon oil, lemon grass oil, rose oil, *Aniba rosaeodora* (rosewood) oil, *Rosmarinus officinalis* (rosemary) oil and *Levisticum officinale* (lovage) oil, and mixtures thereof.

In one embodiment, the active agent includes at least one active agent which is selected from skin whitening or depigmentation agents, anti-acne agents, and mixtures thereof.

Other pharmaceutical active ingredients and/or adjuvants useful herein include antacids; agents against peptic ulcers (e.g., butylscopolamine bromide, pirenzepine hydrochloride, timepidium bromide) and gastroesophageal reflux disease; antispasmodics; analgesics; anticholinergic drugs; propulsive drugs; antiemetics; anti-nausea drugs; agents for biliary therapy; agents for hepatic therapy; lipotropics; laxatives; antidiarrhetics; intestinal adsorbents; antipropulsives; anti-inflammatory drugs; active ingredients against obesity; enzymes; hypoglycemic drugs; insulin and analogues; vitamins; proteins; minerals; anabolic steroids; antithrombotic agents; antifibrinolytics; hemostatic agents; antiarrhythmic agents; cardiac stimulants; cardiac glycosides; vasodilators; antiadrenergic agents; antihypertensive drugs; diuretics; potassium-saving agents; antihemorrhoidals; antivaricose therapy agents; capillary stabilizing agents; agents which act on the reninangiotensin system; beta-blockers; selective calcium-channel blockers; non-selective calcium-channel blockers; ACE inhibitors; angiotensin II inhibitors; agents modifying lipids; antifungals; antipruritics; anesthetics; antipsoriatics; chemotherapy drugs; corticosteroids; products for gynecological use (e.g., oxytocics, contraceptives, androgen, estrogen, progestogen, ovulation stimulants, gonadotropins, antiandrogens); products for urological use; antispasmodics; drugs used in benign prostatic hypertrophy; hormones; hormone antagonists; antibiotics; tetracyclines; amphenicols; penicillin; sulfonamides; trimethoprim; macrolides; lincosamides; streptogramins; antibacterial aminoglycosides; antibacterial quinolones; antivirals; immune serum; immunoglobulins; antineoplastic agents; immunomodulatory agents; alkylation agents; antimetabolites; plant alkaloids and other natural products; cytotoxic antibiotics; immunosuppressive agents; drugs for disorders of the musculoskeletal system; antirheumatics; agents which affect bone structure and mineralization; drugs which act on the nervous system; general anesthetics; local anesthetics; opioids; antimigraine agents; anticonvulsants; dopaminergic agents; antipsychotics (e.g., chlorpromazine hydrochloride, levomepromazine hydrochloride, clocapramine hydrochloride); anxiolytics; hypnotics; sedatives; antidepressants (e.g., imipramine hydrochloride, trazodone hydrochloride, fluvoxamine maleate); psychostimulants; anti-dementia drugs (e.g., donepezil, rivastigmine, galanthamide hydrobromide, memantine hydrochloride); antianxiety drugs (e.g., diazepam, alprazolam, tandospirone citrate); tranquilizers (hydroxyzine hydrochloride); brain function stimulant/activators (e.g., tiapride hydrochloride, protirelin tartrate); cerebral circulation improving drugs (isosorbide mononitrate or dinitrate, pentoxifylline, fasudil hydrochloride); Parkinson's disease therapeutic agents (hydrochloric acid benserazide, amantadine hydrochloride, talipexole hydrochloride); chemical-transmitter release-inhibition drugs (emedastine fumarate, suplatast tosilate, epinastine hydrochloride); cardiac disease therapeutic-agents (e.g., aminophylline, diltiazem hydrochloride, nicorandil, propranolol hydrochloride, isoprenaline hydrochloride, disopyramide phosphate, procainamide hydrochloride); antihypertensive drugs (e.g., captopril, enalapril maleate, amosulalol hydrochloride, prazosin hydrochloride, urapidil, clonidine hydrochloride); vasodilators (e.g., tolazoline hydrochloride); vasoconstrictors (e.g., amezinium metilsulfate, etilefrine hydrochloride, phenylephrine hydrochloride, midodrine hydrochloride); antihyperlipidemic drugs (pravastatin sodium, fluvastatin sodium, cerivastatin sodium); parasympathomimetics; drugs used in addictive disorders; anti-vertigo agents; antiparasitic agents; insecticides; insect repellants; nasal decongestants; antitussives and expectorants (dextromethorphan hydrobromide, fominoben hydrochloride, acetylcysteine); asthma preparations (clenbuterol hydrochloride, fenoterol hydrobromide, procaterol hydrochloride); mucolytic agents; cough suppressants; ophthalmic active ingredients; otological active ingredients; antiglaucoma drugs; miotics; mydriatics; cycloplegics; anti-dandruff agents; muscle contraction inhibitory agents; H2 blockers (e.g., ranitidine hydrochloride, roxatidine-hydrochloride acetate); proton pump inhibitors (e.g., omeprazole, lansoprazole, rabeprazole), antiemetic (e.g., granisetron hydrochloride, azasetron hydrochloride, ondansetron hydrochloride, ramosetron hydrochloride), anti-rheumatism agents (e.g., bucillamine, penicillamine); urological-diseases drugs (e.g., oxybutynin hydrochloride, tamsulosin hydrochloride, propiverine hydrochloride); (beta)-blockers (e.g., bisoprolol fumarate, betaxolol hydrochloride); and mixtures thereof.

The nature of these active ingredients excipients can be synthetic or natural, such as vegetable extracts, or come from a biotechnological process or from a combination of a synthetic process and a biotechnological process. Additional examples can be found in the Personal Care Product Council (PCPC) International Cosmetic Ingredient Dictionary & Handbook, 15th Edition (2014). A biotechnological process is understood to be any process which produces the active ingredient, or part of it, in an organism, or in a part of it.

In some embodiments, one or more of the active agents and/or excipients may be present in the exemplary film or on a surface thereof in the form of liposomes, mixed liposomes, oleosomes, niosomes, millicapsules, microcapsules, nanocapsules, nanostructured lipid carriers, cyclodextrins, vesicles, micelles, mixed micelles of surfactants, surfactant-phospholipid mixed micelles, millispheres, microspheres, nanospheres, lipospheres, microemulsions, nanoemulsions, miniparticles, milliparticles, microparticles, nanoparticles and solid lipid nanoparticles.

Processes to Make the TPU and Face Mask

1. "One-Shot" Process

The reactants (the polyols, the diisocyanate, and the chain extender), and optionally a catalyst, may be reacted together to form the TPU. Any known processes to react these reactants may be used to make the TPU. In one embodiment, the process is a so-called "one-shot" process where all the reactants are added to an extruder reactor and reacted. The equivalent weight amount of the diisocyanate to the total equivalent weight amount of the hydroxyl containing components, that is, the polyols and the chain extender, can be from 0.95 to 1.10, or from 0.96 to 1.02, and even from 0.97 to 1.005. Reaction temperatures utilizing a urethane catalyst can be from 175 to 245° C., and in another embodiment from 180 to 220° C. The resulting composition may be pelletized, granulated, or directly formed into the film.

2. Pre-Polymer Process

The TPU can also be prepared utilizing a pre-polymer process. In the pre-polymer route, the polyols are first reacted with generally an equivalent excess of one or more diisocyanates to form a pre-polymer solution having free or unreacted diisocyanate therein. The reaction is generally carried out at temperatures of from 80 to 220° C., or from 150 to 200° C. in the presence of a suitable urethane catalyst. Subsequently, a chain extender, as noted above, is added in an equivalent amount generally equal to the isocyanate end groups as well as to any free or unreacted diisocyanate compounds. The overall equivalent ratio of the total diisocyanate to the total equivalent of the polyol intermediate and the chain extender is thus from 0.95 to 1.10, or from 0.96 to 1.02 and even from 0.97 to 1.05. The chain extension reaction temperature is generally from 180 to 250° C. or from 200 to 240° C. Typically, the pre-polymer route can be carried out in any conventional device including an extruder. In such embodiments, the polyol intermediates are reacted with an equivalent excess of a diisocyanate in a first portion of the extruder to form a pre-polymer solution and subsequently the chain extender is added at a downstream portion and reacted with the pre-polymer solution. Any conventional extruder can be utilized, including extruders equipped with barrier screws having a length to diameter ratio of at least 20 and in some embodiments at least 25.

In one embodiment, the ingredients are mixed on a single or twin screw extruder with multiple heat zones and multiple feed ports between its feed end and its die end. The ingredients may be added at one or more of the feed ports and the resulting TPU composition that exits the die end of the extruder may be pelletized, granulated, or used directly for forming into the film.

3. Continuous Process

The "pre-polymer" process and the "one shot" process can be performed in either a batch or continuous manner. That is, in some embodiments the TPU may be made by reacting the components together in a "one shot" polymerization process wherein all of the components, including reactants are added together simultaneously or substantially simultaneously to a heated extruder and reacted to form the TPU. In other embodiments the TPU may be made by first reacting the polyisocyanate component with some portion of the polyols forming a pre-polymer, and then completing the reaction by reacting the pre-polymer with the remaining reactants, resulting in the TPU. After exiting the extruder, the composition may be pelletized, granulated, or directly formed into the film.

To form the film, the polyurethane polymer may be solvent cast or extruded onto a release layer.

Solvent casting may include combining the TPU with a casting liquid to form a casting solution. The casting liquid may be a mixture of water and a water-miscible organic solvent, such as one or more of a $C_2$—$C_{10}$ alcohol, tetrahydrofuran, dimethylacetamide, dimethylformamide, and the like. A ratio of solvent to water in the casting liquid/solution may be from 20:1 to 1:10. As an example, a mixture of ethanol and water is used for casting. The casting solution may optionally include one or more of the active agents and/or excipients. The casting solution may be applied to a release layer, such as a sheet of high density polyethylene (HDPE), Teflon™, or low density polyethylene (LDPE), to provide a cast film. The cast film may be dried to form the dry polymer film, e.g., in air or another atmosphere, at room temperature or slightly above.

The resulting dry film may be shaped to form the face mask, e.g., by cutting the film to the desired shape. The face mask may be hydrated, prior to use, with an aqueous solution. The aqueous hydration solution may contain one or more of the active agents and/or excipients. The hydration may be performed before or after cutting the film to the desired shape.

In one embodiment, the active agent is present in the film prior to shaping and hydration. For example, the active agent is incorporated during solvent casting of the film. The active agent-containing film may be hydrated before or after cutting the film in to the shape of the face mask.

The release layer is removed before or after applying the face mask to the skin of the user.

One advantage of the exemplary TPU film is that it can be cold processed (e.g., solvent cast, e.g., at a temperature of less than 40° C., or less than 30° C.), allowing customized formulations by salons and in office preparations by dermatologists. For conventional hydrocolloid films, cold processing is not available, which limits the active agents and the use of hydrocolloid films to larger manufacturers.

The hydrated TPU films when tested for wet burst strength may have higher absolute peak force at break and a greater % elongation than hydrocolloid films of the same thickness so that the films may be stretched around facial or other body features without ripping and handled easily.

The exemplary TPU substrate does not support bacterial growth and can be stored for extended periods without the need for preservatives. A preservative may be included in the aqueous hydration formulation.

Without intending to limit the scope of the exemplary embodiment, the following examples illustrate polyurethane films and face mask compositions.

EXAMPLES

Example 1

Preparation of Polyurethane Films

Polyurethane films are formed using the reactants shown in TABLE 1. Examples A-H are formed using a mixture of Polyols A and B while examples J and K use only one of the two polyols. In all the examples, Polyol A=PEG 8000 (a poly(ethylene glycol) with an average molecular weight of 8000 daltons) and Polyol C=PEG 300 (a poly(ethylene glycol) with an average molecular weight of 300 daltons).

As polyol B, PEG 1450, "1450" (a poly(ethylene glycol) with an average molecular weight of 1450 daltons) is employed. Alternatively, a polyether copolymer diol with polypropylene glycol and polyethylene oxide segments and an average molecular weight of 2000 daltons, available as Poly-G™ 55-56 ("PolyG") from Lonza, is used.

Different polyisocyanates are evaluated: 4,4'-diisocyanato dicyclohexylmethane (H12MDI), available from Bayer as Desmodur™ W; and hexamethylene diisocyanate (HDI).

Different chain extenders are evaluated: 1,4-butanediol (bdo) and 1,10-decanediol (ddo).

As the catalyst for Examples A-H, an organotin catalyst, Cotin® 430, is used, which is a dioctyltin carboxylate, available from Vertellus Specialties Inc.

The proportions of hard, soft and intermediate segment are calculated as described above, therefore:

Wt. % soft segment=wt. % PEG–8000+wt. % PEG-1450+wt. % PEG–300 (or PolyG™ 55-56).

Wt. % hard segment=wt. % isocyanate in hard segment+ wt. % chain extender.

Wt. isocyanate in hard segment=[moles isocyanate– moles (PEG-8000+PEG–1450+PEG-300 (or PolyG™ 55-56)]×Mw isocyanate Wt. % intermediate segment=100 wt. % soft segment wt. % hard segment.

The ratings in TABLE 1 are based on the overall performance of the compositions as a thin face mask, where 1 indicates the TPU performed poorly and 5 indicates the TPU performed exceptionally well. It is to be appreciated that the compositions may be useful in thicker face mask or for other purposes even when the rating is low.

Example 2

Solubility Study

Some of the polymers formed in Example 1, in granular form, are heated to between 40 and 60° C. in various solvents to test solubility. If the polymer remained in solution upon cooling to room temperature, it is deemed soluble. TABLE 2 below shows the 24 hour granule swell data in water. TABLE 3 shows the amount of solvent uptake if the polymer is soluble or swollen. If swollen, then TABLE 3 shows the gm solvent/gm polymer uptake. TABLES 4 and 5 show the viscosity at various concentrations in EtOH:H$_2$O mixtures, as measured by Brookfield viscosity at 20 rpm.

Viscosity

Brookfield rotating spindle method (all viscosity measurements reported herein are conducted by the Brookfield method): The viscosity measurements are calculated in centipoise (Cps), employing a Brookfield rotating spindle viscometer, Model RVT (Brookfield Engineering Laboratories, Inc.), at about 20 revolutions per minute (rpm), at ambient room temperature of about 20 to 25° C. (hereafter referred to as viscosity). Spindle sizes are selected in accordance with the standard operating recommendations from the manufacturer. Generally, spindle sizes are selected as follows:

TABLE 1

TPU Compositions

| TPU | Polyol A (PEG8000) wt. % | Polyol B wt. % | Diisocyanate wt. % | Polyol C (PEG300) wt. % | Chain extender wt. % |
|---|---|---|---|---|---|
| Ex. A | 24.7 | 57.7 (1450) | 15.0 H12MDI | 0.99 | 0.99 bdo |
| Ex. B | 24.73 | 57.82 (1450) | 15.03 H12MDI | 0.75 | 1.12 bdo |
| Ex. C | 24.73 | 57.82 (1450) | 15.11 H12MDI | 0.60 | 1.19 bdo |
| Ex. D | 26.29 | 61.25 (1450) | 10.13 HDI | 0.6 | 1.21 bdo |
| Ex. E | 26.29 | 61.25 (Poly-G) | 9.47 HDI | 0.82 | 1.64 bdo |
| Ex. F | 24.73 | 57.82 (Poly-G) | 14.39 H12MDI | 1.68 | 0.84 bdo |
| Ex. G | 24.49 | 57.07 (1450) | 14.98 H12MDI | 0.65 | 2.27 ddo |
| Ex. H | 24.49 | 57.07 (Poly-G) | 14 H12MDI | 0.87 | 3.03 ddo |
| Ex. J | 82.5 | — | 13.3 H12MDI | — | 3.6 bdo |
| Ex. K | 90.5 | — | 7.4 H12MDI | — | 1.5 bdo |
| Ex. L | 89.52 | — | 7.12 H12MDI | — | 2.83 ddo |
| Ex. M | 87.04 | — | 8.8 H12MDI | — | 3.84 ddo |
| Ex. N | 86.6 | — | 10.41 H12MDI | — | 2.52 bdo |

| TPU | Wt. % hard | Wt. % Soft | Wt. % Intermediate | Rating |
|---|---|---|---|---|
| Ex. A | 3.87 | 83.4 | 12.74 | 2 (weak) |
| Ex. B | 4.21 | 83.15 | 12.64 | 3 |
| Ex. C | 4.43 | 83 | 12.57 | 4 |
| Ex. D | 3.35 | 88.14 | 8.51 | 1 |
| Ex. E | 4.95 | 88.36 | 6.69 | 1 |
| Ex. F | 5.37 | 84.23 | 10.40 | 5 |
| Ex. G | 5.55 | 82.21 | 12.24 | 4 |
| Ex. H | 7.98 | 82.43 | 9.59 | 4 |
| Ex. J | 14.19 | 82.5 | 3.31 | 1 (hard) |
| Ex. K | 5.93 | 90.5 | 3.57 | 5 |
| Ex. L | 7.01 | 89.52 | 3.47 | 4 |
| Ex. M | 9.59 | 87.04 | 3.37 | 4 |
| Ex. N | 10.09 | 86.6 | 3.36 | 5 |

Ex A-H vary compositionally but generally exhibit similar water uptake, flexibility and other physical properties. Examples J-N include no Polyol B or C.

Formulations are also prepared which include a mixture of one of Examples A-H with one of Examples J and K. Additionally, formulations are prepared which include a mixture of one of examples A-K with a Carbomer homopolymer type A (Carbopol® 981F polymer, obtainable from Lubrizol Advanced Materials, Inc.)

| Spindle Size No. | Viscosity Range (Cps) |
|---|---|
| 1 | 1-50 |
| 2 | 500-1,000 |
| 3 | 1,000-5,000 |
| 4 | 5,000-10,000 |
| 5 | 10,000-20,000 |

-continued

| Spindle Size No. | Viscosity Range (Cps) |
|---|---|
| 6 | 20,000-50,000 |
| 7 | >50,000 |

The spindle size recommendations are for illustrative purposes only. The artisan of ordinary skill in the art will select a spindle size appropriate for the system to be measured.

TABLE 2

24 hr. Granule Swell data of 3 wt. % granule form of polymer in water

| Polymer | Ex. A | Ex. B | Ex. C | Ex. D | Ex. E | Ex. F | Ex. G | Ex. H | Ex. J | Ex. K | Ex. M | Ex. N |
|---|---|---|---|---|---|---|---|---|---|---|---|---|
| Water gm/gm | 8.56 | 12.38 | 14.07 | High | 6.18 | 4.84 | 6.78 | 6.12 | 3.6 | 9.2 | 7.69 | 7.8 |

TABLE 3

Solubility of 3 wt. % granule form of polymer in various solvents

| Polymer | Ex. A | Ex. B | Ex. C | Ex. F | Ex. K |
|---|---|---|---|---|---|
| Water gm/gm | 8.56 | 12.38 | 14.07 | 4.84 | 9.2 |
| 50:50 EtOH:$H_2O$ | Hazy, soluble & thin | Hazy, soluble & thin | Hazy, soluble & thin | | 22.67 gm/gm |
| 95:5 EtOH:$H_2O$ | Clear, soluble & thin | Clear, soluble & thin | Clear, soluble & thin | | Insoluble |
| 50:50 EtOH:ethyl acetate | Clear, soluble & thin | Clear, soluble & thin | Clear, soluble & thin | | |
| 50:50 EtOH:THF | Clear, soluble & thin | Clear, soluble & thin | Clear, soluble & thin | | Insoluble |
| 90:10 THF:$H_2O$ | Clear, soluble & thin | Clear, soluble & thin | Clear, soluble &thin | | |

TABLE 4

Brookfield Viscosity of Polymers in 50:50 EtOH:$H_2O$ at 20 rpm

| Wt. % Polymer | Ex. A | Ex. B | Ex. C | Ex. D | Ex. E | Ex. F |
|---|---|---|---|---|---|---|
| 4.91 | thin | thin | thin | | | |
| 10 | 360 | 342 | 274 | 120 | 110 | |
| 13.4 | 1392 | 1364 | 1110 | | | |
| 15 | 1280 | 1730 | 1160 | 350 | 350 | |
| 18.6 | 4930 | 3600 | 3880 | | | 2500 |
| 20 | | | 4950, 6640 | 740 | 720 | 3160 |

TABLE 5

Brookfield Viscosity of Polymers in 80:20 EtOH:$H_2O$ at 20 rpm

| Wt. % polymer | Ex. J | Ex. K | Ex. L | Ex. M |
|---|---|---|---|---|
| 4.91 | | 148 | | |
| 10 | Not soluble | | 650 | 210 |
| 15 | Not soluble | 6000 | | 635 |
| 20 | Not soluble | 30,400 | 1450 | 1555 |

Example 3

Soaking Solution and Uptake Studies

The films are cast from an ethanol/water solution either with a 2 inch draw down square of set thickness or an 8 inch draw down bar with adjustable thicknesses using an automatic film applicator with vacuum plate (Byko-drive™ with vacuum plate, Material #2121; BYK Gardner, Md., USA), at a drawdown speed of 1 in/sec. All casting solutions are centrifuged before use to remove bubbles for 30 minutes at 1500 rpm using a Thermo Electron Corporation, IEC Centra GP8 Centrifuge. The film is allowed to dry in a hood at room temperature, in air overnight. The Ex. A-C polymers give good pliable films. The Example J polymer is an extrusion grade and does not dissolve in a water/ethanol mixture and therefore could not be formed into films by casting. Ex. K dissolution is molecular weight dependent and the melt index is recommended to be above 5 to 6 if it is to be solution cast. Good solvent cast films are obtained from the highest water content: solvent combinations (50:50 EtOH:$H_2O$). The addition of a low level of Carbopol® polymer (1:60 Carbopol:polymer K) provides a good cast film. A casting solution for this film is formed from 0.2 wt. % Carbopol® ETD 2020, 12 wt. % Ex. K, in Ethanol:water at a weight ratio of 80/20. Studies with Ex. C and Ex. F polymers suggest that the small amount of Carbopol® ETD 2020 does not influence the film solution uptake.

Degassed blends are used to solvent cast films on polyethylene substrates (5 mil natural high density polyethylene sheets from Griff Paper and Films, PA, USA) and High density polyethylene roll from Griff Paper.

Film samples are cut into either 5×5 cm squares or 3×3 cm squares. The squares are weighed to 4 decimal places. The solvent cast squares show more variability in thickness than the extruded films. The squares are marked for the starting point and the thickness measured at four corners and averaged. The extruded film data in the tables below are measured with the X Direction being perpendicular to the extruded film and Y Direction being parallel to the extruded film.

The square is placed in approximately 50 gm of soaking solution and suspended for 30 minutes in the solution, unless noted otherwise. The square is checked to ensure it does not stick to the container or have surfaces exposed out of the solution.

At the end of soaking time, the square is removed and placed on HDPE (with no additives) and measured for X, Y and Z growth. If strong enough, it is patted dry and weighed.

The wet film is then covered with another sheet of release film and placed in a sealed plastic bag for further testing. Measurements are as follows:

Area growth with time: 5×5 cm film samples are cut and the corners are marked with a black, water insoluble, ink to show the edges. The film is placed in a zippered polyethylene bag with 100 gm of pH 6.8 USP phosphate buffer solution and the bag with film is placed on a grid graph paper. The size is taken at a set time and recorded.

Hydrating Solutions:

Solution uptake studies on the films are conducted in order to understand how ingredients in formulations will influence the properties of the film. The following soaking (hydrating) formulations are evaluated:

1. De-ionized water.
2. glycerin: 10 wt. % USP grade glycerin in DI water.
3. Buffer: USP pH=6.8 phosphate buffer, formed by dissolving 6.805 g potassium phosphate monobasic and 0.896 g sodium hydroxide in water q.s., adding 1 liter of water, and adjusting the pH, if necessary, with 2N HCl or 2N NaOH. The pH is checked for 1 L solution and the volume of acid/base necessary for adjustment is recorded.
4. Aloe Vera Formulation: The formulation included Aloe vera concentrate, available as Activera™ 10X (Clear), supplied by Active Organics. (INCI Name *Aloe Barbadensis* leaf Juice). 2 wt. % of the Aloe vera concentrate is combined with 10 wt. % glycerin and water to give a final concentration of 20 wt % aloe vera in the formulation.

The formulation is preserved with a mixture of phenoxyethanol and ethylhexylglycerin supplied as Euxyl™-PE9010 by Schülke Inc. The resulting aloe formulation is as follows:

Aloe Clear Formulation:

|  | Wt. % | 50 g |
|---|---|---|
| DI Water | 87.48 | 43.74 |
| glycerin (excipient) | 10 | 5.00 |
| Activera ™ 10 × 10:1 | 2 | 1.00 |
| Na₂EDTA | 0.02 | 0.01 |
| Euxyl ™-PE9010 | 0.5 | 0.25 |
| Total | 100 |  |

5. Salicylic Acid Gel Formulation: The salicylic acid gel formulation includes 5 wt. % Curcylic™ 40 (a 40 wt. % solution of salicylic acid in a proprietary stabilizer at 60 wt. %), 10 wt. % glycerin, with a final concentration of salicylic acid of 2 wt. %. The formulation is preserved with Euxyl®PE9010.

Salicylic Acid Gel Formulation

| Ingredient name | Wt. % | 50 g |
|---|---|---|
| DI Water | 84.50 | 42.25 |
| glycerin | 10 | 5.00 |
| Curcylic ®40 | 5 | 2.50 |
| (actual amount of salicylic acid) | (2) |  |
| Euxyl ®-PE9010 | 0.5 | 0.25 |
| Total | 100 |  |

6. Niacinamide Formulation: Niacinamide is a Bgroup vitamin, sometimes referred to as Vitamin PP. It is incorporated into formulations for whitening. Niacinamide is used at 2 wt. % with 10 wt. % glycerin for moisturizing. The formulation is preserved with Euxyl™ PE9010.

Niacinamide Formulation

| Ingredient name | % w/w | 50 g |
|---|---|---|
| Niacinamide | 2 | 1.00 |
| glycerin | 10 | 5.00 |
| Euxyl ®-PE9010 | 0.5 | 0.25 |
| DI Water | 87.5 | 43.75 |
| Total | 100 |  |

Example 4

Solvent Casting of Films with Actives

TABLE 6 shows solvent cast films with an example active agent (salicylic acid or a commercial salicylic acid 40% gel, Curcylic™ 40). For some of the films, a blend of TPU and Carbopol® 981NF polymer (a cross-linked poly(acrylic acid), abbreviated as "981 polymer"), is used. TABLE 7 shows the release of the active agent upon soaking. Salicylic acid content was determined by HPLC.

TABLE 6

Solvent Cast Films with Active Agents

| Example | TPU Polymer | 981 polymer, wt. % | Active agent | Wt. % Salicylic Acid Cast | Wt. % Salicylic Acid found |
|---|---|---|---|---|---|
| Ex. 1 | Ex. C (98 wt. %) |  | salicylic acid 40% gel | 2 | 1.65 |
| Ex. 2 | Ex. F (98 wt. %) |  | salicylic acid 40% gel | 2 | 1.741 |
| Ex. 3 | Ex. C (96.4 wt. %) | 1.61 | salicylic acid | 2 | 1.776 |
| Ex. 4 | Ex. K (96.4 wt. %) | 1.61 | salicylic acid | 2 | 1.821 |
| Ex. 5 | Ex. K (96.4 wt. %) | 1.61 | salicylic acid 40% gel | 2 | 1.699 |
| Ex. 6 | Ex. F (99.5 wt. %) |  | salicylic acid | 0.5 | 0.43 |
| Ex. 6 | Ex. F (97 wt. %) |  | salicylic acid | 3.0 | 2.76 |
| Ex. 8 | Ex. F (96 wt. %) |  | salicylic acid | 4.0 | 3.70 |
| Ex. 9 | Ex. K (97.88 wt. %) | 1.63 | salicylic acid | 0.5 | 0.47 |
| Ex. 10 | Ex. K (97.4 wt. %) | 1.62 | salicylic acid | 1.0 | 0.83 |

TABLE 7

Release of active agent from films

| Example | Release media | % release at 30 mins |
|---|---|---|
| Ex. 4 | Deionized water | 87.0% |
| Ex. 5 | Deionized water | 87.9% |
| Ex. 4 | Buffer | 80.8% |
| Ex. 5 | Buffer | 84.3% |

Uptake Rate

In detailed studies with the Ex. J and K TPUs, it is observed that the films show different rate of uptake depending upon the thickness of the film and that thicker films are found to have slower uptake. Solvent cast Ex. F is studied at 0.254 mm (10 mil) dry thickness at room temperature in the buffer.

Figure 4:
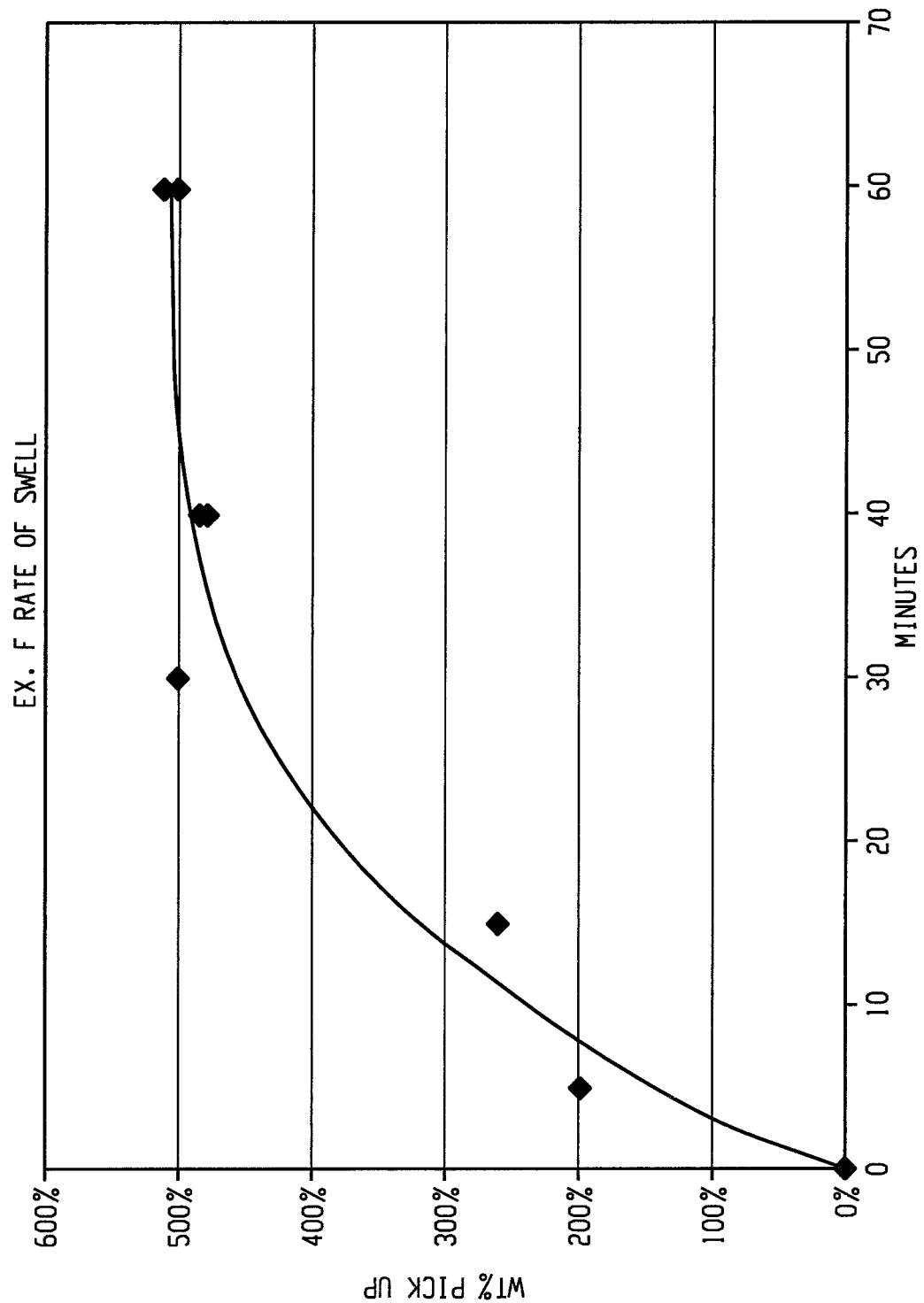
FIG. 4 illustrates rate of swell for an exemplary polyurethane film.

TABLE 8 shows the rate of growth of solvent cast Ex. F at 23° C. in the buffer. FIG. 4 illustrates the results.

TABLE 8

Rate of growth of solvent cast Ex. F at 23° C. in buffer

| Dry Film Thickness (mm) | Time (mins) | gm/gm | volume growth cm³/cm³ | area growth cm²/cm² |
|---|---|---|---|---|
|  | 0 | 0.000 |  |  |
| 0.298 | 5 | 1.983 | 2.141 | 0.988 |
| 0.275 | 15 | 2.618 | 3.524 | 1.592 |
| 0.280 | 30 | 5.025 | 4.355 | 1.856 |
| 0.313 | 40 | 4.791 | 4.251 | 1.957 |
| 0.293 | 60 | 5.018 | 4.222 | 1.855 |
| 0.275 | 40 | 4.860 | 4.556 | 1.924 |
| 0.270 | 60 | 5.108 | 4.505 | 1.958 |

Figure 5:
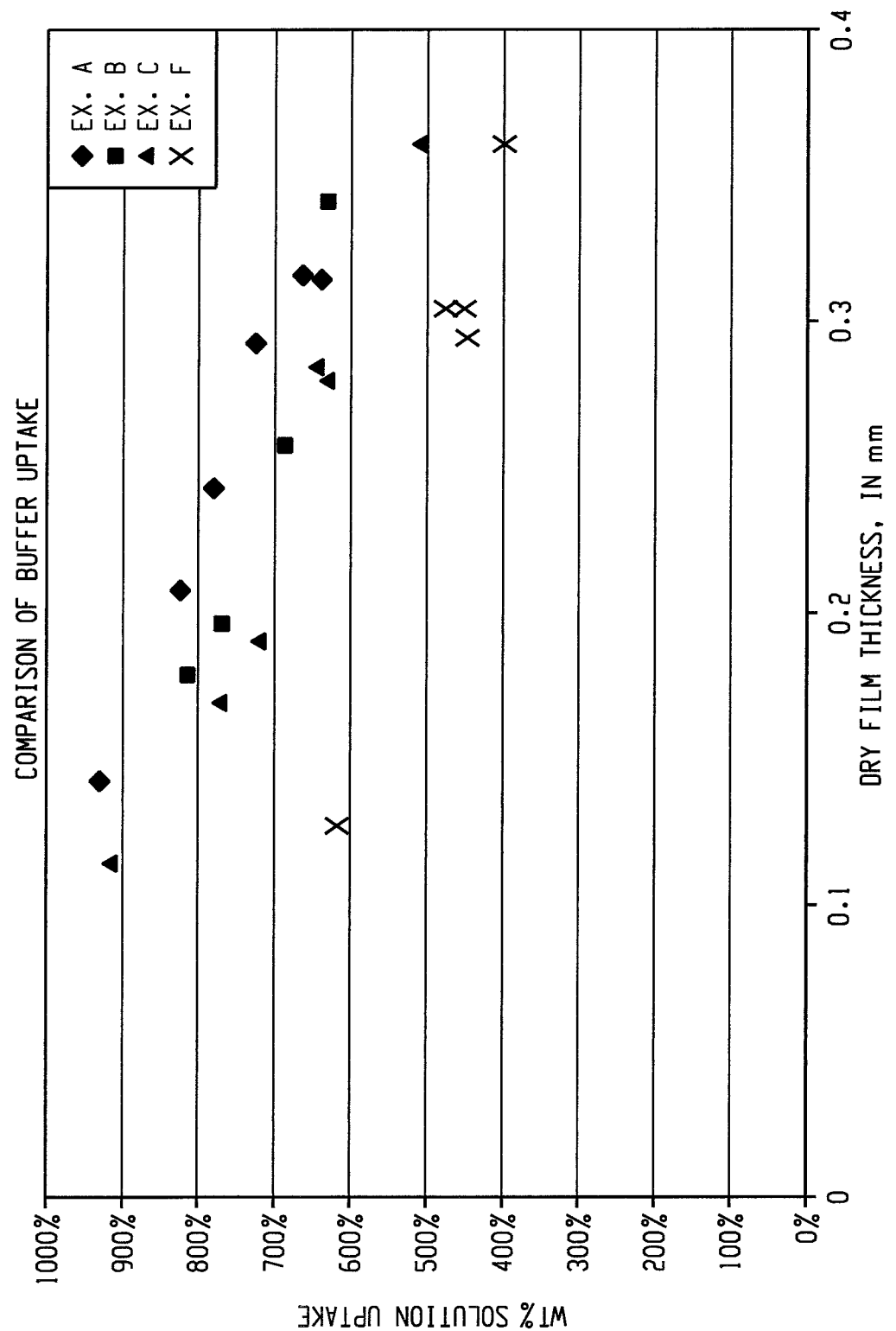
FIG. 5 illustrates buffer uptake for different polyurethane films at different thicknesses.

FIG. 5 shows results for Example F films where the soaking solution is buffer and the soak is stopped at 30 minutes and conducted at room temperature. It can be seen that the Ex. A, B, and C films are all similar in their properties. Ex. F had somewhat lower uptake. The results are shown in greater detail in TABLES 9-12.

Gm/gm growth is calculated as:

$$\frac{(gm \text{ wet} - gm \text{ dry})}{gm \text{ dry}}$$

Volume growth is calculated as:

$$\frac{(\text{Area wet cm}^2 - \text{Area dry cm}^2)}{\text{Area dry cm}^2}$$

Area growth (XY growth) is calculated as:

$$\frac{(\text{Thickness wet mm} - \text{thickness dry mm})}{\text{thickness dry mm}}$$

Z growth is calculated as:

TABLE 9

Growth of Example A solvent cast films in buffer at 23° C. after 30 minutes

| Thickness (mm) | Wt gain gm/gm | dry vol. cm³ | wet vol. cm³ | Vol. growth cm³/cm³ | z growth mm/mm | xy growth cm²/cm² |
|---|---|---|---|---|---|---|
| 0.145 | 9.292 | 0.300 | 2.743 | 8.146 | 1.310 | 2.276 |
| 0.213 | 8.223 | 0.375 | 3.292 | 7.779 | 1.024 | 2.062 |
| 0.247 | 7.790 | 0.600 | 3.994 | 5.657 | 1.061 | 2.133 |
| 0.297 | 7.233 | 0.850 | 4.550 | 4.354 | 1.143 | 1.855 |
| 0.320 | 6.360 | 0.900 | 4.760 | 4.289 | 1.188 | 1.72 |
| 0.323 | 6.612 | 0.750 | 5.411 | 6.215 | 1.217 | 2.027 |

TABLE 10

Growth of EX. B solvent cast films in buffer at 23° C. after 30 minutes

| Thickness (mm) | Wt gain gm/gm | dry vol. cm³ | wet vol. cm³ | Vol. growth cm³/cm³ | z growth mm/mm | xy growth cm²/cm² |
|---|---|---|---|---|---|---|
| 0.182 | 8.113 | 0.456 | 3.498 | 6.668 | 1.534 | 2.026 |
| 0.200 | 7.674 | 0.500 | 3.1416 | 5.283 | 1.2 | 1.856 |
| 0.263 | 6.847 | 0.656 | 4.459 | 5.796 | 1.467 | 1.755 |
| 0.347 | 6.299 | 0.868. | 5.297 | 5.097 | 1.324 | 1.624 |

TABLE 11

Growth of EX. C solvent cast films in buffer at 23° C. after 30 minutes

| Thickness (mm) | Wt gain gm/gm | dry vol. cm³ | wet vol. cm³ | Vol. growth cm³/cm³ | z growth mm/mm | xy growth cm²/cm² |
|---|---|---|---|---|---|---|
| 0.117 | 9.151 | 0.294 | 2.008 | 5.835 | 1.064 | 2.312 |
| 0.173 | 7.716 | 0.425 | 1.694 | 2.987 | 1.739 | 2.133 |
| 0.195 | 7.177 | 0.488 | 4.045 | 7.298 | 1.590 | 2.204 |
| 0.285 | 6.234 | 0.700 | 3.342 | 3.775 | 1.465 | 2.062 |
| 0.290 | 6.438 | 0.725 | 5.141 | 6.091 | 1.483 | 1.856 |
| 0.367 | 5.105 | 0.850 | 4.712 | 4.544 | 1.388 | 1.755 |

TABLE 12

Growth of blend of EX. C and EX. K solvent cast films in buffer at 23° C. after 30 minutes

| Thickness (mm) | Wt gain gm/gm | dry vol. cm³ | wet vol. cm³ | Vol. growth cm³/cm³ | z growth mm/mm | xy growth cm²/cm² |
|---|---|---|---|---|---|---|
| 0.170 | 8.107 | 0.425 | 3.710 | 7.731 | 1.471 | 2.534 |
| 0.223 | 7.708 | 0.556. | 4.659 | 7.377 | 1.449 | 2.42 |
| 0.273 | 6.948 | 0.681 | 5.042 | 6.401 | 1.284 | 2.24 |

TABLE 13

Growth of EX. F solvent cast films in buffer at 23° C. after 30 minutes

| Thickness (mm) | Wt gain gm/gm | dry vol. cm³ | wet vol. cm³ | Vol. growth cm³/cm³ | z growth mm/mm | xy growth cm²/cm² |
|---|---|---|---|---|---|---|
| 0.130 | 6.175 | 0.325 | | | | 2.497 |
| 0.310 | 4.531 | 0.775 | 4.463 | 4.759 | 0.83871 | 2.132 |
| 0.310 | 4.757 | 0.775 | 4.277 | 4.519 | 0.741935 | 2.168 |
| 0.368 | 4.043 | 0.919 | | | | 1.822 |
| 0.300 | 4.495 | 0.75 | 4.163 | 4.551 | 0.966667 | 1.822 |

TABLE 14 shows data for the 30 (or 90) minute solution uptake for films cast from 50/50 ethanol water in buffer, deionized water, and in formulations as described above containing various active agents: Aloe vera formulation with Activera®, niacinamide formulation, and salicylic acid gel formulation with Curcylic™ gel. Data for some extruded films is also shown, denoted by †.

TABLE 14

Growth of solvent cast and extruded films in buffer and in hydrating formulations containing active agents 23° C. after 30 or 90 minutes

| TPU Ex. | Buffer | | Deionized water | | Aloe vera Formulation | | Salicylic acid gel Formulation | | Niacinamide Formulation | |
|---|---|---|---|---|---|---|---|---|---|---|
| | Thickness (mm) | Uptake gm/gm | Thickness (mm) | Uptake gm/gm | Thickness (mm) | Uptake gm/gm | Thickness (mm) | Uptake gm/gm | Thickness (mm) | Uptake gm/gm |
| A | 0.32 | 6.61 | | | 0.28 | 6.93 | 0.27 | 5.67 | | |
| B | 0.26 | 6.85 | | | 0.26 | 637 | 0.27 | 603 | | |
| C | 0.29 | 8.99 | | | 0.25 | 653 | | | 0.25 | 687 |
| D | 0.21 | fell apart | 0.21 | fell apart | | | | | | |
| E | 0.31 | fell apart | | | | | | | | |
| F | 0.28 | 5.02 | 0.31 | 5.34 | 0.31 | 4.60 | 0.25 | 4.57 | 0.25 | 4.49 |
| F † | 0.29 | 4.67 | 0.24 | 4.76 | 0.25 | 5.07 | 0.255 | 4.72 | 0.25 | 5.68 |
| F † | 0.27 | 4.67 | 0.32 | 4.67 | | | | | | |
| F † | 0.38 | 4.14 | 0.37 | 4.35 | 0.37 | 4.27 | 0.38 | 4.02 | 0.38 | 4.44 |
| J † | 0.13 | 3.53 | 0.13 | 3.77 | 0.13 | 4.04 | 0.12 | 4.97 | 0.13 | 4.44 |
| J † | 0.38 | 3.80 | 0.37 | 3.94 | 0.41 | 3.83 | 0.38 | 4.19 | 0.37 | 4.10 |
| K † | 0.27 | 9.06 | 0.27 | 9.27 | 0.15 | 14.0 | 0.14 | 17.12 | | |
| K † | 0.31 | 8.82 | 0.30 | 8.98 | 0.38 | 8.15 | 0.42 | 7.47 | | |
| K † | 0.39 | 8.01 | 0.36 | 8.09 | 0.27 | 11.1 | 0.28 | 11.50 | | |
| L | 0.15 | 9.05 | 0.16 | 9.77 | 0.46 | 6.72 | 0.49 | 5.5 | 0.49 | 6.6 |
| M | 0.18 | 8.50 | 0.22 | 8.49 | 0.33 | 7.57 | 0.29 | 8.20 | 0.29 | 9.04 |
| N † | 0.26 | 5.67 | | | | | 0.3* | 9.79* | | |
| N † | 0.43 | 5.36 | | | | | 0.38* | 8.01* | | |
| 50/50 J/K † | 0.27 | 5.8 | 0.278 | 6.12 | 0.278 | 6.52 | 0.27 | 7.24 | 0.26 | 7.04 |

*90 minute hydration data.

Several of the concept films were also extruded and hydrated in a similar manner as described above. The extruded films showed similar hydration as the solution cast films. The Curcylic soaking solution shows the highest swell progressing in the following order: Curcylic>Niacinamide>Aloe>glycerin>DI water>Buffer. Films formed from Ex. K take up between 1750 and 1200% of the initial weight in solution in the same order. The films are clear when swollen. A film formed from a 50/50 melt mixture of Ex. J and Ex. K also takes up solution in similar order. The films are clear when swollen.

Comparison of the uptake show that the films formed from Ex. J, the 50/50 melt blend, and Ex. K swell at different rates, with Ex. J being consistently about 30% of Ex. K and approximately 60% of the 50/50 melt blend across all solutions. The Ex. K films tend to take longer to reach equilibrium than the Ex. J films of the same thickness.

The active agent remaining in films after soaking is shown in TABLES 15 and 16 for salicylic acid and niacinamide.

For the salicylic acid tests, extruded 0.24 to 0.28 mm films are hydrated in a solution containing Curcylic™ 40 (40 wt. % salicylic acid)/10 wt. % glycerin at room temperature for 30 minutes. The theoretical wt. % of salicylic acid in the hydrated polymer film is calculated by the gm/gm uptake of the solution and the concentration of the salicylic acid found in the hydrating solution.

TABLE 15

Salicylic Acid remaining in films after soaking

| Example Polymer | Curcylic™ 40 in Solution, Wt. % | Salicylic Acid in solution, Wt. % | Average Solution uptake, gm/gm | Average Theoretical Salicylic acid in film, Wt. % | Average Actual Salicylic acid in film, Wt. % |
|---|---|---|---|---|---|
| EX. F | 1.25 | 0.426 | 3.98 | 0.34 | 1.42 |
| EX. F | 2.5 | 0.849 | 3.84 | 0.67 | 2.08 |

TABLE 15-continued

Salicylic Acid remaining in films after soaking

| Example Polymer | Curcylic ™ 40 in Solution, Wt. % | Salicylic Acid in solution, Wt. % | Average Solution uptake, gm/gm | Average Theoretical Salicylic acid in film, Wt. % | Average Actual Salicylic acid in film, Wt. % |
|---|---|---|---|---|---|
| EX. F | 5 | 1.843 | 3.79 | 1.45 | 2.82 |
| EX. F | 7.5 | 2.758 | 3.64 | 2.16 | 3.29 |
| EX. F | 10 | 3.663 | 3.90 | 2.91 | 3.99 |
| Ex. K | 1.25 | 0.426 | 10.68 | 0.426 | 0.46 |
| Ex. K | 2.5 | 0.849 | 10.42 | 0.849 | 0.89 |
| Ex. K | 5 | 1.843 | 10.37 | 1.843 | 1.85 |
| Ex. K | 7.5 | 2.758 | 9.12 | 2.758 | 2.81 |
| Ex. K | 10 | 3.663 | 8.19 | 3.26 | 3.87 |

It can be seen that both example polymers quickly absorb salicylic acid from the solution into the hydrated polymer film. Ex F absorbs more salicylic acid from the solution, selectively concentrating the active into the film.

For the niacinamide tests, extruded 0.24 to 0.28 mm films are hydrated in a solution containing niacinamide/10 wt. % glycerin at room temperature for 30 minutes. The theoretical wt. % of niacinamide in the hydrated polymer film is calculated by the gm/gm uptake of the solution and the concentration of the niacinamide found in the hydrating solution.

TABLE 16

Niacinamide remaining in films after soaking

| Example Polymer | Niacinamide in solution, Wt. % | Average Solution uptake, gm/gm | Average Theoretical Niacinamide in film, Wt. % | Average Actual Niacinamide in film, Wt. % |
|---|---|---|---|---|
| EX. F | 1.08% | 4.59 | 0.89% | 1.15% |
| EX. F | 3.13% | 4.96 | 2.61% | 2.93% |
| EX. F | 5.93% | 5.28 | 4.98% | 4.75% |
| EX. F | 7.67% | 5.76 | 6.54% | 5.47% |
| Ex. K | 1.08% | 10.53 | 0.99% | 1.03% |
| Ex. K | 3.13% | 11.11 | 2.87% | 2.66% |
| Ex. K | 5.93% | 11.72 | 5.46% | 4.28% |
| Ex. K | 7.67% | 12.03 | 7.08% | 5.15% |

It is shown that both example polymers quickly absorb niacinamide from the solution into the hydrated polymer film.

The results indicate that in Examples B and C, the about 83% PEG which is highly hydrophilic, gives the TPU greater water uptake characteristics. The hard segment formed by H12MDI (Desmodur™ W) and 1,4butanediol provides the necessary processing and physical properties to the TPU. The TPU is soluble in 50:50 water:ethanol mixture at up to 15 wt. % solids. Thin films of 0.125 to 0.4 mm can be solvent cast on polyethylene substrates using this solution using a drawdown bar. The films dry in 8-12 hrs. and can be easily peeled off from the substrate. The films when cut in precise dimensions and soaked in excess water pick up almost 100% of water capacity within 15-30 mins, depending on film thickness. The fully hydrated films are shown to retain physical strength and flexibility and are completely transparent.

Example F is a blend of PEG-8000 and PolyG 55-56 in the soft segment. Poly G 55-56 enhances the "cling" characteristics of the hydrated film on the skin as it loses water over time. Also, increased film flexibility is obtained with the addition of PolyG 55-56. The amount of PolyG 55-56 decreases the amount of water absorbed by the polymer and balances the hydrophobic hydrophilic properties. As seen in TABLES 15 and 16, the absorption of active is also related to the character of polyol B. Blends of polyurethanes (Ex. B or Ex. F with Ex. K) in a 50:50 ratio with are also found to have desirable characteristics. Adding a Carbopol® polymer in small quantities to the TPU solution is found to increase film strength while maintaining flexibility and water uptake properties.

Example 5

Preparation of Simulated Face Masks and Transdermal Patches a) Preparation of a Film Containing Caffeine Simulated face masks are prepared from round samples of about 0.8 cm diameter weighing approximately 15-25 mg from a film of polymer K. The sample is placed in approximately 5 mL of soaking solution (TABLE 17) and suspended for 30 minutes in the solution. The sample is periodically checked to ensure it remains totally immersed in the solution. At the end of soaking time, the sample is removed and reweighed (final sample diameter, about 2.1 cm).

TABLE 17

Soaking solution containing caffeine

| Ingredients (INCI) | % (w/w) |
|---|---|
| water | 97.60 |
| caffeine | 2 |
| disodium EDTA | 0.2 |
| potassium sorbate | 0.1 |
| sodium benzoate | 0.1 |
| citric acid | cs to pH 4 |

The concentration of caffeine in the wet polymer sample is measured by HPLC and is shown in TABLE 18 (HPLC: Shimadzu Scientific Prominence System; Column: Macherey-Nagel Nucleosil™ 120-5 $C_{18}$, L×I.D.: 250×4.6 mm; Carrier Phase: A: Water, B: Methanol (65:35 v/v); Oven Temperature: Room Temperature (approx. 22° C.); Flow Rate: 1 mL/min.; UV detection: 254 nm).

TABLE 18

Final concentration of caffeine after 30 min soaking period

| Sample | Dry weight (mg) | Wet weight (mg) | % caffeine (w/w), vs. wet polymer |
|---|---|---|---|
| 1 | 20.0 | 259.5 | 2.59 |
| 2 | 17.0 | 217.4 | 2.64 |
| 3 | 18.0 | 240.9 | 2.63 |
| 4 | 20.0 | 252.9 | 2.63 |
| 5 | 19.0 | 235.9 | 2.60 |
| 6 | 24.0 | 319.0 | 2.57 | b) Preparation of a Film Containing Dimethylmethoxy Chromanyl Palmitate

Round samples (0.8 cm in diameter and 0.305 mm thick) weighing approximately 25-31 mg are prepared from a film of Polymer K. The sample is immersed in a vessel containing approximately 4 mL of a dimethylmethoxy chromanyl palmitate soaking solution (TABLE 19, all weight percents on an undiluted basis) for 30 minutes. The sample is periodically checked to ensure that it remains totally immersed in the soaking solution and does not adhere to the vessel surface. At the conclusion of the 30 min. soaking period the sample is removed from the dimethylmethoxy chromanyl palmitate solution and re-weighed (TABLE 20). The final sample diameter is about 2.0 cm.

TABLE 19

Soaking solution containing Liposomes of Dimethylmethoxy Chromanyl Palmitate

| Ingredients (INCI) | % (w/w) |
| --- | --- |
| water | 62.2 |
| propanediol | 20 |
| lecithin | 6 |
| ethylhexyl methoxycinnamate | 5 |
| phenoxyethanol | 2.6 |
| dimethylmethoxy chromanyl palmitate | 2 |
| inulin lauryl carbamate, water, ethyl pyrrolidone | 0.2 |

The concentration of dimethylmethoxy chromanyl palmitate in the wet polymer is measured by HPLC (TABLE 20).

TABLE 20

Final concentration of dimethylmethoxy chromanyl palmitate in % versus wet polymer and weight change after soaking with a solution containing Liposomes of dimethylmethoxy chromanyl palmitate

| Sample | Dry weight (mg) | Wet weight (mg) | % Dimethylmethoxy chromanyl palmitate (w/w), vs. wet polymer |
| --- | --- | --- | --- |
| 1 | 28.7 | 426.0 | 0.994 |
| 2 | 28.7 | 382.3 | 0.888 |
| 3 | 27.2 | 358.7 | 1.074 |
| 4 | 25.3 | 355.8 | 0.964 |
| 5 | 31.0 | 446.6 | 1.009 | c) Preparation of a Film Containing Arbutin

Simulated face masks are prepared from round samples of a film of polymer K of about 0.8 cm diameter with a total weight of about 25-35 mg. The film is placed in approximately 4 mL of soaking solution containing arbutin [(2R,3S,4S,5R,6S)-2Hydroxymethyl-6(4hydroxyphenoxy)oxane-3,4,5triol] (TABLE 21) and suspended for 30 minutes in the solution. The sample is periodically checked to ensure that it remains totally immersed in the soaking solution and does not adhere to the vessel surface. At the conclusion of the 30 min. soaking period the sample is removed from the arbutin solution and re-weighed. The final sample diameter is about 2.2 cm.

TABLE 21

Arbutin Soaking Solution

| Ingredients (INCI) | % (w/w) |
| --- | --- |
| water | 95.6 |
| arbutin | 4 |
| disodium EDTA | 0.2 |
| potassium sorbate | 0.1 |
| sodium benzoate | 0.1 |
| sodium hydroxide | cs to pH 5.5 |

The concentration of Arbutin in the wet polymer is measured by HPLC (as described above) (TABLE 22).

TABLE 22

Final concentration of Arbutin in % versus wet polymer and weight change after soaking with a solution containing Arbutin

| Sample | Dry weight (mg) | Wet weight (mg) | % Arbutin (w/w), vs. wet polymer |
| --- | --- | --- | --- |
| 1 | 34.1 | 491.7 | 1.61 |
| 2 | 29.1 | 437.0 | 6142 |
| 3 | 30.9 | 453.9 | 1.78 |
| 4 | 25.7 | 400.0 | 1.42 |
| 5 | 32.6 | 497.5 | 1.61 |
| 6 | 33.2 | 490.6 | 1.45 | d) Preparation of a Film Containing Acetyl Hexapeptide-37

A simulated face mask is prepared from a round piece of polymer K of about 0.8 cm diameter with a total weight of about 25-30 mg. The film is placed in approximately 5 mL of soaking solution containing acetyl hexapeptide-37 obtained from Lipotec, S.A. (TABLE 23) and suspended for 90 minutes in the solution. The sample is periodically checked to ensure that it remains totally immersed in the soaking solution and does not adhere to the vessel surface. At the conclusion of the 90 min. soaking period the sample is removed from the acetyl hexapeptide-37 solution and re-weighed. The final sample diameter is about 2.2 cm.

TABLE 23

Acetyl Hexapeptide-37 Soaking solution

| Ingredients (INCI) | % (w/w) |
| --- | --- |
| water | 49.95 |
| butylene glycol | 50 |
| acetyl hexapeptide-37 | 0.05 |

The concentration of acetyl hexapeptide-37 in the wet polymer is measured by HPLC (TABLE 24).

TABLE 24

Final concentration of Acetyl Hexapeptide-37 in % versus wet polymer and weight change after soaking with a solution containing Acetyl Hexapeptide-37

| Sample | Dry weight (mg) | Wet weight (mg) | % Acetyl Hexapeptide-37 (w/w), vs. wet polymer |
| --- | --- | --- | --- |
| 1 | 27.2 | 352.2 | 0.0401 |
| 2 | 25.9 | 344.1 | 0.0379 |
| 3 | 26.2 | 341.0 | 0.0365 |
| 4 | 26.3 | 350.6 | 0.0367 | e) Preparation of a Film Containing Acetyl Hexapeptide-8

A simulated face mask is prepared from a round piece of polymer K of about 0.8 cm diameter with a total weight of about 20-30 mg. The film is placed in approximately 5 mL of soaking solution containing acetyl hexapeptide-8 obtained from Lipotec, S.A. (TABLE 25) and suspended for 90 minutes in the acetyl hexapeptide-8 solution. The sample is checked to ensure it does not stick to the container or have surfaces exposed out of the solution. At the end of the 90 minute soaking time, the square is removed and weighed again (final piece diameter: 2.2 cm).

TABLE 25

Acetyl Hexapeptide-8 Soaking Solution

| Ingredients (INCI) | % (w/w) |
|---|---|
| water | 99.65 |
| Phenonip ™ (phenoxyethanol, methylparaben, butylparaben, ethylparaben, isobutylparaben, propylparaben) | 0.3 |
| acetyl hexapeptide-8 | 0.05 |

The concentration of acetyl hexapeptide-8 in the wet polymer is measured by HPLC, as described above (TABLE 26).

TABLE 26

Final concentration of Acetyl Hexapeptide-8 in % versus wet polymer and weight change after soaking with a solution containing Acetyl Hexapeptide-8

| Sample | Dry weight (mg) | Wet weight (mg) | % Acetyl Hexapeptide-8 (w/w), vs. wet polymer |
|---|---|---|---|
| 1 | 27.2 | 402.8 | 0.0418 |
| 2 | 28.9 | 428.5 | 0.0434 |
| 3 | 28.0 | 407.1 | 0.0425 |
| 4 | 23.4 | 338.1 | 0.0420 |

The same study is performed with a lower concentration of peptide, as follows. A round piece of the same polymer of about 0.8 cm diameter with a total weight of about 20-30 mg is placed in approximately 5 mL of soaking solution formed by a 1/5000 dilution with water of the soaking solution described in TABLE 25 and suspended for 90 minutes in the solution. The piece is checked to ensure it does not stick to the container or have surfaces exposed out of the solution. At the end of the soaking time, the square is removed from the low concentration acetyl hexapeptide-8 solution and weighed again (final piece diameter: 2.2 cm).

The concentration of acetyl hexapeptide-8 in the wet polymer is measured by HPLC (TABLE 27).

TABLE 27

Final concentration of Acetyl Hexapeptide-8 in % versus wet polymer and weight change after soaking with a dilution 1/5000 in water of a solution containing Acetyl Hexapeptide-8

| Sample | Dry weight (mg) | Wet weight (mg) | % Acetyl Hexapeptide-8 (w/w), vs. wet polymer |
|---|---|---|---|
| 1 | 27.3 | 355.8 | 0.0017 |
| 3 | 23.6 | 320.2 | 0.0019 | f) Preparation of a Film Containing a Dimethylmethoxy Chromanyl Palmitate Fluid Emulsion A square of polymer K of about 3×3 cm with a total weight about 444 mg is placed in approximately 200 mL of soaking emulsion containing dimethylmethoxy chromanyl palmitate (obtained from Lipotec, S.A.) (TABLE 28) and suspended for 60 minutes in the solution. The sample is periodically checked to ensure that it remains totally immersed in the soaking solution and does not adhere to the vessel surface. At the conclusion of the 60 minute soaking time, the square is removed from the dimethylmethoxy chromanyl palmitate soaking emulsion and re-weighed (final size: 9.27×9.27 cm, final weight: 3.909 g).

TABLE 28

Soaking Solution Containing a Dimethylmethoxy Chromanyl Palmitate Emulsion

| Ingredients (INCI) | % (w/w) |
|---|---|
| water | csp 100 |
| sodium hydroxide | cs to pH 6.94 |
| disodium EDTA | 0.2 |
| potassium sorbate | 0.1 |
| acetyl hexapeptide-8 | 0.05 |
| acrylates copolymer | 1 |
| acrylates/beheneth-25 methacrylate copolymer | 0.25 |
| caprylic/capric triglyceride | 33 |
| methyl glucose dioleate | 2.5 |
| dimethylmethoxy chromanyl palmitate | 2 |
| phenoxyethanol | 0.5 | g) Preparation of a Film Containing Hyaluronic Acid

A square of polymer K of about 3×3 cm with a total weight of about 358 mg is placed in approximately 200 mL of soaking solution containing hyaluronic acid (TABLE 29) and suspended for 60 minutes in the solution. The piece is checked to ensure it does not stick to the container or have surfaces exposed out of the solution. At the end of soaking time, the square is removed and weighed again (final size: 12.3×12.3 cm, final weight: 4.164 g).

TABLE 29

Hyaluronic Acid Soaking Solution

| Ingredients (INCI) | % (w/w) |
|---|---|
| water | csp 100 |
| sodium benzoate | 0.1 |
| disodium EDTA | 0.2 |
| potassium sorbate | 0.1 |
| sodium hyaluronate | 0.5 | h) Preparation of Films Containing Diclofenac Sodium

3×3 cm squares are cut from extruded films of polymers F, K and N. The weight of each square is measured by a Mettler Toledo AE100 Balance. Thickness at 4 corners is measured using a Mitutoyo Digital Thickness Gauge, and the thickness of the square is expressed as the average of the four corners. The X and Y dimensions of each square are recorded. A soaking solution is prepared according to TABLE 30. First, 10% glycerin and 0.25% Euxyl® PE9010 (a preservative) obtained from Schulke & Mayr GmbH are added to deionized water, and the solution is stirred for 15 minutes. Then, 0.84% of Diclofenac Sodium [2-(2,6-dichloranilino)phenylacetic acid], obtained from Spectrum Chemical Mfg. Corp. is added and stirred for 1 hour or until clear. Diclofenac sodium is a nonsteroidal antiinflammatory drug (NSAID) taken or applied to reduce inflammation and as an analgesic reducing pain. The film squares are placed into the soaking solution, and saturated for 30 minutes. The sample squares are then removed from the solution and blotted dry with a paper towel. The samples are measured for weight, thickness and the X and Y dimensions. Uptake and dimension change are calculated based on the measurement above.

TABLE 30

Soaking solution containing Diclofenac Sodium

| INGREDIENT | % IN WEIGHT |
| --- | --- |
| deionized water | 88.91 |
| glycerin | 10 |
| diclofenac sodium | 0.84 |
| Euxyl ® PE9010 | 0.25 |

The active agent remaining in films after soaking is shown in TABLE 31.

For the diclofenac sodium hydration, extruded 0.33 to 0.37 mm films are hydrated in a solution containing 0.84 wt. % diclofenac sodium/10 wt. % glycerin at room temperature for 30 minutes. The theoretical wt. % of diclofenac sodium in the hydrated polymer film is calculated by the gm/gm uptake of the solution and the concentration of the diclofenac sodium found in the hydrating solution.

TABLE 31

Diclofenac Sodium remaining in films after soaking

| Example Polymer | Diclofenac Sodium Solution, Wt. % | Average Solution uptake, gm/gm | Average Theoretical Diclofenac Sodium in film, Wt. % | Average Actual Diclofenac Sodium in film, Wt. % |
| --- | --- | --- | --- | --- |
| Ex. K | 0.84 | 10.70 | 0.81 | 1.174 |
| Ex. N | 0.64 | 6.12 | 0.59 | 1.095 |
| Ex. F | 0.54 | 6.05 | 0.46 | 0.901 |

It can be seen that all example polymers quickly absorb diclofenac sodium from the solutions into the hydrated polymer films. Films of K, N and F all absorb more diclofenac sodium from the hydrating solution, selectively concentrating the active into the film. Film K has a higher gm/gm solution uptake than N and F, while lower ratio of actual active amount to theoretical active amount.

i) Preparation of Films Containing Lidocaine HCl

Lidocaine HCl stabilizes the neuronal membrane by inhibiting the ionic fluxes required for the initiation and conduction of impulses, thereby effecting local anesthetic action. It is incorporated into this formulation for pain relief.

3×3 cm squares are cut from extruded films of polymers of Ex. F, K and N and weighed and thickness measured as for Example 5h. A soaking solution is prepared according to TABLE 32. First, a phosphate buffer is prepared by adding monopotassium phosphate and sodium hydroxide to deionized water, and the pH is measured (6.8). Into the phosphate buffer, 10% glycerin and 0.25% Euxyl® PE9010 are added. The solution is stirred for 15 minutes. Then 5% Lidocaine HCl obtained from Spectrum Chemical Mfg. Corp. is added and stirred for 15 minutes. The solution is stirred for 30 minutes at room temperature before use.

The pH is measured (6.43). The film squares are placed into the soaking solution and saturated in the solution for 90 minutes. Then, the sample squares are removed from the solution and blotted dry with a paper towel. The samples are measured for weight, thickness and the X and Y dimensions. Uptake and dimension change are calculated based on the measurement above.

TABLE 32

Soaking solution containing Lidocaine HCl (pH 6.4)

| INGREDIENT | Wt. % |
| --- | --- |
| Phosphate Buffer (pH 6.8) in Deionized Water | 83.9799 |
| Monopotassium Phosphate | 0.6805 |
| Sodium Hydroxide | 0.0896 |
| glycerin | 10 |
| Lidocaine HCl | 5 |
| Euxyl ® PE9010 | 0.25 |

Another Soaking Solution is prepared at pH 4.6 (TABLE 33).

The active agent remaining in films after soaking in Lidocaine HCl solution is shown in TABLE 33.

TABLE 33

Lidocaine Hydrochloride remaining in films after soaking

| Example Polymer | Lidocaine HCl in solution, Wt. % | Average Solution uptake, gm/gm | Average Theoretical Lidocaine HCl in film, Wt. % | Average Actual Lidocaine HCl in film, Wt. % |
| --- | --- | --- | --- | --- |
| K | 5 | 13.12 | 4.98 | 4.921 |
| F | 5 | 4.29 | 4.98 | 4.947 |
| N | 5 | 7.32 | 4.50 | 4.600 |

For the lidocaine hydrochloride hydration, films of Ex. K and F are extruded at 0.28 to 0.31 mm and are hydrated in a solution containing 5 wt. % lidocaine hydrochloride/10 wt. % glycerin (pH 6.4) at room temperature for 90 minutes. Films of Ex. N are extruded at 0.28 to 0.31 mm and are hydrated in a solution containing 5 wt. % lidocaine hydrochloride/10 wt. % glycerin (pH 4.6) at room temperature for 90 minutes. The theoretical wt. % of lidocaine hydrochloride in the hydrated polymer film is calculated by the gm/gm uptake of the solution and the concentration of the lidocaine hydrochloride found in the hydrating solution.

The results suggest that within 90-minute hydration, three example polymers absorb from the solution to form hydrated films and have different solution uptake ability. Average solution uptake rank in an increasing order is F<N<K. For all three example polymers, average actual active in film is equivalent to average theoretical active in film, indicating they are not selectively concentrating the active into the film.

j) Release of Actives from Films

Release of diclofenac sodium from example films is studied as follows. Six pieces of 3×3 cm diclofenac sodium-containing hydrated films of each kind are cut from example films prepared in Example 5h. Each piece is placed against a glass disc and retained with a 17 mesh Teflon screen. Four Teflon clip/feet retain the assembly and position the assembly in a dissolution vessel. The transdermal patch retainer is USP 724 compliant and purchased from Quality Lab Accessories. USP dissolution apparatus 5 (paddle over disk) is applied to test active release from the example films. VK7010 with 1000 ml vessels and stainless steel paddles (obtained from Agilent) are used to perform the release test of diclofenac sodium loaded films. The dissolution vessels are loaded with 800 ml of release medium (degassed phosphate buffered saline pH=7.4). The temperature of release medium is kept at 32.0±0.5° C. throughout the test (the temperature of the release medium is selected to reflect the physiological skin conditions). The paddle height is set to 2.5 cm from the bottom of the vessel to the disc. The paddle rotation speed is 50 rpm. The samples (10 ml) are withdrawn automatically by Varian VK 810 sampling station at time points 2, 5, 9, 12, 15, 20, 30, 45, 60, 90, and 120 min, and analyzed by Cary® 50 UV-Vis (Agilent, USA). TABLE 34 shows release of diclofenac sodium from the films.

TABLE 34

Release of diclofenac sodium from films

| Example | Release media | % release at 120 mins |
|---|---|---|
| Ex. K | Phosphate buffered saline | 72.7 |
| Ex. N | Phosphate buffered saline | 77.4 |
| Ex. F | Phosphate buffered saline | 77.3 |

Release of lidocaine HCl from example films is studied as described above for the diclofenac sodium using six pieces of 5×5 cm hydrated lidocaine HCl-containing films of each kind which are cut from example films prepared in Example 5i. TABLE 35 shows release of diclofenac sodium from the films.

TABLE 35

Release of lidocaine HCl from films

| Example | Release media | % release at 30 mins |
|---|---|---|
| K | Phosphate buffered saline | 87.3 |
| F | Phosphate buffered saline | 79.5 |

Example 5

Preparation of Simulated Face masks and Transdermal Patches from Solvent Cast Films a) Stock Solutions Polymer stock solutions (Solutions A, B, C) are prepared using Ex. F and K polymers and stirred at room temperature until all ingredients dissolved, according to TABLE 36 below.

TABLE 36

| Ingredients | Solution A (Ex. F) | Solution B (Ex. F) | Solution C (Ex. K) |
|---|---|---|---|
| Polymer (gm) | 135 | 288.75 | 150 |
| Ethanol (gm) | 307.5 | 288.75 | 480 |
| Water (gm) | 307.5 | 172.5 | 123 |
| Wt. % polymer in Solution | 18 | 23 | 19.92 | b) Menthol-Containing Casting Mixtures

Casting mixtures of solution A and a 20 wt. % menthol stock solution (Solution D) are prepared as shown in TABLE 37 and stirred until homogeneous. Films are cast using a 2 in (5.08 cm) 100 mil (2.54 mm) draw down bar on LLDPE sheets to give clear, soft pliable films. The films are dried overnight and the thickness measured.

TABLE 37

| | Sample | | | | |
|---|---|---|---|---|---|
| | 37.1 | 37.2 | 37.3 | 37.4 | 37.5 |
| Solution A (18 wt. % polymer) (gm) | 110 | 110 | 110 | 110 | 110 |
| Solution D (20 wt. % menthol) (gm) | 1 | 2.5 | 5.21 | 7.45 | 8.61 |
| polymer in casting solution (gm) | 19.8 | 19.8 | 19.8 | 19.8 | 19.8 |
| menthol in casting solution (gm) | 0.2 | 0.5 | 1.042 | 1.49 | 1.722 |
| Theoretical wt. % menthol in dry film | 1.0% | 2.5% | 5.0% | 7.0% | 8.0% |
| Dry film Thickness (mm) | 0.23 | 0.20 | 0.31 | 0.27 | 0.30 | c) Menthol and Methyl Salicylate-Containing Casting Mixtures

Casting mixtures of solution B and a 20 wt. % menthol and 10 wt. % methyl salicylate stock solution (Solution E) are prepared as shown in TABLE 38 and stirred until homogeneous. Films are cast using a 2 in (5.08 cm) 125 mil (3.175 mm) draw down bar on LLDPE sheets to give clear, soft pliable films. The films are dried overnight and the thickness measured.

TABLE 38

| | Sample | | | | |
|---|---|---|---|---|---|
| | 38.1 | 38.2 | 38.3 | 38.4 | 38.5 |
| Solution B (polymer) (gm) | 64 | 62 | 60 | 59 | 58 |
| Solution E (20 wt. % menthol and 10 wt. % methyl salicylate) (gm) | 1.52 | 3.03 | 4.55 | 6.17 | 7.85 |
| polymer in casting solution (gm) | 14.72 | 14.26 | 13.8 | 13.57 | 13.34 |
| menthol in casting solution (gm) | 0.304 | 0.606 | 0.91 | 1.234 | 1.57 |
| methyl salicylate in casting solution (gm) | 0.152 | 0.303 | 0.455 | 0.617 | 0.785 |
| Theoretical wt. % menthol | 2% | 4% | 6% | 8% | 10% |
| Theoretical wt. % methyl salicylate | 1% | 2% | 3% | 4% | 5% |
| Dried film thickness (mm) | 0.41 | 0.38 | 0.34 | 0.4 | 0.31 |

A stock solution containing Carbopol® 981 (Solution F) is prepared according to TABLE 39.

TABLE 39

| Ingredient | Solution F |
|---|---|
| Polymer (Carbopol ® 981) (gm) | 6 |
| Ethanol (gm) | 197 |
| Water (gm) | 197 |
| Tris (30%) (gm) | 11.5 |
| Wt. % polymer | 1.46 |

Polymer Solution C (470 gm) is mixed with Carbopol® solution F (104.4) to give a Stock Solution G containing 0.26 wt. % Carbopol® 981.

d) Menthol/Carbopol-Containing Casting Mixtures

Casting mixtures of the Stock solution G (containing polymer with Carbopol® 981) and the stock Solution D (menthol) at the indicated concentrations shown in TABLE 40 are combined and stirred until homogeneous. Films are cast using a 2 in (5.08 cm) 125 mil (3.175 mm) draw down bar on HDPE and dried overnight to give white films of the indicated thickness.

TABLE 40

| | Sample | | | | |
|---|---|---|---|---|---|
| | 40.1 | 40.2 | 40.3 | 40.4 | 40.5 |
| Solution G (14.1 wt. % Ex. K) polymer (gm) | 110 | 110 | 110 | 110 | 110 |
| Solution D (20 wt. % menthol) (gm) | 0.91 | 2.45 | 5.02 | 6.46 | 7.33 |
| polymer in casting solution (gm) | 15.51 | 15.51 | 15.51 | 15.51 | 15.51 |
| menthol in casting solution (gm) | 0.182 | 0.49 | 1.004 | 1.292 | 1.466 |
| Theoretical wt. % menthol in film | 1.2 | 3.1 | 6.1 | 7.7 | 8.6 |
| Dried film thickness (mm) | 0.40 | 0.40 | 0.55 | 0.24 | 0.34 | e) Menthol and Methyl Salicylate/Carbopol-Containing Casting Mixtures

Casting mixtures of the Stock solution G (containing polymer with Carbopol® 981) and the stock Solution E (menthol and methyl salicylate) at the indicated concentrations shown in TABLE 41 are combined and stirred until homogeneous. Films are cast using a 2 in (5.08 cm) 125 mil (3.175 mm) draw down bar on HDPE and dried overnight to give white films.

TABLE 41

| | Sample | | | | |
|---|---|---|---|---|---|
| | 41.1 | 42.2 | 42.3 | 42.3 | 42.3 |
| Solution G (14.1 wt. Ex. K) (gm) | 110 | 110 | 110 | 110 | 110 |
| Solution E (20 wt. % menthol and 10 wt. % methyl salicylate) (gm) | 1.86 | 3.72 | 5.66 | 7.66 | 9.72 |
| polymer in casting solution (gm) | 15.51 | 15.51 | 15.51 | 15.51 | 15.51 |
| menthol in casting solution (gm) | 0.372 | 0.744 | 1.132 | 1.532 | 1.944 |
| methyl salicylate in casting solution (gm) | 0.186 | 0.372 | 0.566 | 0.766 | 0.972 |
| Theoretical wt. % menthol in film | 2% | 4% | 7% | 9% | 11% |
| Theoretical wt. % methyl salicylate in film | 1% | 2% | 3% | 4% | 5% | f) Capsaicin-Containing Casting Mixtures

A stock solution (Solution H) is prepared from 0.0762 gm Capsaicin in 25 ml ethanol (0.003104 mg/µl Capsaicin).

Stock Solution A (18 wt. % polymer) is prepared using the same weight percent of ingredients as used in TABLE 35.

Stock Solution A and stock Solution H are combined in the amounts shown in TABLE 42 and are blended until homogeneous. Films are cast using a 2 in (5.08 cm) 100 mil (2.54 mm) 2 draw down bar on LDPE sheets to give clear soft pliable films. The films are dried overnight and the dried thickness measured. Capsaicin content was measured by HPLC.

TABLE 42

| Capsaicin Films | | | |
|---|---|---|---|
| | Sample | | |
| | 43.1 | 43.2 | 43.3 |
| Solution A (18 wt. % polymer Ex. F) (ml) | 90 | 90 | 90 |

TABLE 42-continued

| Capsaicin Films | | | |
|---|---|---|---|
| | Sample | | |
| | 43.1 | 43.2 | 43.3 |
| Capsaicin stock solution H (ml) | 2.7 | 5.4 | 13.5 |
| Polymer in casting solution (gm) | 16.2 | 16.2 | 16.2 |
| Capsaicin in casting solution (gm) | 0.00823 | 0.016459 | 0.041148 |
| Theoretical wt. % capsaicin in film | 0.05% | 0.10% | 0.25% |
| Dried film thickness (mm) | 0.23 | 0.24 | 0.25 |
| Measured Capsaicin in Film (wt. %) | 0.0476% | 0.0946% | 0.248% | g) Wet Patch with Cover

A 12 mil (0.3 mm) thick extruded film of Ex. K produced from Stock Solution C (19.92 wt. % polymer) is hydrated in the Aloe Vera Clear formulation of Example 3 for 30 minutes to produce a 2x5 cm hydrated patch. The patch is placed on the forearm and covered to hold it in place by an adhesive transparent film dressing Tegaderm™ (3M Company). The adhesive dressing is 4 in (10.16 cm) by 4.75 in (12.065 cm). The hydrated patch is held in place for 0.5 hours and then removed demonstrating the utility of the hydrated patch as a dermal delivery system under a barrier film.

Example 6

Skin Studies a) Skin Study with Caffeine

A percutaneous absorption study is performed on pig skin test samples obtained from the back of domestic pigs (Sus domesticus) weighing about 30 kg. The pig skin is dermatomed to a thickness of about 500 microns and then test discs having a diameter of 2.5 cm are sectioned from the dermatomed skin. An extruded polymer film of polymer K is loaded is with 1.8% caffeine (as described for Example 5A). The loaded films are applied to the sample discs (in contact with the stratum corneum) for 30 minutes. Different layers of the film treated skin (stratum corneum, epidermis and dermis) are separated, assayed and analyzed for the quantity of caffeine and permeation into the respective layers of the skin. The quantitative analysis for caffeine and is conducted by HPLC utilizing the instrumentation identified above.

Additionally, the same solutions utilized to load the polymer films are topically applied across the entire surface of the stratum corneum of comparative pig skin disc samples prepared as above. The topically treated discs are allowed to stand for 30 mins. before being assayed. The topically coated discs are used to compare the impact of the application of the active ingredient loaded polymer film with topical application of active ingredients on dermal absorption. The OECD 428 methodology (OECD Guideline for the testing of chemicals: Skin absorption: in vitro Method, Paris, adopted 13 Apr. 2004) is followed for the experimental design.

The treated skin discs are placed between the upper and the lower chambers of a Franz diffusion cell (PermeGear, Inc., Hellertown, Pa.) with a contact area of 1.77 $cm^2$. The lower chamber contained the receptor fluid (PBS solution, Sigma-Aldrich Co. LLC). The integrity of the skin is evaluated by measuring the transepidermal water loss (TEWL). Only the sample discs with a TEWL value lower than 15 g/$m^2$ hr. are used in the experiment. A value higher than 15 g/$m^2$·hr. could indicate the presence of a hole in the biopsied skin sample. The receptor fluid is collected, and the bottom of the skin is washed with distilled water and added to the receptor fluid to a final volume of 10 mL with extraction solution (H₂O, pH 3.0). The collected receptor fluid is analyzed by HPLC as described above. No caffeine was present in the analyzed fluids indicating that the active remained in the skin samples.

The quantities of caffeine that permeated into each of the three different layers of the skin samples (stratum corneum, epidermis and dermis) are collected separately as follows. To remove residual formulation remaining on the surface of the stratum corneum of the skin samples, the skin surface is washed once with a surfactant solution (0.5 wt. % sodium dodecyl sulfate in water) and twice with pure water. The stratum corneum of the treated skin samples is adhesively separated from the underlying layers by applying 10 adhesive strips on the skin surface at a constant pressure (100 g/cm²) for 5 seconds. In order to minimize the damage on the dermoepidermal junction, the strips are applied and removed in different directions (rotations of)90°. All of the strips (containing the adhered stratum corneum cells) are placed in 2 mL of extraction solution.

The epidermis is separated from the dermis by heating the remaining skin samples at 80° C. for approximately 5 seconds. The remaining separated epidermis layer also is placed in 1 mL of extraction solution. The remaining dermis layer is cut into small pieces and placed in 1 mL of extraction solution. The exacted actives for each of the skin layers are assayed by HPLC described above to determine the quantity of active that permeated into each layer of the pig skin test sample.

Additionally, a caffeine solution with the same concentration of caffeine is used to compare the impact of the polymer on dermal absorption.

Additionally, the water activity of the dried polymer is studied in order to analyze possible microbiological risks. The water activity is the partial vapor pressure of water in a substance divided by the standard state partial vapor pressure of water. When the value is lower there is less risk of microbiological contamination.

In parallel, a sensory evaluation was conducted by a panel of Asian participants on several key cosmetic attributes to assess the robustness and in-use sensory experience offered by the polymer hydrogel film compared to classic facial mask sheets.

The polymer loaded with caffeine allows applying a very high concentration of caffeine, much more than that specified in the OECD 428 guideline. For that reason, four different experiments are done with the same concentration of caffeine.
1. 1.8% caffeine in the experimental polymer film, applied for 30 minutes (50 mg total caffeine applied).
2. 1.8% caffeine in water solution, applied for 30 minutes (50 mg total caffeine applied).
3. 1.8% caffeine in water solution, applied for 30 minutes under OECD 428 amounts (0.3 mg total caffeine applied).
4. 1.8% caffeine in water solution, applied for 24 hours under OECD 428 amounts (0.3 mg total caffeine applied).

Figure 6:
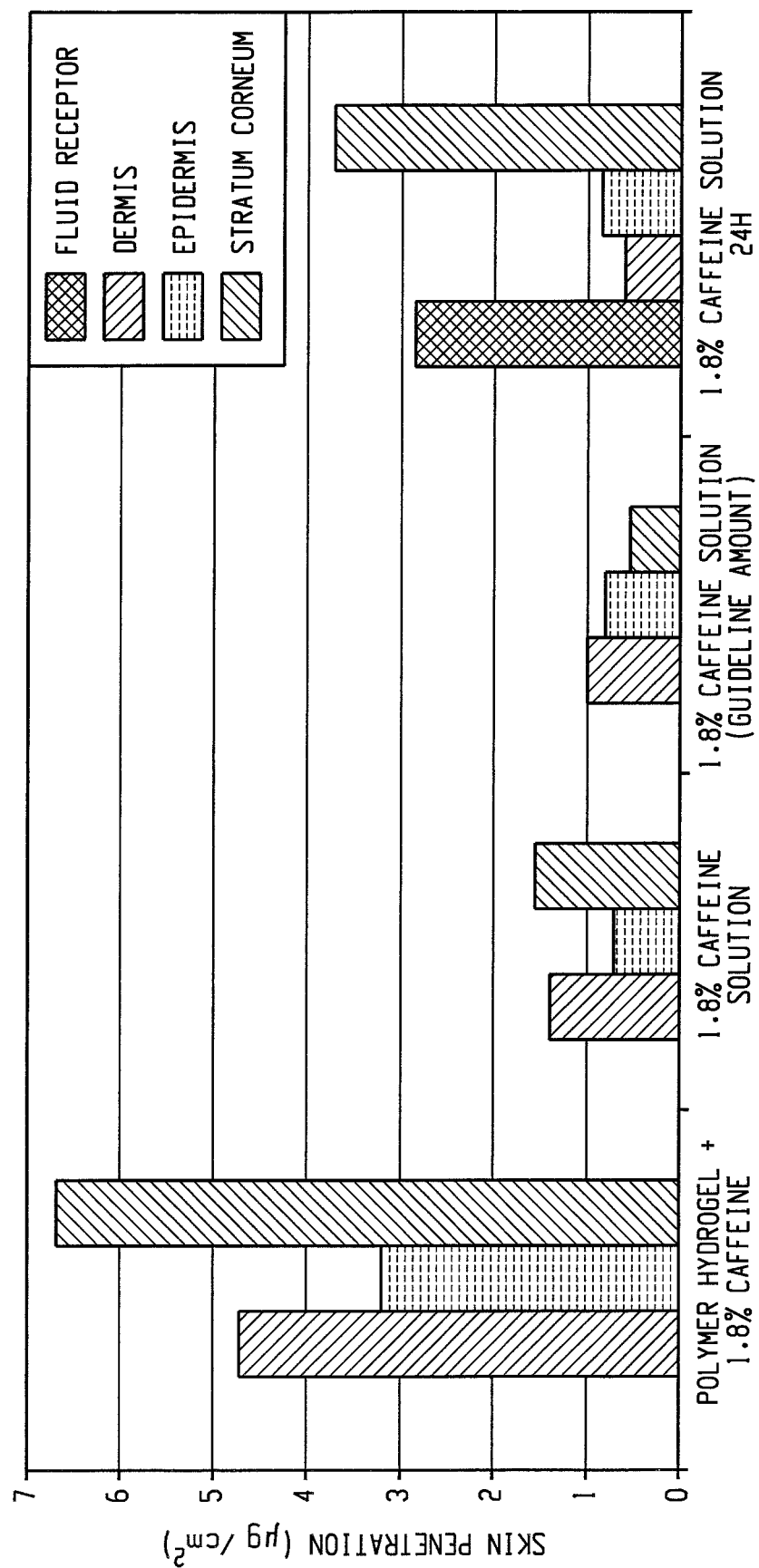
FIG. 6 illustrates percutaneous absorption by pig skin of 1.8% caffeine solution loaded on an exemplary polymer film.

The results of the Franz cell studies suggest that the exemplary polymer hydrogel increases, by more than 3 times, the amount of caffeine found in the skin layers as compared to the same caffeine amount applied in a single lotion after only 30 minutes of application (see FIG. 6).

Figure 7:
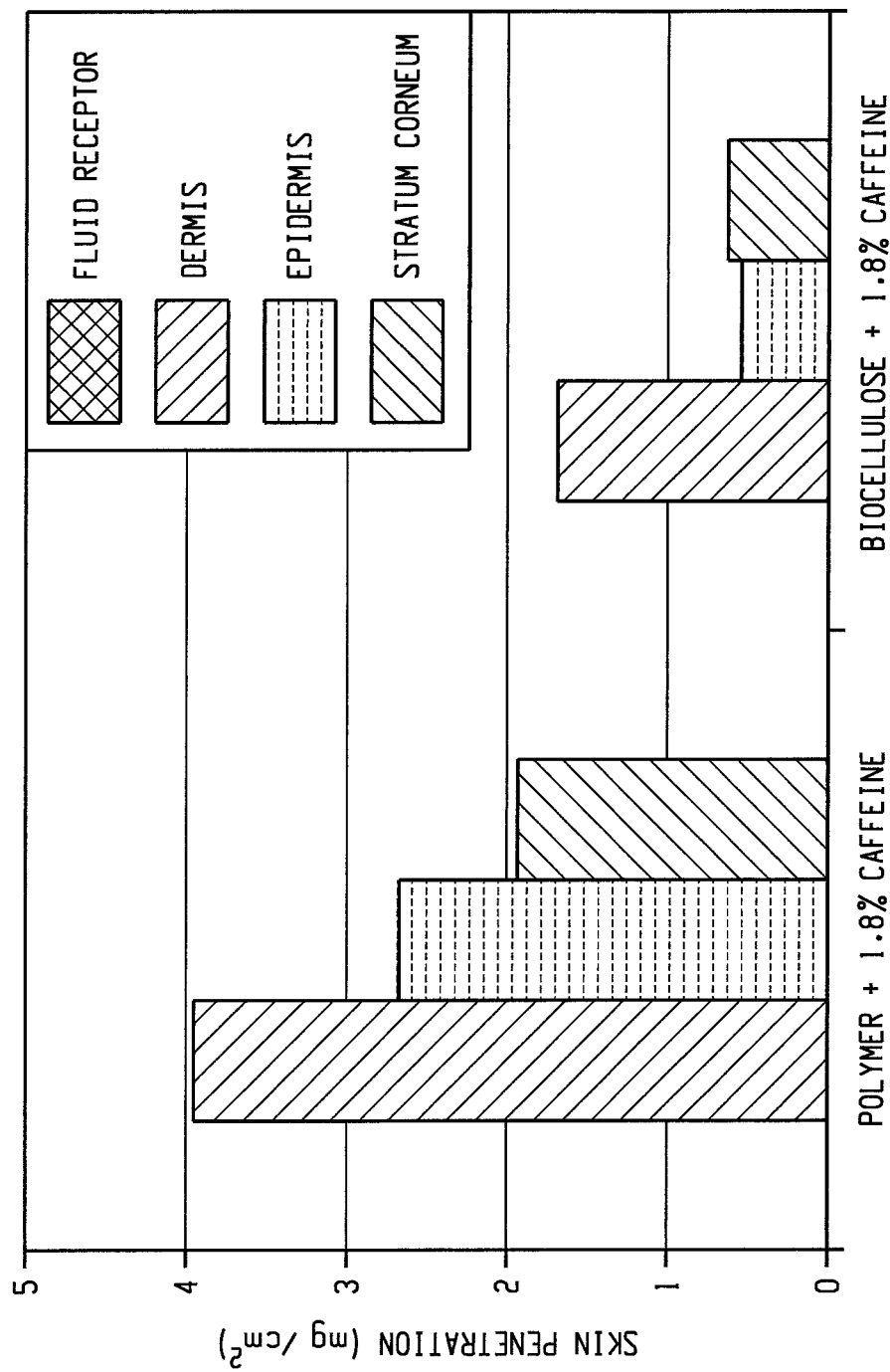
FIG. 7 shows percutaneous absorption by pig skin of a 1.8% caffeine solution loaded on an exemplary polymer film and on biocellulose (microbial cellulose)

Additionally, another hydrogel polymer film which one (with a different thickness) is tested against a typical benchmark mask made of Biocellulose in order to compare caffeine permeation. Results comparing the exemplary polymer film versus Biocellulose suggest that the polymer hydrogel increases by more than 2 times the amount of caffeine found in the skin layers compared to the same caffeine amount applied in Biocellulose after only 30 minutes of application (FIG. 7).

Results relating to microbiological risk, using analysis by water activity measurements are shown in TABLE 43.

TABLE 44

Comparison of microbiological analysis of the exemplary experimental polymer film vs Biocellulose

| | Exp. Polymer | Biocellulose |
|---|---|---|
| Temperature (° C.) | 24 | 23.5 |
| Relative Humidity (%) | 51.8 | 54.5 |
| Water activity | 0.48 | 0.55 |

According to ISO 11930 "Evaluation of antimicrobial protection of a cosmetic product", when a cosmetic product is a formulation intrinsically hostile to microbial growth and it needs specific manufacturing conditions, packaging type and/or condition for use, the ISO 29621 "Guidelines for the risk assessment and identification of microbiologically low-risk products" are applied. According to these guidelines, if the water activity (WA) is below 0.5, the product is hostile to microbial growth. In this case, there is no need of preservatives in the dried polymer to avoid microbiological contamination.

During the sensory evaluation, the panel noticed face masks made from polymer hydrogel offered a more pleasing experience than the classic face mask sheets due to better handling resistance, better aesthetics and softness, higher transparency, and absence of residue upon removal.

b) Skin Study with Dimethylmethoxy Chromanyl Palmitate

The same experiment is performed as in Example 6a, but in this case using a lipophilic whitening ingredient (dimethylmethoxy chromanyl palmitate). In this case, two different experiments are performed with the same concentration of dimethylmethoxy chromanyl palmitate.
1. 2% Dimethylmethoxy chromanyl palmitate in the polymer hydrogel, applied for 30 minutes (387 mg total applied).
2. 2% Dimethylmethoxy chromanyl palmitate encapsulated in liposomes, applied for 30 minutes (387 mg total applied).

Figure 8:
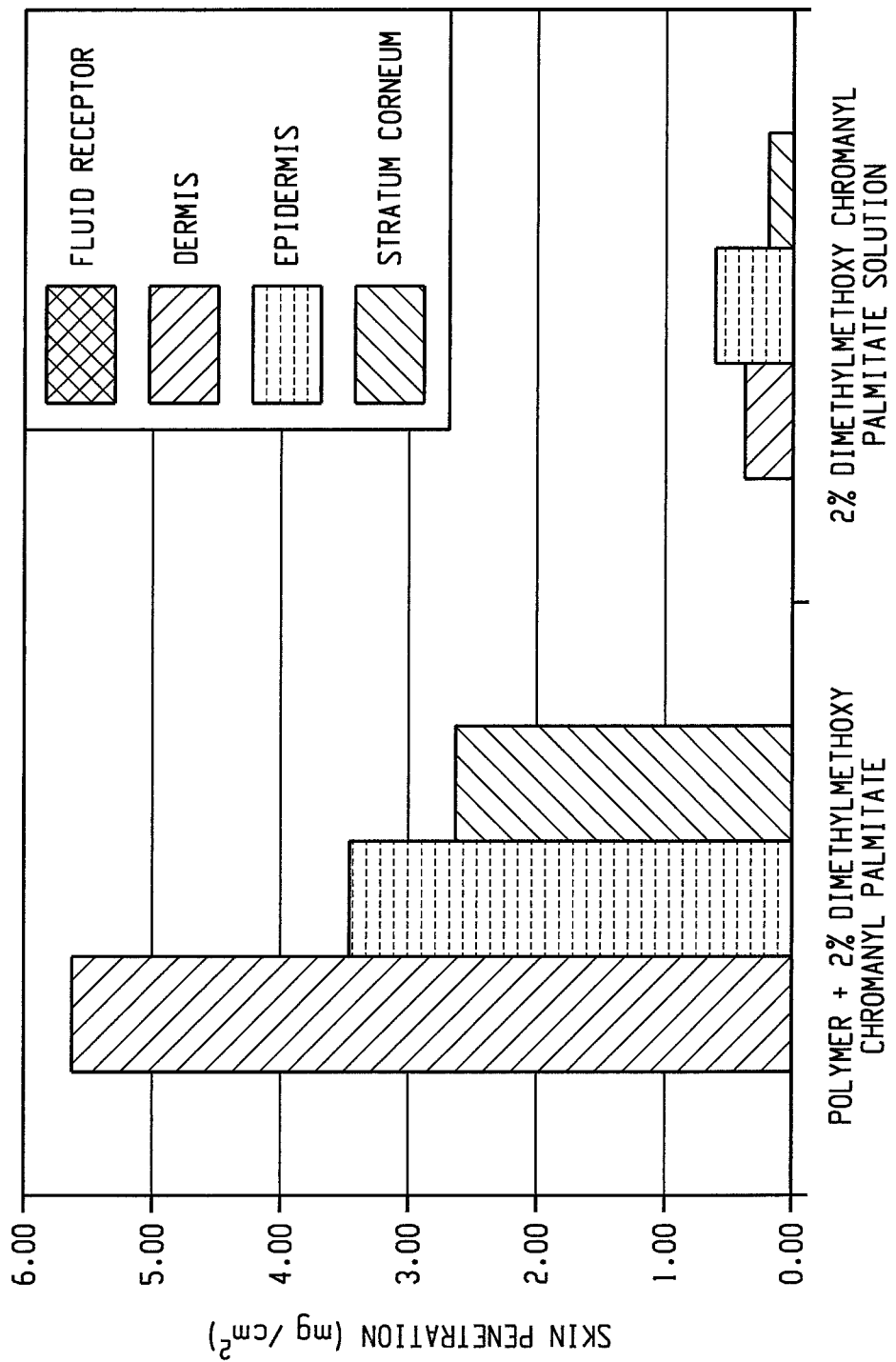
FIG. 8 shows percutaneous absorption by pig skin of 2% dimethylmethoxy chromanyl palmitate solution loaded on an exemplary polymer film.

In this study, dimethylmethoxy chromanyl palmitate penetrates much more from the film polymer than from the liposomes (FIG. 8). Results are even better than for the hydrophilic active (caffeine), obtaining around ten times more skin permeation than the active inside the liposome, which is a conventional delivery system to increase skin permeation.

c) Skin Study with Salicylic Acid

A skin permeation study is performed on dermatomed human cadaver skin, thickness ranging 400-1500 μm, surface area of 0.25 ft² (0.093 m²) obtained from The New York Firefighters Skin Bank. Skin is cut into about 2 cm² pieces with sterilized scissors, and soaked in filtered pH 7.4 phosphate buffered saline (PBS) at room temperature for 15-30 minutes to allow thawing. Then, a Franz diffusion cell is assembled with thawed skin, connected to a circulating water bath system, and equilibrated to 37° C. for at least 15-30 minutes.

A circular area of a drug loaded film is cut using a biopsy punch that fits 0.64 cm² area of skin. The drug loaded film is prepared as described in TABLE 15. The circular pieces are applied as the donor on the skin with aid of a glass rod. After preparation, the donor compartment is left non-occluded exposing to air. In addition, 3 to 5 pieces of these circular films are analyzed for salicylic acid content by HPLC.

For the solution samples, a certain volume of the solution that contains a similar salicylic acid content to the circular film pieces is applied on the skin using pipet. Five replicates per sample are performed.

The loaded films or solutions are applied to the skin (in contact with the stratum corneum) for 30 minutes. Then film or sample is removed and collected in centrifuge tube. A Q-tip soaked with PBS is used to gently wipe the skin to remove excess formulation and is collected along with the film. Sample will further be storage at 4° C.

To collect stratum corneum, 3M Scotch Book Tape 845 is cut into 1.5 $cm^2$ pieces for tape stripping. The PBS-washed skin is mounted on aluminum foil plus a support using 4 pins (one on each corner). The skin sample is sandwiched between a pre-cut plastic sheet with circular area of 0.64 $cm^2$ and aluminum foil. The skin is stripped 20 times with 1.5 $cm^2$ 3M Scotch Book Tape 845 by pressing gently with a spatula to the area that was exposed to the formulation. The 20 tapes are pooled into one sample and extracted with 10 ml of methanol in a 37° C. water bath overnight. Then the samples are stored at 4° C. until HPLC analysis.

After tape stripping, the area of the viable epidermis and dermis that has been in contact with the formulation is further cut into small pieces with sterile scissors. The small pieces of skin are collected in micro-homogenizer tubes. Samples are incubated in a 37° C. water bath overnight. The samples are then subjected to homogenization using a micro tube homogenizer. The samples are then centrifuged and the supernatant is collected in HPLC vials. The samples are stored at 4° C. until HPLC analysis.

All of the 5 mL of receptor compartment is collected into a 15 mL polypropylene tube, lyophilized and stored at 4° C. until HPLC analysis.

Polymer K, D and L loaded with salicylic acid are tested in the skin permeation study, and a hydroalcoholic solution with 10% ethanol is tested as a reference to determine any improved permeation effect by the films:
   2% salicylic acid in the experimental polymer film K, applied for 30 minutes.
   4% salicylic acid in the experimental polymer film D, applied for 30 minutes.
   2% salicylic acid in the experimental polymer film L, applied for 30 minutes.
   2% salicylic acid in hydroalcoholic solution, applied for 30 minutes.

Figure 9:
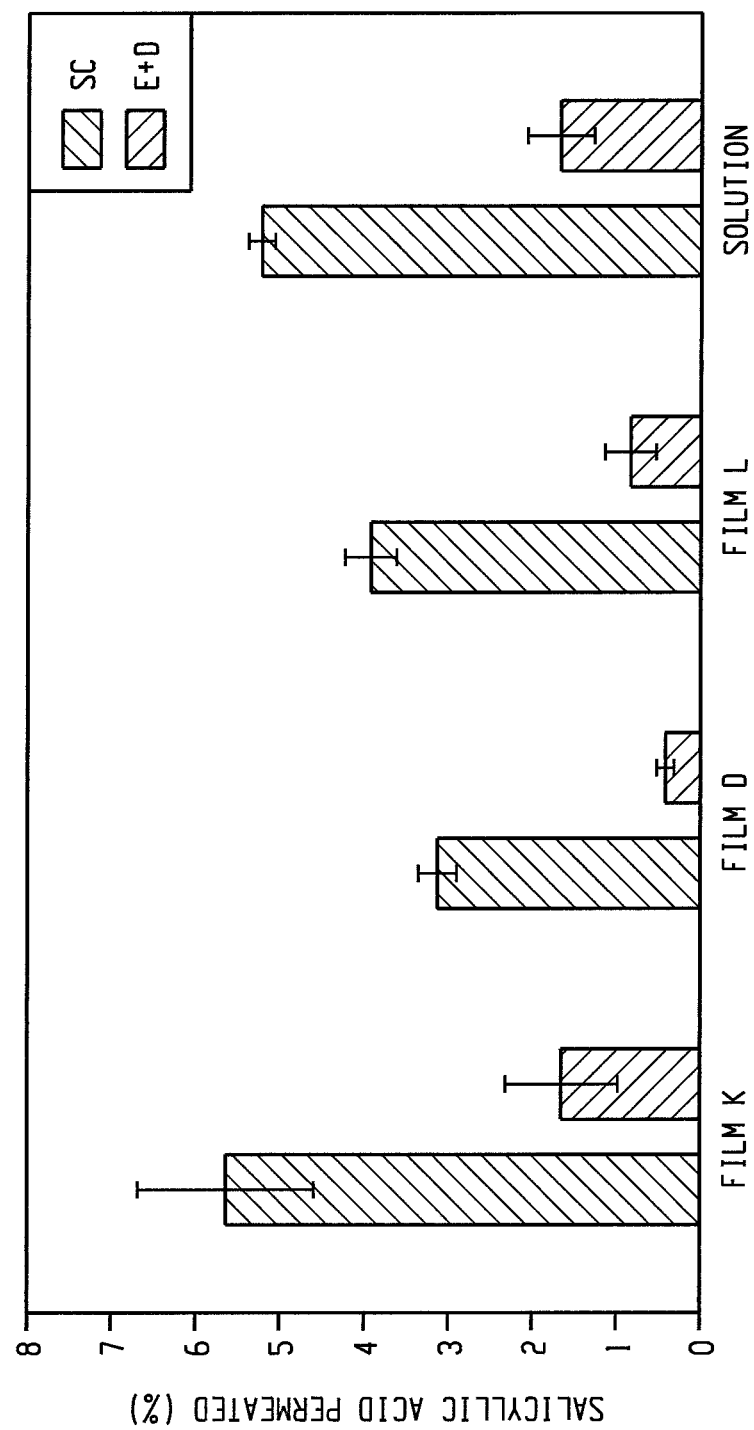
FIG. 9 shows salicylic acid penetration in skin from polymer films.

The results of the skin permeation study suggest that the exemplary polymer K improves salicylic acid permeation in the stratum corneum, compared to hydroalcoholic solution which contains 10% ethanol to increase skin permeation (see FIG. 9).

d) Skin Study with Lidocaine HCl

Skin preparation and assembling of the Franz diffusion cell was performed as for the skin study with salicylic acid.

The loaded films or commercial patch are applied to the skin (in contact with the stratum corneum) for 24 hours. 300 µl of the receptor compartment media is withdrawn at 0.5, 1, 2, 4, 8 and 24 hours for HPLC analysis, and replaced with 300 µl of fresh PBS. At 24 hours, the donor compartment (film or patch sample) is removed and collected in a centrifuge tube. A Q-tip soaked with PBS is used to gently wipe the skin to remove excess formulation and is collected along with the sample film or patch. Samples are lyophilized and dispersed in 10 ml methanol and stored at 4° C. until HPLC analysis.

The area of the skin is that has been in contact with the formulation is further cut into small pieces with sterile scissors. The small pieces of skin are collected in micro homogenizer tubes and 1 ml of methanol added to each tube. Samples are stored in the fridge until being subjected to homogenization using the micro tube homogenizer. Then, the samples are centrifuged and the supernatant is collected in HPLC vials. The samples are stored at 4° C. until HPLC analysis.

Figure 10:
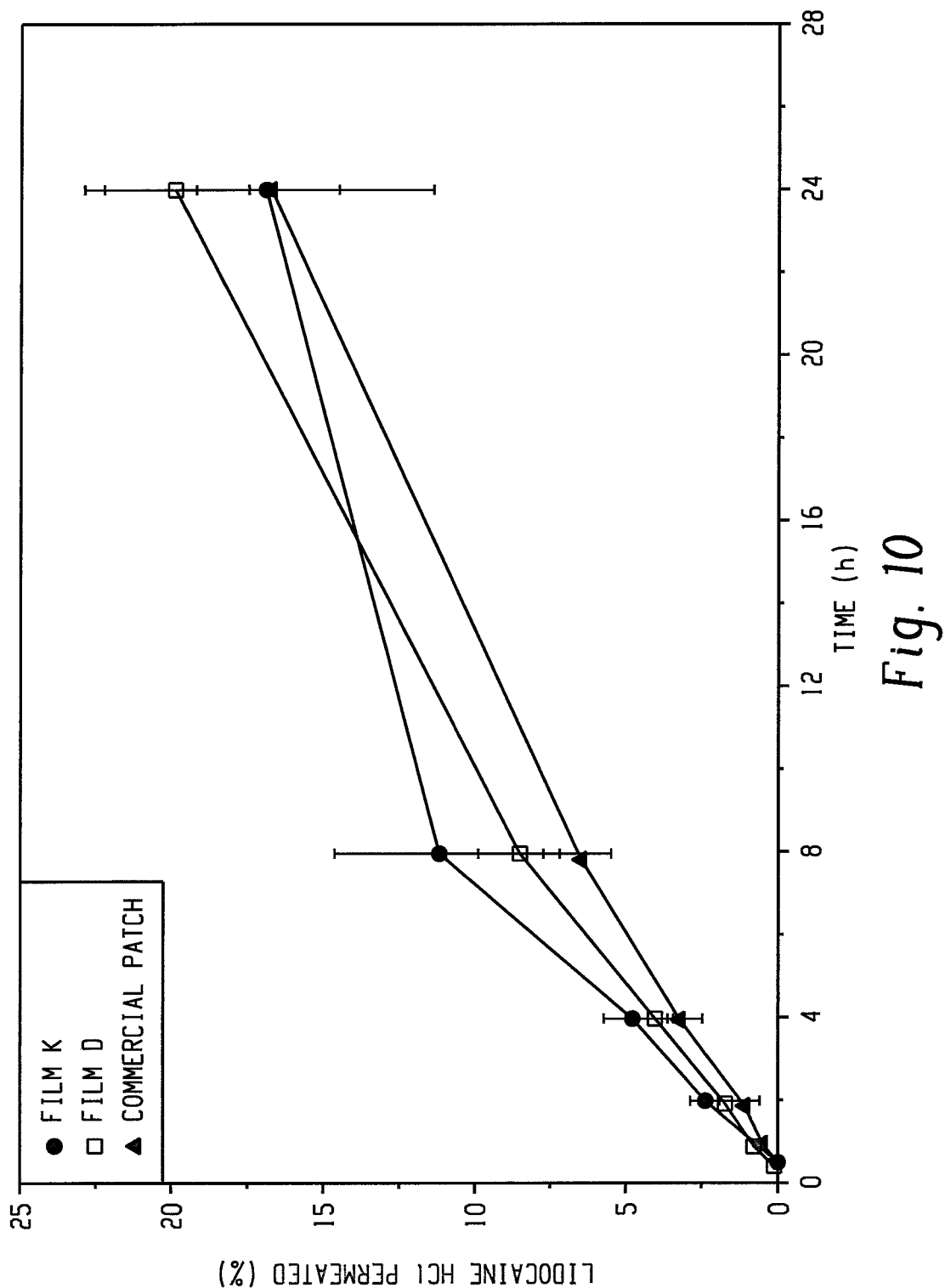
FIG. 10 shows lidocaine hydrochloride penetration in skin from polymer films.

Polymer K and D loaded with lidocaine HCl are tested in a skin permeation study, and one commercial patch is tested to compare to the experimental films:
   5% lidocaine HCl in polymer film K
   5% lidocaine HCl in polymer film D
   5% lidocaine base in the commercial patch The results of the skin permeation study suggest that the exemplary polymer K increases lidocaine HCl penetration in skin, 2 times higher than that from commercial patch in the first 8 hours (see FIG. 10). Film D also induces higher drug penetration than commercial patch within 24 hour application, and shows higher penetration percentage than Film K in the long term (16-24 hours).

e) Skin Study with Diclofenac Sodium

Skin preparation and assembling of the Franz diffusion cell was performed as for the skin study with salicylic acid.

Study time and sampling time points follow the details in skin study with lidocaine HCl.

Sample preparation for HPLC analysis is performed as for the skin study with lidocaine HCl.

Figure 11:
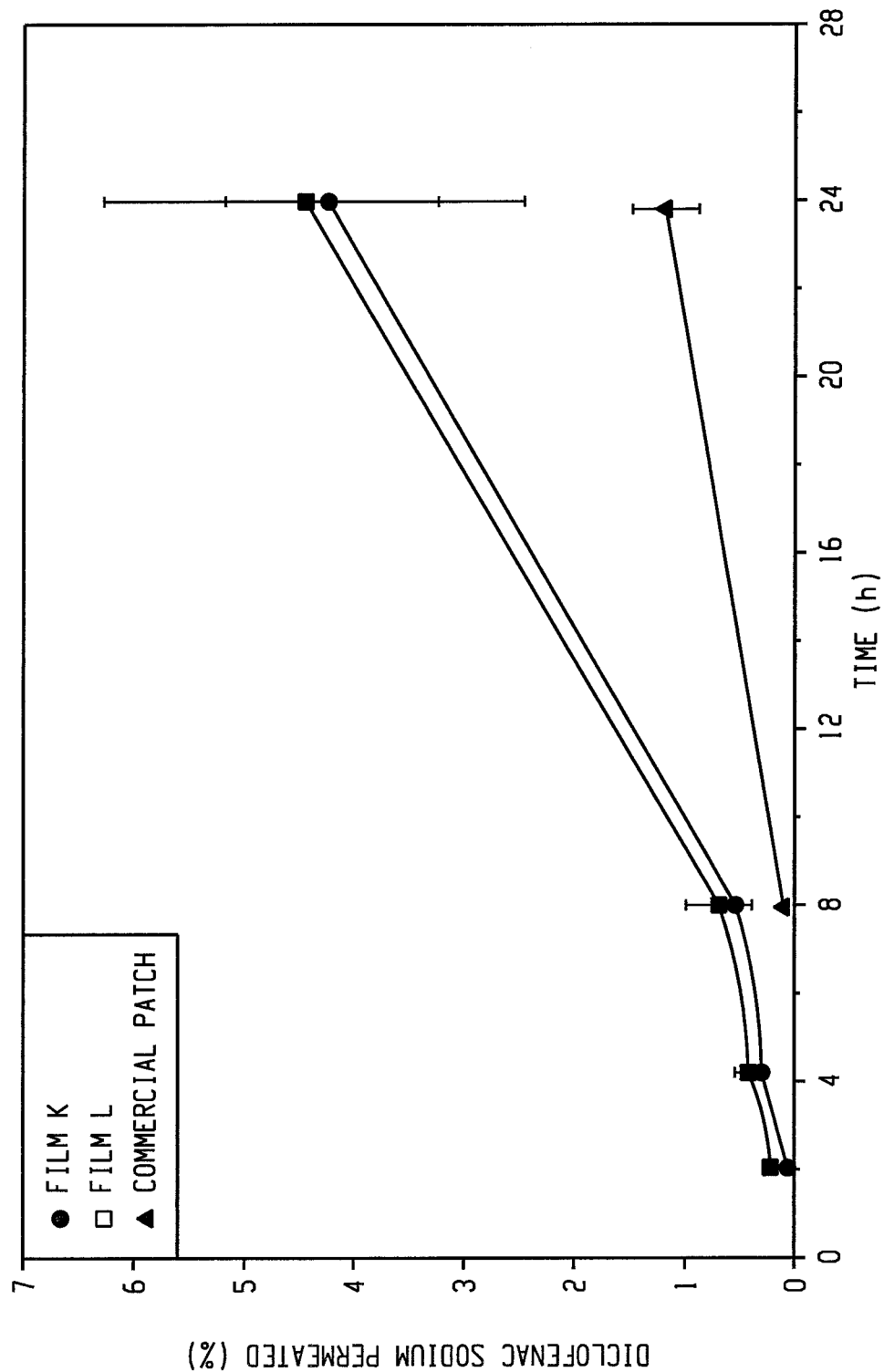
FIG. 11 shows diclofenac sodium penetration in skin from polymer films.

Polymer K and L loaded with diclofenac sodium are tested in skin permeation study, and 1 commercial patch is tested to compare to the experimental films:
   1% diclofenac sodium in the experimental polymer film K
   1% diclofenac sodium in the experimental polymer film L
   1.3% diclofenac epolamine in the commercial patch The results of the skin permeation study suggest that the exemplary polymers K and L dramatically increase diclofenac sodium penetration in skin, which compared to commercial patch, allow for earlier drug detection in skin and four times higher drug permeation percentage at 24 hour (see FIG. 11).

These studies demonstrate facial masks made from the exemplary polymer hydrogels improve skin penetration of active ingredients for better performance or formulation cost optimization. Due to the strong mechanical properties, high clarity, better sensory perception, and being not conducive to microbial growth of bacteria, the results suggest that the exemplary film is highly suited to facial masks.

Each of the documents referred to above is incorporated herein by reference in its entirety, as is the priority document and all related applications, if any, of which this application claims the benefit. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention may be used together with ranges or amounts for any of the other elements.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A water-swellable, water-insoluble polymer film comprising:
   a) at least 30 wt. % of a thermoplastic polyurethane polymer which is the reaction product of:
      a first polyether polyol having a weight average molecular weight of at least 3000 daltons;
      optionally, a second polyether polyol having a weight average molecular weight of no more than 2500 daltons;
      at least one of:
         a third polyol having a weight average molecular weight of up to 800 daltons, and
         a chain extender;
      a diisocyanate; and
      optionally, a catalyst; and
   b) up to 5 wt. % water,
   wherein the thermoplastic polyurethane polymer has a soft segment content of at least 75 wt. %,
   wherein the wt. % soft segment=wt. % polyols having a weight average molecular weight of at least 250 daltons, and
   wherein when the polymer film is soaked in an aqueous formulation containing at least 50 wt. % water at a temperature of 22-26° C. for a period of 30 minutes, the film swells by at least 300 wt. %.

2. The polymer film of claim 1, wherein the thermoplastic polyurethane polymer has a hard segment content of at least 4 wt. %, wherein the wt. % hard segment=wt. % isocyanate in hard segment+wt. % diols having a weight average molecular weight of less than 200 daltons and other chain extenders, and wt. % isocyanate in hard segment=[moles isocyanate−moles polyols having a weight average molecular weight of at least 250 daltons]×Mw isocyanate.

3. The polymer film of claim 1, wherein the thermoplastic polyurethane polymer has a soft segment content of at least 80 wt. %.

4. The polymer film of claim 1, wherein the film includes at least 50 wt. % of the thermoplastic polyurethane.

5. The polymer film of claim 1, wherein the first polyether polyol has a weight average molecular weight of at least 4000 daltons.

6. The polymer film of claim 1, wherein the thermoplastic polyurethane polymer includes the second polyether polyol, the second polyether polyol having a weight average molecular weight of no more than 2000 daltons.

7. The polymer film of claim 6, wherein a ratio of the weight average molecular weight of the first polyether polyol to the second polyether polyol is at least 1.4:1.

8. The polymer film of claim 1, wherein at least one of the first polyether polyol and the second polyether polyol is of the general form:

HO—(R$^1$(R$^2$)O)$_n$—H, where:

R$^1$ is selected from C2C4 alkyl groups and mixtures thereof,

R$^2$ is selected from H and C1C2 alkyl groups and mixtures thereof, and n is an integer which represents the average number of ether units by weight in each polyol, and where n is at least 20.

9. The polymer film of claim 8, wherein a ratio of the value of n for the first polyether polyol to the value of n for the second polyether polyol is at least one of:
   at least 1.5:1, and
   up to 10:1.

10. The polymer film of claim 1, wherein the thermoplastic polyurethane polymer comprises 5-11 wt. % hard segment, 84-91 wt. % soft segment, and 2.5-4 wt. % intermediate segment.

11. The polymer film of claim 1, wherein the film further includes at least one cross-linked poly(acrylic acid) polymer.

12. The polymer film of claim 11, wherein a ratio by weight of the thermoplastic polyurethane polymer to cross-inked poly(acrylic acid) polymer is at least 5:1.

13. The polymer film of claim 1, wherein the film further includes at least one other thermoplastic polyurethane which is different from the thermoplastic polyurethane polymer a), and optionally, wherein a ratio by weight of the thermoplastic polyurethane polymer a) to the total amount of the at least one other thermoplastic polyurethane is at least 1:2.

14. The polymer film of claim 1, wherein the film has a thickness of up to 1 mm.

15. The polymer film of claim 1, wherein the film includes at least one active agent.

16. The polymer film of claim 15, wherein the at least one active agent includes at least one of the group consisting of a skin whitening or depigmentation agent, an anti-acne agent, and an anti-wrinkle or anti-aging agent.

17. The polymer film of claim 16, wherein the anti-acne agent is selected from the group consisting of salicylic acid, glycolic acid, lactobionic acid, azelaic acid, benzoyl peroxide, antibiotics, retinoids, and mixtures thereof.

18. The polymer film of claim 16, wherein the anti-wrinkle agent is selected from the group consisting of dipeptide-4, tripeptide-1, acetyl tetrapeptide-2, palmitoyl tetrapeptide-7, caprooyl tetrapeptide-3, pentapeptide-3, pentapeptide-18, dipeptide diaminobutyroyl benzylamide diacetate, palmitoyl tripeptide-5, acetyl tetrapeptide-5, acetyl tetrapeptide-9, acetyl tetrapeptide-11, acetyl tetrapeptide-22, hexapeptide-9, acetyl heptapeptide-4, palmitoyl pentapeptide-4, acetyl hexapeptide-8, acetyl hexapeptide-30, acetyl octapeptide-3, palmitoyl hexapeptide-19, diaminopropionoyl tripeptide-33, methylsilanol mannuronate, methylsilanol hydroxyproline aspartate, tripeptide-9 citrulline, tripeptide-10 citrulline, acetyl tripeptide-30 citrulline, calcium hydroxymethionine, teprenone, palmitoyl oligopeptide, acetylarginyltriptophyl diphenylglycine, dimethylmethoxy chromanol, dimethylmethoxy chromanyl palmitate, dipalmitoyl hydroxyproline, *Pseudoalteromonas* ferment extract, and mixtures thereof.

19. The polymer film of claim 16, wherein the anti-wrinkle agent comprises a compound selected from the compound of general formula (I) and cosmetically or pharmaceutically acceptable salts thereof, Formula (I)

wherein R is a linear or branched, saturated or unsaturated substituted or unsubstituted aliphatic group containing 2 to 23 carbon atoms, or a cyclic group, and wherein when R is an unsubstituted aliphatic group, its substituents are selected from hydroxy, alkoxy, amino, carboxyl, cyano, nitro, alkylsulfonyl or halogen atoms; and X is selected from O and S.

20. The polymer film of claim 15, wherein the at least one active agent includes a peptide comprising no more than 30 amino acids.

21. The polymer film of claim 20, wherein the peptide is selected from the group consisting of:
   a) a peptide comprising a sequence of at least 3 and no more than 30 adjacent amino acids from the amino end of protein SNAP-25;
   b) a peptide of general formula: X-SEQ ID NO. 8-Y:

wherein X is selected from the group consisting of hydrogen, an amino acid and an acyl group and Y is selected from the group consisting of amino, hydroxyl and thiol;
   c) a peptide of the general formula $R_1$-AA-$R_2$ its stereoisomers, mixtures thereof, and its cosmetically and pharmaceutically acceptable salts, wherein AA is a sequence of a least 3 and up to 40 adjacent amino acids contained in the amino acid sequence SEQ ID No.: 9 selected from:

```
                              (SEQ ID No.: 10)
MAEDADMRNELEEMQRRADQL, (SEQ ID No.: 11)
ADESLESTRRMLQLVESSKDAGI, (SEQ ID No.: 12)
ELEEMQRRADQLA, (SEQ ID No.: 13)
ELEEMQRRADQL,
```

-continued

```
                              (SEQ ID No.: 14)
ELEEMQRRADQ, (SEQ ID No.: 15)
ELEEMQRRAD, (SEQ ID No.: 16)
ELEEMQRRA, (SEQ ID No.: 17)
ELEEMQRR, (SEQ ID No.: 18)
LEEMQRRADQL, (SEQ ID No.: 19)
LEEMQRRADQ, (SEQ ID No.: 20)
LEEMQRRAD, (SEQ ID No.: 21)
LEEMQRRA, (SEQ ID No.: 22)
LEEMQRR, (SEQ ID No.: 23)
EEMQRRADQL, (SEQ ID No.: 24)
EEMQRRADQ, (SEQ ID No.: 25)
EEMQRRAD, (SEQ ID No.: 26)
EEMQRRA, (SEQ ID No.: 27)
EEMQRR, (SEQ ID No.: 28)
LESTRRMLQLVEE, (SEQ ID No.: 29)
NKDMKEAEKNLT, (SEQ ID No.: 30)
KNLTDL, (SEQ ID No.: 31)
IMEKADSNKTRIDEANQRATKMLGSG, (SEQ ID No.: 32)
SNKTRIDEANQRATKLMGSG, (SEQ ID No.: 33)
TRIDEANQRATKMLGSG, (SEQ ID No.: 34)
DEANQRATKMLGSG, (SEQ ID No.: 35)
NQRTKMLGSG,
and (SEQ ID No.: 36)
QRATKMLGSG;
``` d) a peptide of general formula:

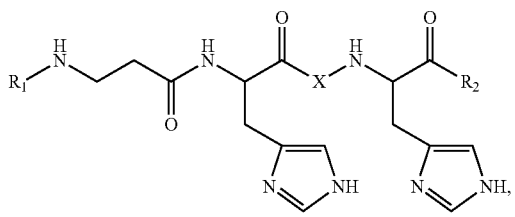

where X is selected from cysteinyl, seryl, threonyl and aminobutyryl;

e) a peptide which includes only four amino acids of general formula $R_1$-$AA_1$-$AA_2$-$AA_3$-$AA_4$-$R_2$ ($R_1$-(SEQ ID NO.: 37)-$R_2$), wherein: $AA_1$ is -Arg-; $AA_2$ is selected from -His- and -Asn-; $AA_3$ is selected from -His- and -Arg-; and $AA_4$ is -Cit-;

f) a peptide which includes only four amino acids of general formula,

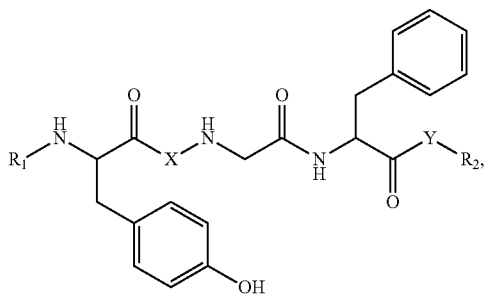

and cosmetically or dermopharmaceutically acceptable salts thereof, wherein: X and Y are selected from natural amino acids in their L- or D- form and non-encoded amino acids;

g) a peptide of only four amino acids of general formula $R_1$-$AA_1$-$AA_2$-$AA_3$-$AA_4$-$R_2$ ($R_1$-(SEQ ID NO.: 40)-$R_2$), wherein $AA_1$ is selected from -Lys-, -Orn-, -Dab-, -Dpr-, -Agl-, -3,4-dehydrolysine and -4,5-dehydrolysine; $AA_2$ is -Ala-; $AA_3$ is selected from -Asp-, -Ala-, -Asn-, -Glu- and -Pro-; and $AA_4$ is -His-;

h) a peptide having a maximum of seven amino acids of general formula $R_1$-$W_p$-$X_n$-$AA_1$-$AA_2$-$AA_3$-$AA_4$-$Y_m$-$R_2$ ($R_1$-(SEQ ID NO.: 44)-$R_2$), wherein at least one of the amino acids $AA_1$, $AA_2$ and $AA_4$ is uncoded; $AA_1$ is selected from -Arg-, -Phg- and -Nle- or is absent; $AA_2$ is selected from -Ala-, -Phg-, -Cit- and -Nle-; $AA_3$ is selected from -Trp-, -Val- and -Tyr-; $AA_4$ is selected from -Phg- and -Gly-; W, X and Y are independently selected from the group consisting of coded and uncoded amino acids; and p, n and m each range between 0 and 1;

i) a peptide having only three amino acids of general formula $R_1$-$AA_1$-$AA_2$-$AA_3$-$AA_4$-$R_2$, wherein: $AA_1$ and $AA_2$ are independently selected from -Tyr- and -Phe-; and $AA_3$ is selected from -Nle- and -Met-;

j) a peptide of general formula $R_1$-$W_n$-$X_m$-$AA_1$-$AA_2$-$AA_3$-$AA_4$-$AA_5$-$AA_6$-$Y_p$-$Z_s$-$R_2$ ($R_1$-(SEQ ID No.: 49)-$R_2$), wherein $AA_1$ is selected from -Asp-, -Glu- and -Pro; $AA_2$ is -Asp-; $AA_3$ is selected from -Tyr- and -Arg-; $AA_4$ is selected from -Phe- and -Tyr-; $AA_5$ is selected from -Arg- and -Lys-; $AA_6$ is selected from -Leu- and -Met-; W, X, Y and Z are independently selected from coded amino acids and non-coded amino acids; and n, m, p and s independently have a value of between 0 and 1;

k) a peptide of general formula $R_1$-$W_n$-$X_m$-$AA_1$-$AA_2$-$AA_3$-$AA_4$-$Y_p$-$Z_q$-$R_2$ ($R_1$-(SEQ ID No.: 55)-$R_2$), wherein: $AA_1$ is -His-; $AA_2$ is selected from the group consisting of -His-, -Leu- and -Pro-; $AA_3$ is -Leu-; $AA_4$ is selected from the group consisting of -Arg- and -Asn-; W, X, Y and Z are independently selected from the group consisting of codified amino acids and uncodified amino acids; n, m, p and q each have a value between 0 and 1; n+m+p+q is less than or equal to 2;

l) a peptide of general formula:

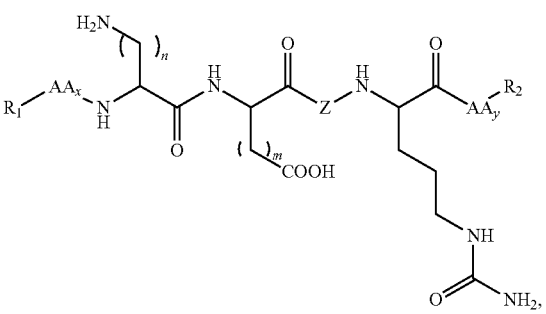

wherein: Z is selected from the group consisting of alanyl, allo-isoleucyl, glycyl, isoleucyl, isoseryl, isovalyl, leucyl, norleucyl, norvalyl, prolyl, seryl, threonyl, allo-threonyl and valyl; n and m are independently from 1 to 5; AA is selected from the group consisting of natural encoded amino acids in their L- or D-form and non-encoded amino acids; x and y are independently from 0 to 2;

m) a peptide of general formula:
$R_1$-$W_n$-$X_m$-$AA_1$-$AA_2$-$AA_3$-$AA_4$-$AA_5$-$Y_p$-$Z_q$-$R_2$ ($R_1$-(SEQ ID No.: 58)-$R_2$), wherein: $AA_1$ is selected from -Ser-, -Thr- and -Tyr-; $AA_2$ is selected from -Pro- and -Val-; $AA_3$ is -Ala-; $AA_4$ is selected from -Glu-, -Gly- and -Val-; $AA_5$ is -Gly-; $AA_6$ is selected from -Gln-, -Gly-, -His- and -Pro-; W, X, Y, Z are independently amino acids; n, m, p and q are independently selected from 0 and 1; n+m+p+q is less than or equal to 2;

n) a peptide of general formula: $R_1$-$AA_1$-$AA_2$-$AA_3$-$R_2$, where $AA_1$ is selected from -Tyr- and -Phe-, $AA_2$ is -Tyr-, and $AA_3$ is selected from -Nle- and -Met-;

o) a compound of general formula:

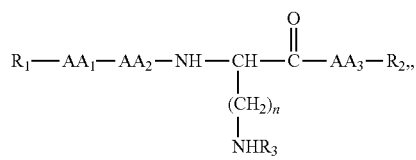

wherein $AA_1$ is selected from -Asp-, -Glu-, -Asn-, -Gln-, -Lys- and -Gly-, $AA_2$ is selected from -Val-, -Leu-, -Ile-, -Met-, -Cit-, -His-, -Thr- and -Gln-; $AA_3$ is selected from -Tyr-, -Trp- and 4-Abz-; n is selected from 1, 2, 3 and 4, R3 is selected from H and -$AA_2$-$AA_1$-$R_1$, $R_1$ is selected from H, a polymer derived from polyethylene glycol, substituted or unsubstituted non-cyclic aliphatic groups, substituted or unsubstituted alicyclyl groups, substituted or unsubstituted heterocyclyl groups, substituted or unsubstituted heteroarylalkyl groups, substituted or unsubstituted aryl groups, substituted or unsubstituted aralkyl groups and $R_6$—CO—, wherein $R_6$ is selected from H, substituted or unsubstituted non-cyclic aliphatic groups, substituted or unsubstituted alicyclyl groups, substituted or unsubstituted aryl groups, substituted or unsubstituted aralkyl groups, substituted or unsubstituted heterocyclyl groups and substituted or unsubstituted heteroarylalkyl groups; R2 is selected from $-NR_4R_5$, $-OR_4$ and $-SR_4$, wherein $R_4$ and $R_5$ are independently selected from H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and $R_1$ and/or $R_2$ are not α-amino acids;

p) a compound of general formula:

$R_1-W_n-X_m-AA_1-AA_2-AA_3-AA_4-AA_5-AA_6-Y_p-Z_q-R_2$ ($R_1$-(SEQ ID No.: 62)-$R_2$), wherein $AA_1$ is -Tyr-; $AA_2$ is selected from -Asn-, -His-, -Tyr- and -Glu-; $AA_3$ is selected from -Lys-, -Ser- and -Pro-; $AA_4$ is selected from -Gly-, -Leu-, -Lys- and -His-; $AA_5$ is selected from -Gln- and -Asn-;

$AA_6$ is -Val-; W, X, Y, Z are independently selected from amino acids n, m, p and q independently have a value of 0 or 1; and n+m+p+q is smaller than or equal to 2; and stereoisomers, mixtures thereof, and cosmetically and dermopharmaceutically acceptable salts thereof, wherein $R_1$ and $R_1$ are peptide terminating groups.

22. A hydrated film formed from the polymer film of claim 1, wherein the hydrated film comprises at least 2 g water/1 g polymer, while maintaining its integrity as a film.

23. The hydrated film of claim 22, further comprising at least one excipient selected from the group consisting of emulsifiers, organic solvents, surfactants, liquid propellants, binders and thickeners, fillers, lubricants, glidants, pigments, dyes, perfumes, flavoring agents, preservatives, and combinations thereof.

24. A face mask comprising the polymer film of claim 1.

25. The face mask of claim 24, wherein the film is supported on a release layer.

26. A face mask comprising:
up to 20 wt. % of the polymer film of claim 1;
at least one active agent at a total concentration of at least 0.00001 wt. %, and
at least 30 wt. % water.

27. A method of forming a face mask or transdermal patch comprising:
forming a thermoplastic polyurethane polymer from:
a first polyether polyol having a weight average molecular weight of at least 3000 daltons,
optionally, a second polyether polyol having a weight average molecular weight of no more than 2500 daltons, and
at least one of a third polyol having a weight average molecular weight of up to 800 daltons and a chain extender; a diisocyanate and
casting the thermoplastic polyurethane polymer with an active agent in solution to form a cast water swellable, water insoluble film which includes the active agent dispersed in the thermoplastic polyurethane polymer, whereby when the polymer film is soaked in an aqueous formulation containing at least 50 wt. % water at a temperature of 22-26° C. for a period of 30 minutes, the film swells by at least 300 wt. %, and
wherein the thermoplastic polyurethane polymer has a soft segment content of at least 75 wt. %, wherein wt. % soft segment=wt. % polyols having a weight average molecular weight of at least 250 daltons.

28. A water-swellable polymer film comprising:
a) at least 30 wt. % of a thermoplastic polyurethane polymer which is the reaction product of:
a first polyether polyol having a weight average molecular weight of at least 3000 daltons;
optionally, a second polyether polyol having a weight average molecular weight of no more than 2500 daltons;
a third polyol having a weight average molecular weight of up to 800 daltons, and
a chain extender;
a diisocyanate; and
optionally, a catalyst;
b) up to 5 wt. % water; and
c) at least one active agent, the at least one active agent including a peptide comprising no more than 30 amino acids,
wherein when the polymer film is soaked in an aqueous formulation containing at least 50 wt. % water at a temperature of 22-26° C. for a period of 30 minutes, the film swells by at least 300 wt. %.

* * * * *